US009439682B2

(12) United States Patent
Iott et al.

(10) Patent No.: US 9,439,682 B2
(45) Date of Patent: *Sep. 13, 2016

(54) POLYAXIAL SCREW

(71) Applicant: GLOBUS MEDICAL, INC, Audubon, PA (US)

(72) Inventors: Andrew Iott, Villanova, PA (US); Andrew Lee, Sebastopol, CA (US); Lawrence Binder, Miami, FL (US); David C Paul, Phoenixville, PA (US)

(73) Assignee: Globus Medical, Inc., Audubon, PA (US)

( * ) Notice: Subject to any disclaimer, the term of this patent is extended or adjusted under 35 U.S.C. 154(b) by 131 days.

This patent is subject to a terminal disclaimer.

(21) Appl. No.: 14/316,434

(22) Filed: Jun. 26, 2014

(65) Prior Publication Data

US 2014/0309697 A1 Oct. 16, 2014

Related U.S. Application Data

(63) Continuation of application No. 13/911,801, filed on Jun. 6, 2013, now Pat. No. 9,179,937, which is a continuation of application No. 13/887,098, filed on May 3, 2013, now Pat. No. 8,894,691, which is a continuation of application No. 11/294,389, filed on Dec. 6, 2005, now Pat. No. 8,475,495, which is a continuation-in-part of application No. 11/146,147, filed on Jun. 7, 2005, now Pat. No. 8,034,086, which is a continuation-in-part of application No. 10/819,994, filed on Apr. 8, 2004, now Pat. No. 7,503,924.

(51) Int. Cl.
*A61B 17/70* (2006.01)

(52) U.S. Cl.
CPC ............ *A61B 17/7037* (2013.01); *A61B 17/70* (2013.01); *A61B 17/7002* (2013.01); *A61B 17/7032* (2013.01); *A61B 17/7035* (2013.01)

(58) Field of Classification Search
CPC .............. A61B 17/70; A61B 17/7032; A61B 17/7037
USPC ........................... 606/60, 246–279, 300–331
See application file for complete search history.

(56) References Cited

U.S. PATENT DOCUMENTS

| 9,138,262 B2 * | 9/2015 | Iott .................... A61B 17/7032 |
| 2003/0004511 A1 | 1/2003 | Ferree |
| 2003/0167058 A1 | 9/2003 | Shluzas |
| 2005/0033296 A1 | 2/2005 | Bono |

FOREIGN PATENT DOCUMENTS

| WO | 00/72769 | 12/2000 |
| WO | 02/076314 | 10/2002 |
| WO | 03/045261 | 11/2002 |
| WO | 2004/071339 | 8/2004 |

* cited by examiner

*Primary Examiner* — Christopher Beccia

(57) ABSTRACT

The present invention generally is directed toward a spinal fixation system whereby a coupling element allows the physician to selectively lock or unlock either the connection between the coupling element and a fastener, such as to allow for repositioning of the coupling element, or the connection between the coupling element and an elongate rod. The locking or unlocking of these connections may be made independently and as desired by the physician.

15 Claims, 50 Drawing Sheets

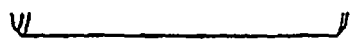
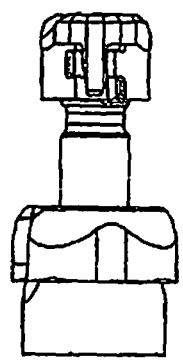
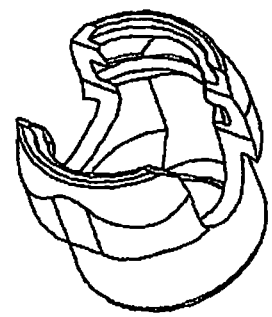
FIG. 24　　　　　FIG. 25

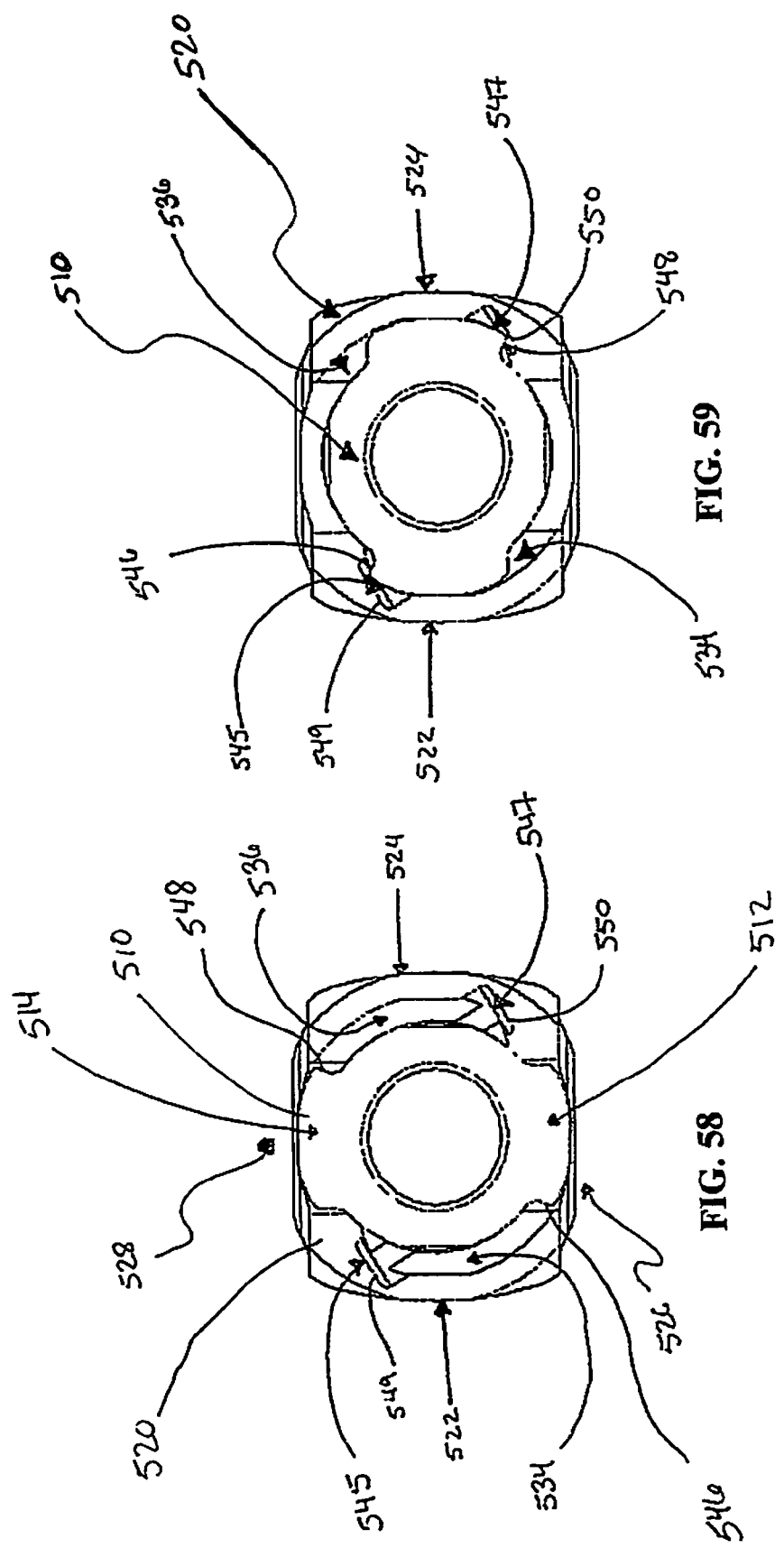

POLYAXIAL SCREW

CROSS REFERENCE TO RELATED APPLICATIONS

The present application is a continuation application of U.S. Ser. No. 13/911,801, filed Jun. 6, 2013, which is a continuation of U.S. Ser. No. 13/887,098, filed May 3, 2013, which is a continuation application of U.S. Ser. No. 11/294,389, filed Dec. 6, 2005, now U.S. Pat. No. 8,475,495, which is a continuation-in-part application of U.S. Ser. No. 11/146,147, filed Jun. 7, 2005, now U.S. Pat. No. 8,034,086, which is a continuation-in-part application of U.S. Ser. No. 10/819,994, filed Apr. 8, 2004, now U.S. Pat. No. 7,503,924, the entire contents of which are incorporated by reference in their entireties.

FIELD OF THE INVENTION

The present invention relates to orthopedic fixation devices comprising a rod and a bone screw having a variable angle head. The variable angle head of the bone screw has a coupling element that can independently lock the angulation of the head relative to the screw axis and securely prevent movement of the rod within the variable angle head.

BACKGROUND OF THE INVENTION

Many types of spinal irregularities can cause pain, limit range of motion, or injure the nervous system within the spinal column. These irregularities can result from, without limitation, trauma, tumor, disc degeneration, and disease. Often, these irregularities are treated by immobilizing a portion of the spine. This treatment typically involves affixing a plurality of screws and/or hooks to one or more vertebrae and connecting the screws or hooks to an elongate rod that generally extends in the direction of the axis of the spine.

Treatment for these spinal irregularities often involves using a system of pedicle screws and rods to attain stability between spinal segments. Instability in the spine can create stress and strain on neurological elements, such as the spinal cord and nerve roots. In order to correct this, implants of certain stiffness can be implanted to restore the correct alignment and portion of the vertebral bodies. In many cases, an anchoring member such as a pedicle screw along with a vertical solid member can help restore spinal elements to a pain free situation, or at least may help reduce pain or prevent further injury to the spine.

Some systems are directed toward immobilization of the vertebral bodies by implantation of bone screws, couplings, and elongate rods. Examples of such systems include U.S. Pat. Nos. 5,690,630, 5,669,911, and 5,672,176. It is well known that difficulties can arise during a surgical procedure when attempting to connect a vertical solid member, such as a rod, to a bone screw. As a result, it may be desirable to use a variable angled coupling element to connect a rod to a bone screw. This lessens the need to modify the system, such as by bending the rod, by repositioning the screw, or the like. The coupling element acts as an elbow which can "reach out" to the rod and allow for easier adjustment and installation of the rod in the patient.

Typically, a conventional polyaxial screw described by the prior art often has a cap of some kind is used to compress the rod onto the coupling element. This compression of the rod enables the locking mechanism within the coupling element to fix the angle between the bone screw and said element. Therefore, the vertical compression of the rod is paramount in the design of the bone screw system.

Conventional polyaxial screws also typically require that compression of the coupling element and the bone screw be achieved through the clamping of some form of taper within the coupling element. This is achieved usually by means of slits which are placed within the members of the coupling element. When these elements are placed in compression the tines created by the slits contract on the head of the screw by means of a cylindrical taper. In addition to the references mentioned above, additional examples of such systems requiring pressure from the rod to lock the position of the polyaxial screw head also can be found in U.S. Pat. Nos. Re 37,665, 5,733,286, and 5,476,464. Some systems, such as described in U.S. Pat. No. 6,248,105, describe the possibility of separately fastening the connecting body to the spherical head and elongated rod.

While these designs may provide an advantage of reducing assembly time over earlier screw designs by requiring clamping of only one fastener to hold the rod and coupling element by applying pressure against the head of the bone screw, such systems lack the ability to separately unlock or release one element, such as the rod or the coupling element.

SUMMARY OF THE INVENTION

The present invention is generally directed towards an improved anchoring system using a polyaxial screw that is capable of independently affixing a coupling member to the screw head while also permitting an elongate rod to be held securely in a desired position.

In general, the present invention may be used in a variety of spine stabilization systems. For instance, one embodiment has an elongate rod, a bone fastener having a rounded or semi-spherical head, a coupling element, and a skirt having an interior space for receiving the fastener head and coupling element. The coupling element may be formed of one piece or may comprise a plurality of connectors. A plurality of stops may be disposed on the coupling element or on the plurality of connectors, which may be configured and adapted to slidingly communicate with a coupling ring having one or more arms extending toward the fastener. The arms of the coupling ring may be selectively engaged with the stops to lock the position of the skirt with respect to the position of the fastener. Some embodiments of the present invention further comprise a cap capable of engaging with a first end of the skirt and capturing the elongate rod within a recess, channel, or opening in the skirt when the cap is rotated to a first position relative to the skirt.

In one embodiment, the cap is capable of rotating to first and second positions relative to the skirt. Rotation of the cap relative to the skirt may cause the cap to press the elongate rod toward the coupling ring so that the coupling ring arms apply pressure against the plurality of stops and lock the skirt in position relative to the bone fastener.

In another embodiment, the cap comprises a locking element capable of securely holding the elongated rod in a fixed position relative to the skirt. The cap also may have a threaded opening and the locking element may be a threaded set screw disposed within the threaded opening. Preferably, the set screw is capable of applying downward pressure on the elongate rod to lock the elongate rod in position relative to the skirt.

In still yet another embodiment of the invention, the cap and skirt may have at least one detent or protrusion and corresponding recess or depression that contact each other when the cap is in its second position to resist inadvertent loosening of the cap from the skirt. This feature may be particularly beneficial if a set screw or other locking element is used in the cap to selectively lock or unlock the elongate rod. Depending upon its configuration, rotation of the cap toward to the first or second position may cause the detent and corresponding recess to provide a tactile or audible signal to the physician. In some embodiments, a plurality of detents and recesses may be provided for each predetermined position of the cap relative to the skirt. Thus, in one embodiment, rotation of the cap to a first position relative to the skirt causes the cap and skirt to provide a tactile or audible signal, such as a click, to the physician. Moreover, in some embodiments rotation of the cap to a second position relative to the skirt results in a tactile or audible signal to the physician.

In some embodiments, the cap comprises a sidewall having a first and second channel formed therein. The first and second channels may be wider than the diameter of the elongate rod so as to allow some rotation of the cap without obstruction by the elongated rod. In one embodiment, the first and second channels are configured to permit the cap to rotate from 5° to 90° when in communication with the skirt without being impeded by the elongate rod. In yet another embodiment, unimpeded rotation of the cap is from about 20° to about 40° when in communication with the skirt and with the elongate rod.

The cap may be capable of rotating up to about 30° before reaching the first position. Moreover, the cap may be configured to provide a tactile or audible click when rotated to the first position. In addition, at least one channel in the cap sidewall may comprise a cammed upper edge that is capable of urging the elongate rod toward the coupling ring as the cap is rotated. Moreover, in one embodiment the skirt may have a plurality of threads capable of engaging with the cap and drawing the cap toward the elongate rod as the cap is rotated.

Additionally, bone fastener head may be textured with helical grooves or have some other textured surface. In one embodiment, a first connector has a first textured surface, a second connector has a second textured surface, and the first and second textured surfaces contact the rounded head when the coupling element is locked to the rounded bead.

In still other embodiments of the invention, the spine stabilization system has an elongate rod, a bone fastener having a securing element and a rounded head, and a coupling element. The coupling element may have a lower clamp element disposed on a first end of said head proximal to said securing element, said lower clamp comprising a seating surface corresponding approximately to receive a portion of the rounded surface of said head. One embodiment further includes an upper clamp element disposed on a second end of said head distal to said securing element. In some cases, the lower clamp and upper clamp may have a projection and a notch that can interconnect to restrict rotation of one clamp with respect to the other. Moreover, the system may also have a locking element disposed substantially around said first and second clamp elements. The locking element also may further have an interior surface that is at least partially threaded. In some embodiments, the threaded portion of said locking element may be selectively engaged with said threaded portion of said lower clamp. These embodiments may also have a rod locking element in communication with the upper clamp and locking element. Preferably, the rod locking element comprises a seating surface for receiving said elongate rod. As discussed above, a locking cap may be selectively engaged with said rod locking element to secure said elongate rod to said coupling element.

In still yet another embodiment of the present invention, the system may have a bone fastener having a rounded head and a coupling element. In this embodiment, the first end of the coupling element may have a skirt disposed over said rounded head, wherein said skirt comprises a slit extending from a portion of the skirt proximal to the bone fastener toward a distal end of said skirt, and wherein each of said distal and proximal ends of said skirt has one or more stops. The coupling ring may be disposed over said distal end of said skirt, wherein said coupling ring comprises one or more arms extending from said coupling ring to the proximal end of said skirt, and wherein said arms may be selectively engaged with said stops to lock said coupling element to said head. Once again, a locking cap may be selectively engaged with said coupling element to lock said elongate rod to said coupling element.

BRIEF DESCRIPTION OF THE DRAWINGS

FIG. 24 is an assembled view of a portion of the invention of FIG. 17;

FIG. 25 is an isometric view of a skirt of the present invention of FIG. 17;

FIG. 58 is a cross sectional view of the cap and coupling body of the embodiment of FIG. 54 with the cap shown in a first position;

FIG. 59 is a cross sectional view of the cap and coupling body of the embodiment of FIG. 54 with the cap shown in a second position;

DETAILED DESCRIPTION OF THE INVENTION

Figures 1, 2:
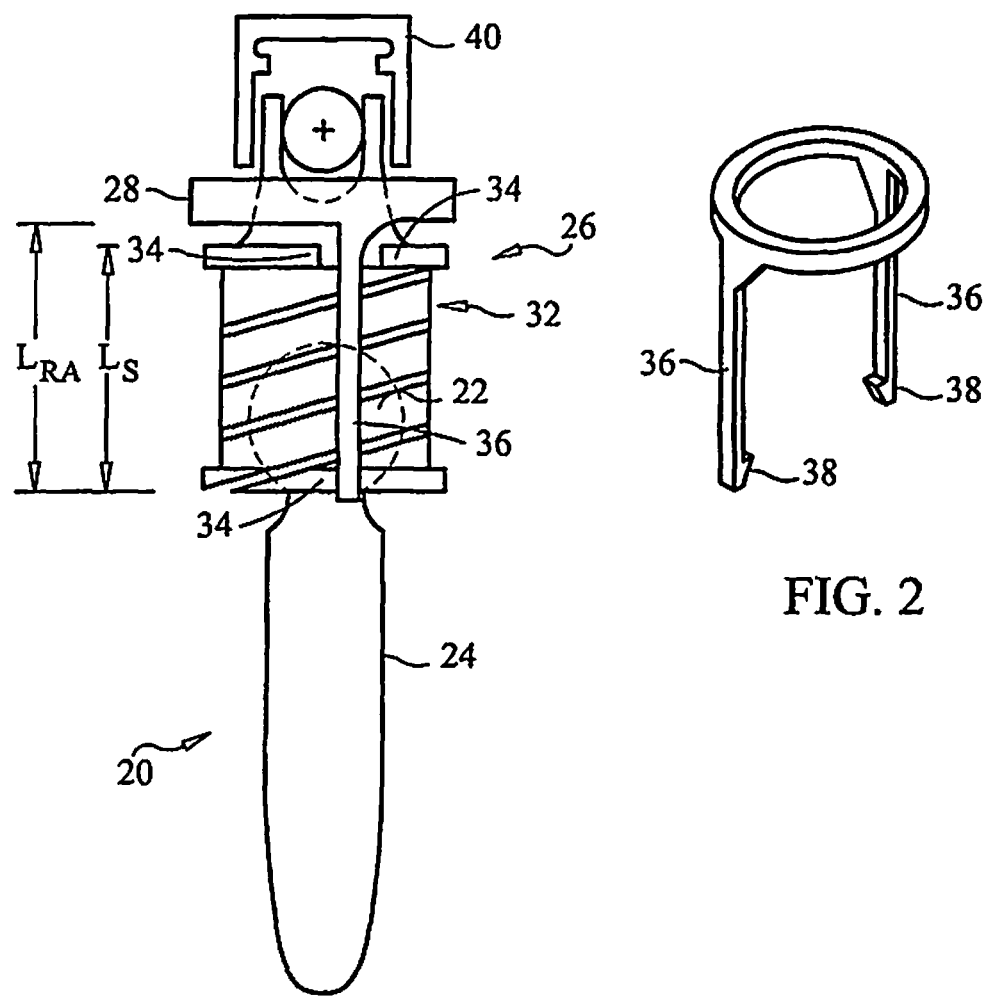
FIG. 1 illustrates one embodiment of the invention having an elongated rod and a variable angle fastener with a wedge ring, a slotted body disposed around the head of a screw, and a locking cap.
FIG. 2 shows an isometric view of one embodiment of a wedge ring of the embodiment of FIG. 1.

The present invention generally is directed toward a spinal fixation system whereby the locking of an elongate rod plays may not be necessary in order to lock the angle between a fastener, such as a screw, and a coupling element. Instead of requiring full application of locking pressure on an elongated rod in order to lock the coupling element securely in place with respect to the screw head, some embodiments of the present invention utilize a coupling locking device that is capable of securing the coupling element to the screw independent of the rod or with forces imparted by the rod that are less than the forces used to lock the rod in place. Likewise, some embodiments of the present invention also may utilize a rod locking device that is capable of securing the rod to the coupling element in a manner that is independent of the coupling locking device. In addition, some embodiments of the present invention permit a coupling element to lock in place relative to the fastener head by downward movement of the elongated rod. Once the coupling element is locked, the rod may be moved upward or repositioned without causing the coupling element to unlock or come loose. Thus, unlike prior spine stabilization systems, many embodiments of the present invention permit separately locking or unlocking of either the rod and coupling element or the coupling element and screw.

As explained by the examples and illustrations below, the coupling locking device and the rod locking device can be configured and adapted in several different ways while still allowing independent operation or independent locking. Through the means of cams, wedges, or threads, this invention can place a compression on the head of the screw without use of the elongated rod. The invention further seeks to reduce the number of steps in the procedure, reduce the size of the coupling element, and reduce the number of separate pieces associated with the implant. This will reduce intra operative time, create less complicated procedures, and work well in a wider variety of patient anatomy.

While many features of the invention will be described more fully below with reference to the accompanying drawings illustrating several embodiments of the invention, it is to be understood at the outset that skilled artisans having the benefit of this disclosure may recognize further variations or modifications of the invention that may also achieve the functions and results of this invention. Accordingly, the descriptions which follow are to be understood as illustrative and exemplary of specific structures, aspects, and features within the broad scope of the invention and not as limiting of such broad scope.

Each of the embodiments described below and in the associated figures describes a polyaxial fastener having a screw and coupling element assembly for use with an orthopedic rod implantation apparatus. While the embodiments are described and illustrated as having a screw that has a head and a shaft that extends from the head, it should be understood that other fasteners or securing elements may also be used such as, for example, lamina hooks and sacral blocks. Thus, the present invention may be used with a wide variety of fasteners or securing elements in addition to a bone screw as described herein.

Accordingly, FIG. 1 illustrates a side view of a screw 20 suitable for use in the invention. The screw 20 includes a head 22 and a shaft 24 that extends from the head 22. The shaft 24 is shown as having a tapered shape, which may be configured with a high pitch thread, although once again, skilled artisans would recognize that other shaft designs also would be compatible with the invention. Thus, the physician is free to select from a variety of shaft features, such as thread pitch, shaft diameter to thread diameter ratio, overall shaft shape, and the like according to the conditions of the individual patient's bone.

While the head 22 may have any shape, it is preferred that the head has a tapered neck with a rounded head to provide increased adjustability. Thus, at least a portion of the head may be shaped to form a portion of a ball or at least a portion of a sphere above the neck in order to allow for rotational or angular adjustment of the coupling element 26 with respect to the fastener 20. This preferred configuration also allows the coupling element 26 to more securely grip the head 22. In other words, at least a portion of the head 22 has a curved surface from which the shaft extends. The curved portion of the head can be a semi-spherical in shape, exhibiting an external contour that is equidistant from a center point of the head. In addition, the head may have an engagement surface that can be engaged by a screwdriving tool or other device, it is preferable that the engagement surface does not disrupt the functionality of the curved surface.

The diameter of the head 22 may be approximately the same as the largest diameter of the shaft 24. The neck may be tapered to provide greater curvature of the head 22 in order to provide a greater variety of angles and positions in which the coupling body and screw or fastener may be arranged. It should be noted that in other embodiments, the diameter of the shaft 24 can be less than or greater than the diameter of the head 22, and the neck may be un-tapered or differently tapered.

Figure 10:
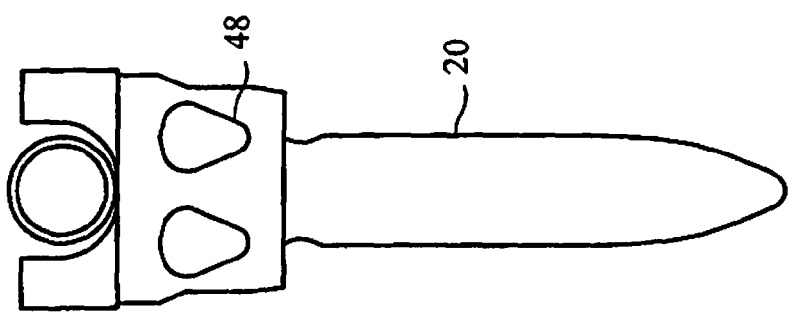

The head 22 also may have an engagement surface that permits the physician to apply torsional or axial forces to the screw with a wrench or screwdriving tool to drive the screw into the bone. For instance, the engagement surface of the head 22 may be a polygonal recess as shown in FIG. 10 in which the head of a tool can engage. For example, the head 22 may have a hexagonal recess that receives a hexagonal tool such as an allen wrench. The engagement surface also may be configured with a protruding engagement surface that likewise may engage with a tool or device having a corresponding recess, although preferably the protruding engagement surface would not significantly interfere with the capability to vary the angle of the coupling element with respect to the screw 20. The engagement surface may have other shapes as well, such as a slot or a cross found typically used with other types of screwdrivers.

Prior to being locked into place, a coupling element 26 associated with the head 26 can be moved and rotated into a plurality of positions. The coupling element is configured and adapted with a seat or interior surface that receives the head 22 on a first end and an elongated rod on the opposing end. At least a portion of the head may have a roughened or textured surface that improvise engagement between it and other component of the polyaxial screw when in a locked or tightened position. With respect to the embodiment shown in FIG. 1, the coupling element comprises a coupling ring 28 and a coupling body 30. The coupling body has a skirt 32 that defines the seat or interior surface that receives the head 22. Preferably, the skirt may be selectively locked or unlocked against the head by providing one or more slits or openings that allow the seat or interior surface of the coupling element to constrict and securely engage with the head 22 in a locked position or be expanded or unlocked as desired. In one embodiment, shown in FIG. 1, the coupling body has one or more generally helical slits. More preferably, the slits or openings extend from a free end of the skirt proximate to the screw or fastener 20 to a location above the head 22.

The coupling body 30 has a plurality of stops 34, preferably disposed near the upper and lower ends of the coupling body skirt 32. The stops 34 may be configured with flanges with openings or slots through which the coupling ring may be placed so that the skirt 32 approximates the shape of a spool. The stops 34 are positioned so that as the coupling ring 28 is connected to the coupling body 30 torsional forces are applied to the skirt 32 causing it to twist and constrict against the head 22.

As shown in FIG. 1, the coupling ring 28 is configured to have one, two, or more arms 36 that extend from the ring 28 and engage with the stops 34. As the coupling ring 28 is placed onto the coupling body 30, the arms 36 slidably engage with the stops with minimal torsional forces imparted to the skirt until a wedge near the base of the arms proximal to the ring contacts one of the stops. After the wedge has engaged with one of the stops, further insertion of the ring over the coupling body will cause it to turn about the longitudinal axis of the skirt. As the ring is turned, the distal end of the arms will engage with stops 34 and apply torsional forces to the skirt. In one embodiment, the locking ring rotates from about 2° to about 15° from its initial, unlocked position until reaching a locked position where the coupling element is immovably secured to the screw. In another embodiment, the locking ring rotates from about 5° to about 10° from an unlocked to a locked position.

Preferably, the distal end of the ring arms 36 are configured to radially engage with a lip on the skirt once the skirt has been sufficiently turned to lock against the screw head 22. As shown in FIG. 2, for example, the distal end of the ring arm may have protrusions 38 that extend radially inward. The protrusions 38 can slide over the lip of the skirt and snap into place once the skirt is in its locked position. Initially, when the skirt is not in a locked position, the length of the ring arms L. from the proximal end to the protrusion may be less than the length of the skirt $L_s$. As the skirt is twisted, however, its overall length may gradually decrease, and the ring arms will splay outward as the protrusions are forced over the lip. Once the length of the skirt $L_s$, becomes approximately the same length, or shorter than the length of the ring arms $L_{ra}$, the protrusions will be released over the lip and hold the skirt in its locked position. In this embodiment, unlocking the coupling body skirt 32 from the screw head 22 can be accomplished by applying a radially outward force to the ring arms until the protrusions no longer engage with the lip. Once the protrusions are clear of the lip, the coupling ring may be rotated to unlock the coupling element. In this manner, the coupling element may be selectively locked or unlocked to the screw or fastener 20 without requiring the elongated rod to be locked in position. Thus, no forces need be imparted by the elongated rod to lock the coupling element to the screw or fastener.

Figure 3:
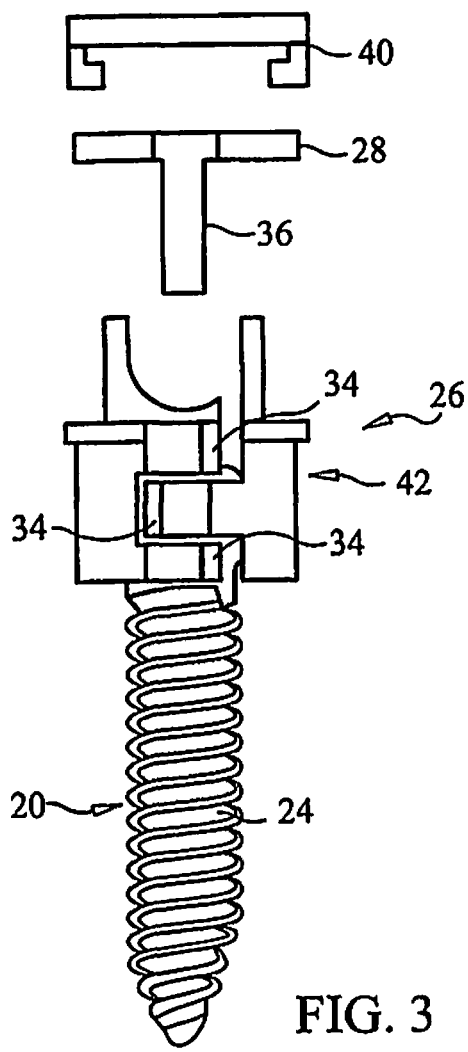
FIG. 3 illustrates one embodiment of a variable angle fastener having a 2-piece body, a wedge ring, and a locking cap.
Figure 17:
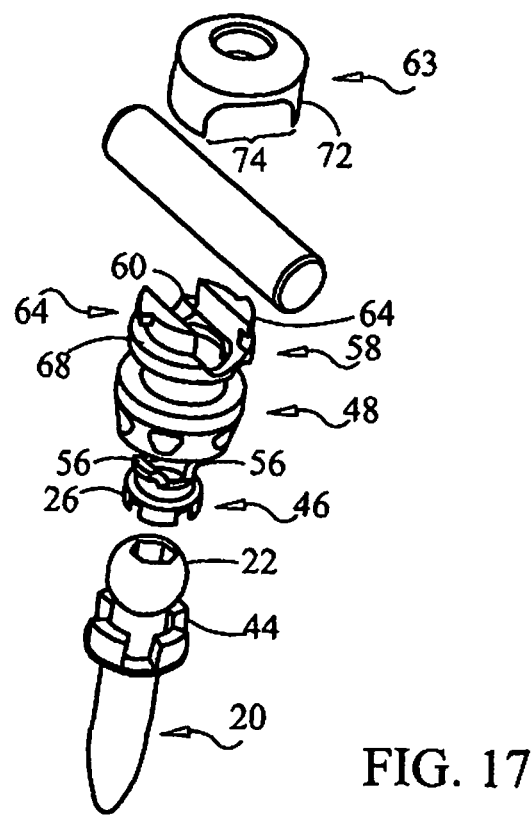
FIG. 17 illustrates an isometric view of another embodiment of the present invention prior to assembly.

Returning to FIG. 1, the coupling body also is configured and adapted to receive an elongated rod on an upper end opposite the end of the coupling body 30 configured with the coupling body skirt 32. Preferably, this portion of the coupling body is configured with a U-shaped or wedge shaped seat against which the elongate rod will be locked. Substantially rigid tines or wedges extend upward from the seat for the rod, which are configured with slots or detents that receive a cap 40. The cap, such as illustrated in FIGS. 3 and 17, may have corresponding protrusions or slots that permit the cap to engage with and rotate with respect to the coupling body 30. In one embodiment, rotation of the cap causes it to move downward and toward the screw, thereby applying a downward force against the elongate rod to hold it securely in place.

In another embodiment, the cap applies a downward pressure on the elongate rod that, in turn, causes the coupling element to be locked in position relative to the fastener while not completely locking the elongate rod in position. A set screw disposed in the cap may then apply additional downward pressure on the elongate rod to hold it firmly in position. Thus, in some embodiments the downward pressure of the cap on the rod may be sufficient to lock one component of the system while still allowing adjustability of the other component.

In an another alternative embodiment, the tines or wedges of the coupling body that extend upward from the seat for the rod may be flexible so that they bend or flex around the rod as the cap is turned toward a locking position. For instance, either the cap, the tines or wedges, or both may be configured to have a tapered or ramped surface that causes gradually increasing radial interference with the cap and coupling element as the cap is rotated. As the radial forces resulting from this interference increases, the tines or wedges may bend or flex radially inward and press against the elongate rod. One or more detents and depressions may be placed on either the cap or the coupling body to hold the cap in a locked position by engaging with each other at a desired cap position. Rotation of the cap in the opposite direction likewise causes the elongated rod to become unlocked.

Thus, in several embodiments of the invention the elongate rod may be selectively locked or unlocked in place without requiring the coupling body to be unlocked from its position with respect to the screw.

FIGS. 3-8 illustrate several features and variations of yet another embodiment of the invention. Several features of this embodiment are similar to those described above. For example, the screw or fastener 20 may be configured or varied according to the physician's preference. It has a head 22 on which a coupling element 26 communicates. As mentioned above, the head 22 may be generally spherical in shape. The coupling element 26 may be positioned and rotated in several directions, and may be selectively locked or unlocked in position. The coupling element likewise has a coupling body 30 and coupling ring 28 with ring arms 36 that is capable of locking the coupling element 26 to the screw or fastener 20.

Figure 5:
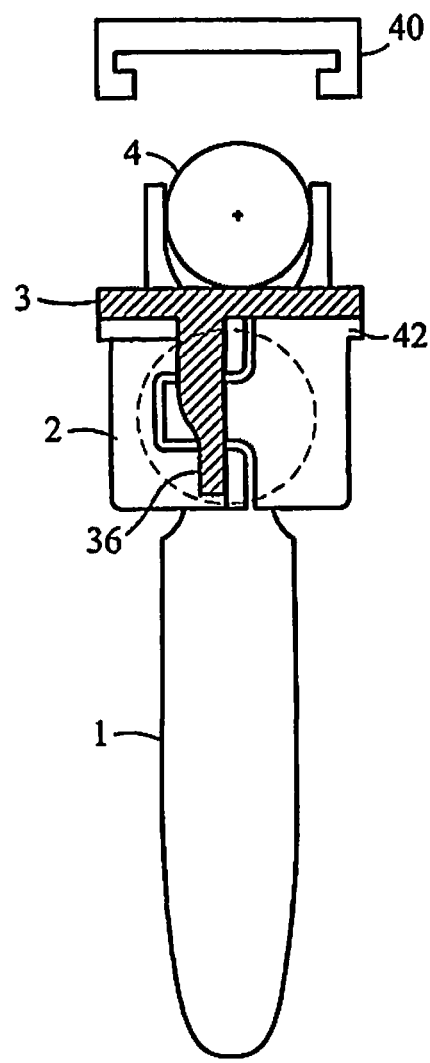
FIG. 5 illustrates a variation of the embodiment of FIG. 3 using a 1-piece body.
Figure 4:
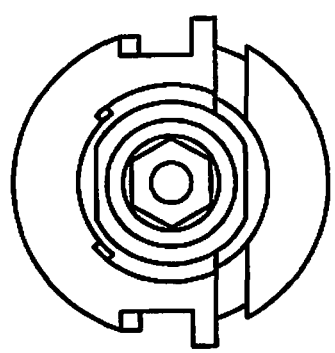
FIG. 4 shows a top view of the variable angle fastener of FIG. 3.

Rather than using a skirt that twists or rotates to lock the coupling element to the screw or fastener, however, the coupling body of this embodiment may be formed of one, two, or more coupling body components 42 that are configured with at least two stops that slidably engage with at least one ring arm 36. As shown in FIG. 5, the coupling body has at least one slit or opening extending substantially along the length of the coupling body component. More preferably, at least one slit or opening extends entirely along the length of the coupling body component, as shown for example in FIGS. 5 and 7. In one embodiment, the number of slits or opening configured in this manner increases as the number of coupling body components 42 increases. Thus, a coupling body 30 comprising at least two coupling body components 42 also will have at least two slits or openings extending generally along the axial length of the coupling body components.

Figure 7:
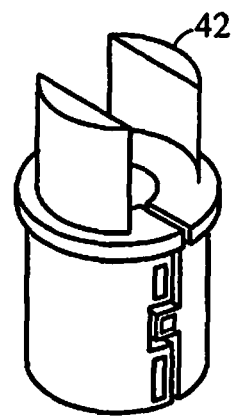
FIG. 7 is an isometric view of the 1-piece body of the embodiment of FIG. 5.
Figure 6E:
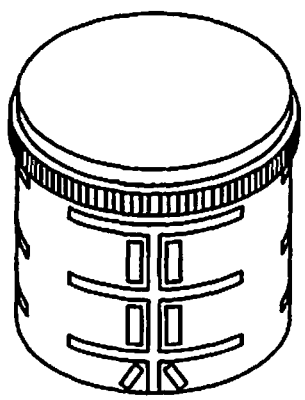

The slit or opening is thus defined by corresponding terminating edges of material formed on or more coupling body components 42. As shown in FIGS. 5 and 7, the shape of the slit or opening may be configured such that a portion of a first terminating edge may protrude into a recessed area of a corresponding portion of a second terminating edge. As mentioned previously, at least two stops 34 are configured to slidably engage with at least one ring arm 36. These stops are positioned so that as the tapered portions of the ring arms contact one or more of the stops the terminating edges defining the slit or opening are forced toward each other so that the coupling element can be locked to the head of the screw or fastener. This is accomplished by placing at least one stop on each side of the terminating edges defining the slit or opening. Thus, each ring arm may communicate with two or more stops. More preferably, at least three stops are configured to contact at least one ring arm in order to close the coupling body onto the head 22. Thus, one edge of the slit or opening may have two or more stops, while the other may have one or more stops. Even more preferably, each ring arm is configured to communicate with at least three stops arranged in this manner.

Figure 6A:
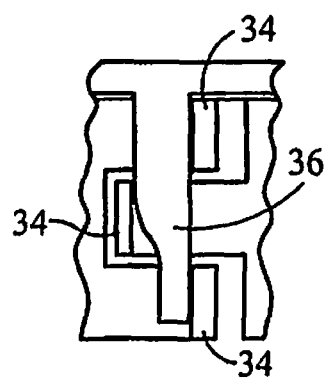
FIGS. 6A-6E illustrate different views of different coupling body embodiments of the present invention.
Figure 6B:
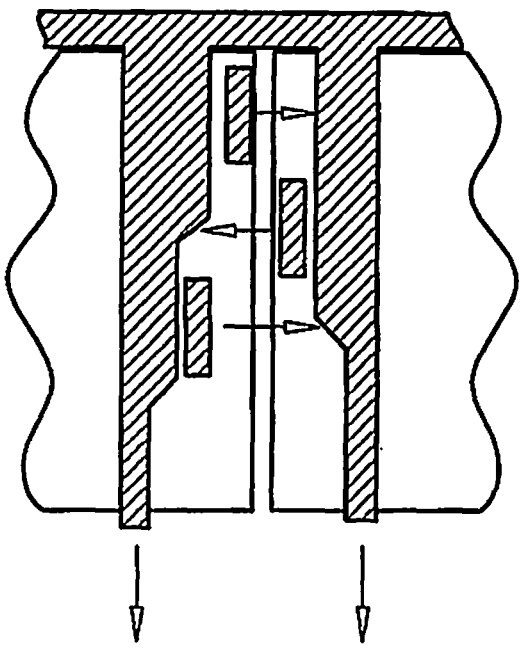
Figure 6C:
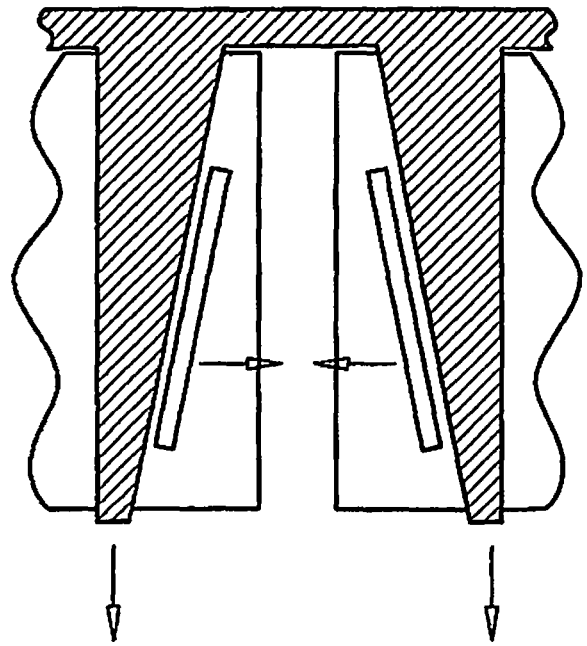
Figure 6D:
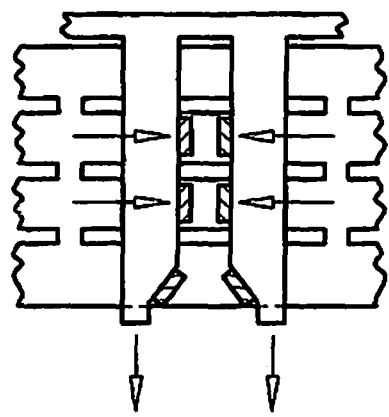

As shown in FIGS. 3, 5, and 6A, the terminating edges or the coupling body components 42 may be configured in a tongue and groove fashion so that the tapered surface of the ring arm contacts the stops on the trailing edge of the stop rather than at the leading edge. It is not necessary, however, that the terminating edges have this configuration. FIGS. 6B-D, for instance, illustrate some variations of this embodiment that do not utilize a tongue and groove configuration. More particularly, FIG. 6B illustrates that multiple wedges may be provided on the ring arms 36. This allows stops to be placed in different locations along the axial length of the coupling body, such as to allow the application of different amounts of gripping force on different portions of head 22.

FIG. 6C shows that the stops may be angled in a manner that helps encourage the terminating edges closer together as the ring arms 36 are moved toward a locking position. For instance, the angle of the stops may be from about 3° to about 15° off from the longitudinal axis of the coupling element 26, and more preferably the stops may be angled from about 5° to about 10°.

The embodiment of FIG. 6D uses a plurality of slits or openings that generally are perpendicular to the longitudinal axis of the coupling element 26. These slits or openings create an appearance of generally horizontal bands. Stops disposed near free ends of one or more horizontal bands may slidingly engage with the ring arms as they are moved toward a locking position, thereby causing the terminating surfaces of the horizontal bands to move toward each other to grip the head 22.

Locking mechanisms may be used in any of the embodiments described herein to hold the ring arms onto the coupling body in a locked position. As mentioned above, many different types of forces, such as torsional loading around or axial loading along the longitudinal axis of the coupling element 26, may be applied to the coupling ring 28 and ring arms 36 in order to lock the coupling element in position. The embodiments shown in FIGS. 6A-D, for example, have locking mechanisms disposed on the free ends of one or more ring arms.

The coupling element 26 may have a seat for receiving an elongated rod, and further may have tines that engage with a cap to independently lock the coupling element to an elongated rod. In some embodiments, the coupling element may be securely positioned with respect to the fastener head with little or no additional pressure applied to the head 22. For example, the cap may provide pressure to the sides of the tines on the coupling element, which in turn flex or bend to securely grip the elongated rod.

Figure 9:
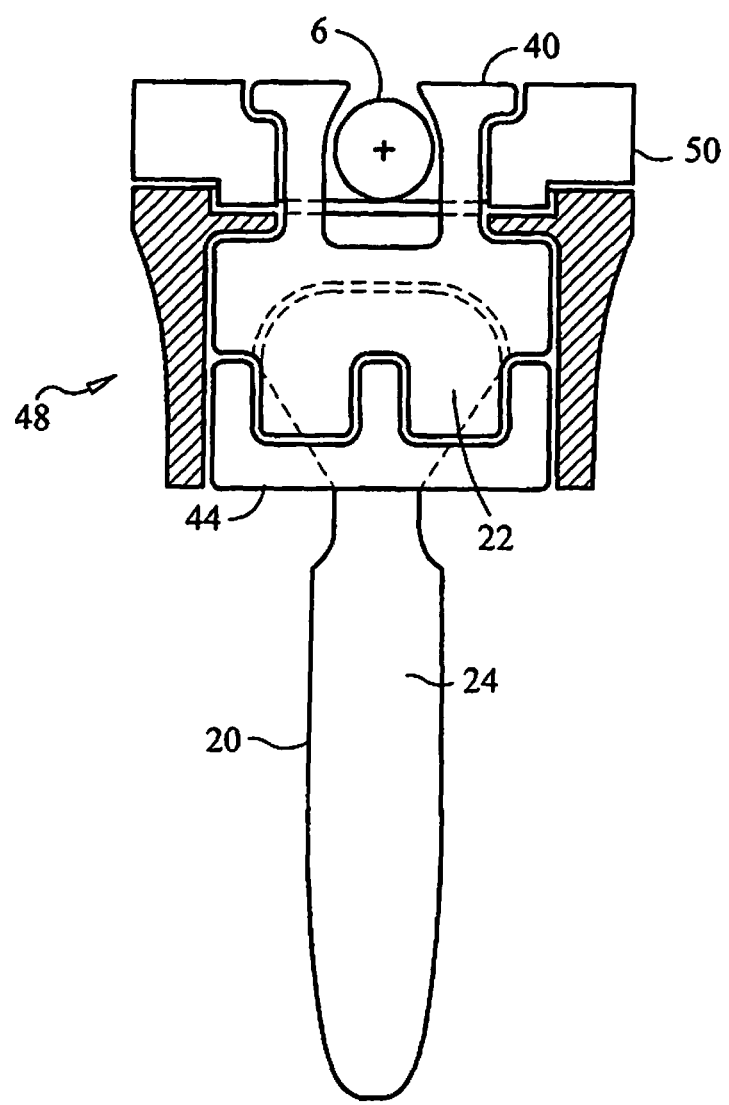
FIG. 9 is a partial cross-sectional view of another embodiment of a variable angle fastener.
Figure 12:
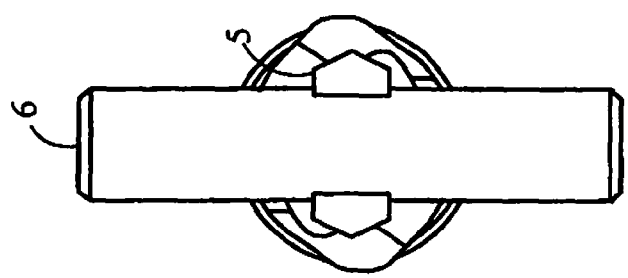
FIGS. 10-12 are additional illustrations of the variable angle fastener of FIG. 9.

FIGS. 9-12 illustrate an embodiment of the invention that does not utilize a coupling ring with ring arms applying forces to stops in order to cause the coupling element to flex or bend around the head 22. Instead, this embodiment uses a multiple piece threaded lock to clamp the coupling element to the fastener 20. For example, FIG. 9 illustrates a coupling element formed from a lower clamp element 44, an upper clamp element 46, a threaded locking nut 48, and an elongated rod locking nut 50.

Figure 11:
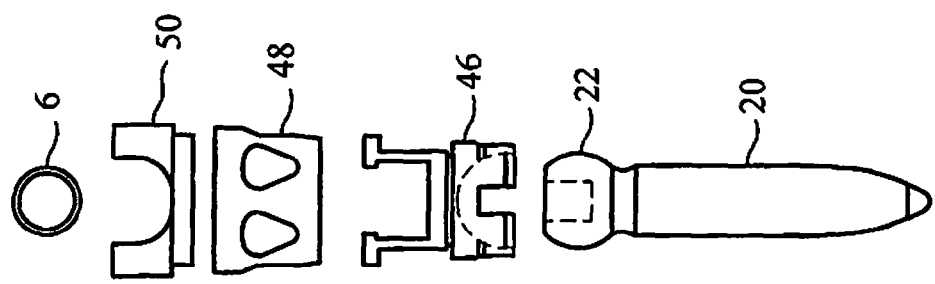

FIG. 11 illustrates the assembly of the polyaxial screw of this embodiment of the invention. During assembly, the upper clamp element 46, elongated rod locking nut 50, and threaded locking nut 48 are positioned over the head 22 of the fastener 20 that is distal to the screw shaft 24. The lower clamp element 44 then is placed onto the head 22 by passing the screw head through its open center. The lower clamp element 44 preferably has threads that engage with the threads of the threaded locking nut 48. As these threads are increasingly engaged, the upper and lower clamp elements 44 and 46 gradually clamp onto the head 22 until the coupling element is securely in place.

FIG. 9 shows that the interface between the upper and lower clamp elements may be engaged in a manner that prevents rotation of the clamp elements as the threaded locking nut is turned. In one embodiment, the upper and lower clamp elements utilize corresponding square tooth patterns on the clamping elements. Other patterns also may be used for the interconnecting surfaces, such as a sawtooth, a ratchet, or the like. The edges also may have roughened surfaces, such as a star grind, to help prevent rotation of the clamp elements, although it is more preferred that the interlocking surfaces of larger dimensions be used in order to ensure that the surfaces interconnect and resist rotation.

The elongated rod may be locked in place by turning the elongated rod locking washer or nut so that the tines of the coupling element flex or bend to grip the rod. As shown in FIG. 9, the tines may be formed on the upper clamp. In this embodiment a cap as previously described for locking the elongated rod in place may or may not be present. For example, the elongated rod locking washer may have one or more cams on its internal surface that urges the tines to bend or flex tightly around the elongated rod when the washer is turned or rotated. Preferably, turning the washer from about 5° to about 25° causes the elongated rod to be either locked or unlocked. More preferably, the washer can be turned from about 10° to about 25°. If desired, a cap may be provided to further ensure that the rod is securely held in place. A set screw may also be provided in the cap to apply additional locking forces to the elongated rod.

Figure 13:
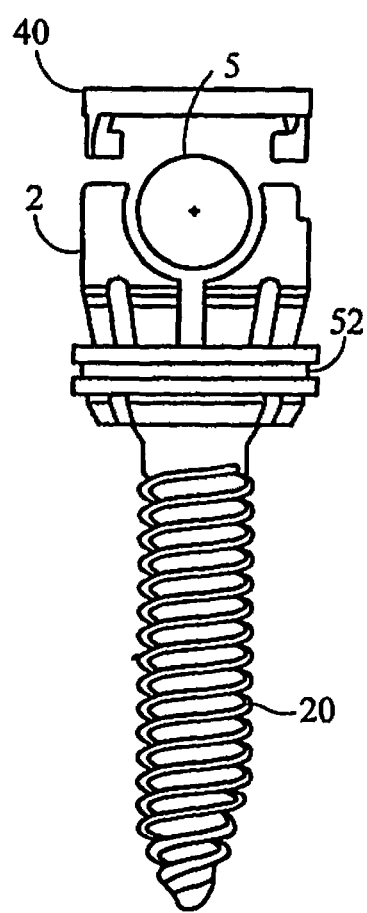
FIG. 13 illustrates another embodiment of the invention having a screw, a body, a locking ring slidably engaged with the body, and an optional cap.
Figure 14:
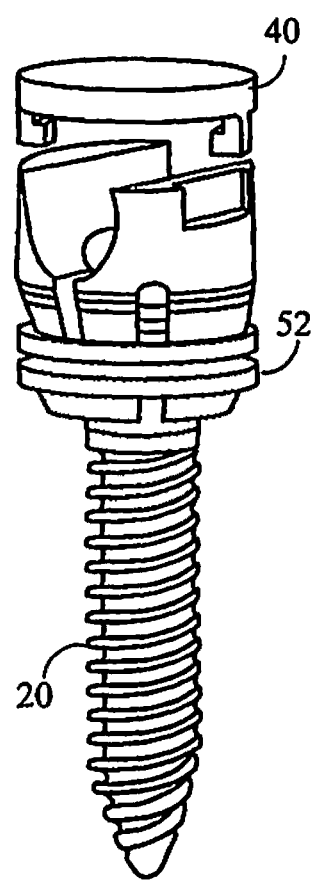
FIG. 14 illustrates an isometric view of the embodiment of FIG. 13.

FIGS. 13 and 14 illustrate another embodiment of the invention that once again uses a coupling body skirt with slots or openings formed therein. In this embodiment, the coupling body skirt may be angled by from about 5° to about 30°, and more preferably is from about 7° to about 15°. While the figures illustrate that the taper of the coupling element gradually expands the diameter of the tapered portion of the coupling body skirt 32 from the end proximate the screw shaft 24 to the upper end near the elongated rod, skilled artisans would appreciate that the taper could be inverted.

A locking ring 52 disposed around the coupling body skirt is capable of causing the coupling element to clamp securely to the fastener 20 simply by moving it in an axial direction along a tapered surface of the coupling body skirt 32. One advantage of this embodiment over the embodiments of FIGS. 9-11 is that there is no need to apply a wrench to a threaded locking nut. Additionally, in this embodiment the coupling body may be formed from only two elements instead of four. Thus, this embodiment may be advantageous over other embodiments at least for it simplicity of operation and design.

In operation, once the coupling element is in a desired position, the locking ring 52 may be moved vertically along the axis of the coupling body skirt. As the ring is moved, it engages with and compresses the tapered region of the skirt, which in turn causes the skirt to flex and bend toward the head 22. Although not shown, a second ring may be provided on the skirt to help independently lock the elongated rod to the coupling body. This can be accomplished, for instance, by providing tines that reach above the elongated rod after the rod has been positioned within a seat of the coupling element.

In much the same manner as described above for locking the coupling element 26 to the fastener 20, the second locking ring can be moved along the axis of a second tapered coupling body skirt that is configured and adapted for locking the elongated rod. It may be advantageous to configure the first and second tapered skirts and locking rings so that the direction of movement for moving one locking ring into a locked position would cause the second locking ring to move into an unlocked position if moved in the same direction. In other words, for this embodiment it may be advantageous to configure the coupling element so that locking of all components of the polyaxial screw is effected by either moving the locking rings far apart or by moving them toward each other.

Another alternative for locking the elongated rod is to use a cap 40. Any cap design for locking an elongated rod, including those already described herein, may be used to securely connect the elongated rod with the coupling element.

Figure 15:
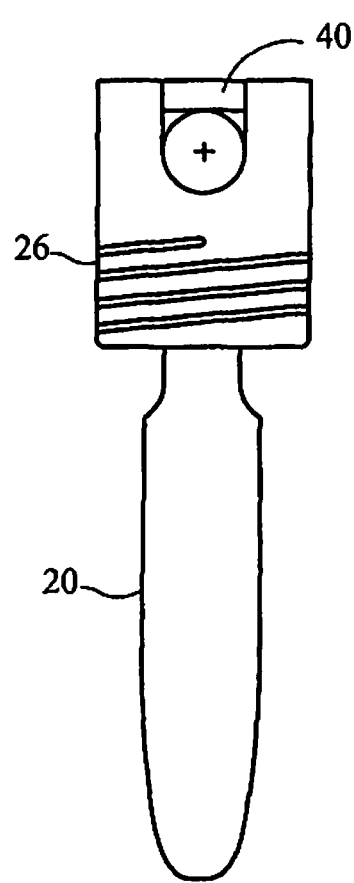
FIG. 15 illustrates another embodiment of the invention having a fastener with a flexible head configured to receive an elongated rod.
Figure 16:
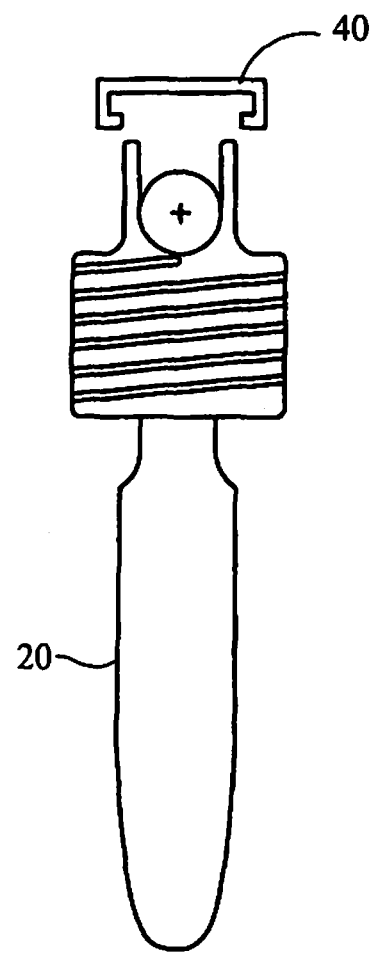
FIG. 16 illustrates a variation of the embodiment of FIG. 15.

In general, the embodiments described above may be used to establish a substantially rigid, immobilization of at least a portion of the spine. In some cases, however, it may be advantageous to use a system that allows for some flexible support for at least a portion of the spine. The embodiment illustrated in FIGS. 15 an 16 describe one aspect of the invention where the fastener 20 is capable of flexing or bending even after the components have been secured together. Although not required in order to practice the invention, in a preferred embodiment, the fastener and coupling element may be integrally formed.

The coupling element may have one or more slits or openings that provide limited range of flexibility. For instance, the coupling elements may be configured to permit from about 2° to about 7° of flex. To provide this flexibility, the coupling element may be formed from one or more slits or openings formed in its surface. In one embodiment, the slits or openings in the coupling element are generally helical in shape. Other flexible constructions also may be used. For instance, U.S. patent application Ser. No. 10/443,755, filed May 23, 2003, and which is incorporated herein in its entirety, provides several methods and constructions for a flexible coupling element that may be used in the present invention. In addition, U.S. patent application Ser. No. 10/762,533, filed Jan. 23, 2004 and which is also incorporated by reference in its entirety, provides additional methods and constructions that may be used with the present invention.

A seat for receiving the elongated rod may also be integrally formed into the fastener, although once again such a construction is not required in order to practice the invention. The seat may be formed from a plurality of tines in the manner previously described, or alternatively may have a threaded surface in which a locking cap 54 is placed over the rod. As the locking cap is turned, its lower surface presses against the upper surface of the elongated rod until the rod is securely held in place.

Figure 18:
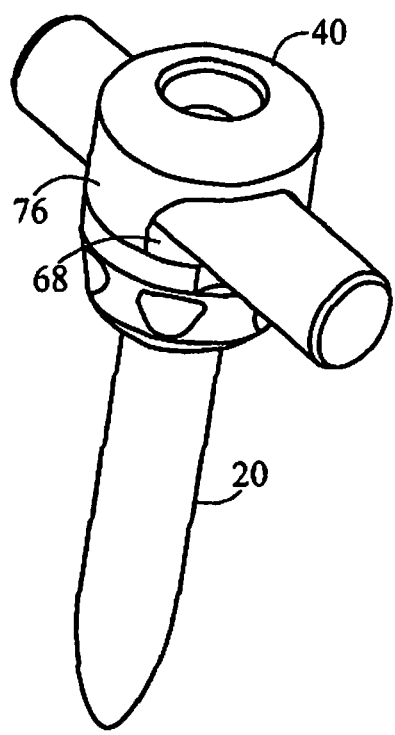
FIG. 18 illustrates an isometric view of the embodiment of FIG. 17 when assembled.
Figure 19:
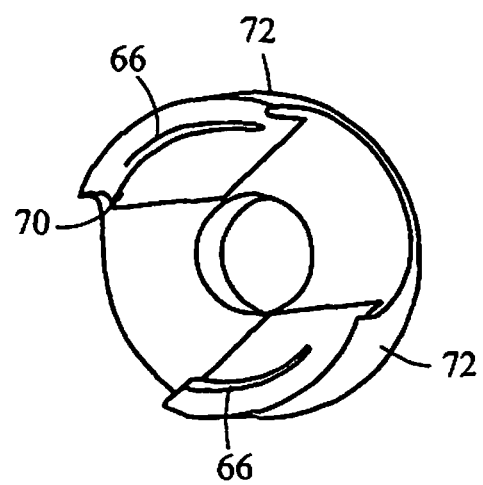
FIG. 19 illustrates an isometric view of a cap of the embodiment of FIG. 17.

FIGS. 17-19 illustrate another embodiment of the invention using a multiple piece threaded locking nut to clamp the coupling element 26 to the fastener 20. As shown in FIG. 17, the coupling element 26 comprises a lower clamp element 44, an upper clamp element 46, a threaded locking nut 48. The upper and lower clamp elements 44 and 46 have interconnecting edges that, when joined, help prevent rotation of one clamp element with respect to the other. As shown in FIG. 17, for example, the interconnected edges of the upper and lower clamp elements 44 and 46 may have an interconnecting pattern of teeth. Skilled artisans would recognize that other interconnecting edge patterns also may be used to help prevent rotation of the clamp elements with respect to each other.

A portion of the lower clamp element 44 is threaded on its outer surface in order to receive corresponding threads on the inner surface of the threaded locking nut 48. Tightening of the threaded locking nut 48 causes the upper and lower clamp elements 44 and 46 to move towards each other in order to lock the coupling body 30 onto the head 22.

The upper and lower clamp elements 44 and 46 have seating surfaces that conform to a portion of the curved surface of the fastener head 22. Preferably, the radius of curvature of the rounded or semi-spherical portion of the head 22 is the substantially the same as the radius of curvature for the seating surfaces of the upper and lower clamp elements. Once the clamp elements have fully contacted the head 22, however, a gap or opening may remain between the upper most or lower most regions of the interconnecting edges. For instance, the space between the uppermost edge of an upwardly extending square tongue of the lower clamping element 44 and the uppermost edge of a corresponding square groove of the upper clamping element 46 may be from about 1 mm to about 5 mm in height.

While the upper clamp element 46 has a lower edge that interconnects with the edge of the lower clamp, it also has an upper edge on the distal end from the interconnecting edge that engages with other elements of the coupling body to form a seat that receives the elongated rod. In particular, the distal end of the upper clamp element 46 extends above the threaded locking nut 48 and through an aperture formed in a rod seating and locking element 58 disposed above the threaded locking nut 48. The rod seating and locking element 58 has a curved seating surface that receives the elongated rod, but also is configured with a recess 60 to receive the distal end of the upper clamp element 46.

In particular, the distal end of the upper clamp 46 has two or more wings 56 that extend radially outward from the distal end of the clamp. As shown in FIG. 17, the threaded locking nut 48 and rod seating and locking element 58 are notched to permit the wings 56 to pass through them when the wings are aligned with the notches. Once the wings are disposed above the seating surface of the rod seating and locking element 58, either the upper clamp 46 or the locking element 58 may be rotated until the recess 60 is aligned with the wings 56. The wings 56 are then placed within the recess 60 to form the seating surface on which the elongated rod will be placed.

Once the elongated rod is positioned over the seating surface of the locking element 58 and the wings 56 of the upper clamping element 46, a locking cap 62 may be joined with the locking element 58 to securely connect the coupling element 26 to the rod. The manner in which the cap 62 and locking element 58 apply a locking force on the elongated rod may vary. In one embodiment, the locking cap is configured to apply a downward force on the elongated rod as it is joined with the locking element 58. As shown in FIG. 17, the locking element 58 may have one or more tabs that engage with the cap 62 to move the cap downward upon the rod.

Referring to FIG. 19, the cap may have a curved ridge or tooth 66 extending along a portion of the circumference of the cap on its interior surface. The length of the curved ridge 66 may be determined in part upon the amount or rotation the cap will undergo when moving from an unlocked position to a locked position over the elongated rod. For instance, one or more curved ridges may extend from about 3° to about 30° of the cap, and more preferably extends from about 10° to about 20°. The curved ridge 66 engages with the underside of the tab 64.

Either the curved ridge 66, the tab 64, or both may be configured to create a cammed surface that forces the cap downward as it is rotated toward a locked position. The tab and ridge also may be configured with one or more detents and recesses that are capable of providing a tactile or audible signal to the physician, such as click that may-be felt or heard, of when the cap has reached its locked position. The detents and recesses also may assist in maintaining the cap in its locked position.

Referring to FIG. 17, in a preferred embodiment the locking element 58 has an outer surface 68 below the tabs 64 that is generally cylindrical in shape. The cap 62 likewise has a corresponding generally cylindrical surface 70 of similar diameter. When the cap is placed over the locking element, these two surfaces may help maintain radial positioning of the cap 62 relative to the locking element 58 as the cap is turned toward a locking position.

In one alternative embodiment, the locking element 58 and cap 62 may be configured compress a portion of the seating surface around the rod to lock it in place in a manner similar to FIGS. 9 and 14. Thus, this alternative embodiment may involve modifying the generally cylindrical surfaces 68 and 70 to create a cammed surface that applied radially inward forces upon a portion of the locking element. As the cap 62 is rotated toward a locking position, the radial forces increase and cause a portion of the locking element 58 to flex, bend, and compress the elongate rod.

As shown in FIGS. 17-19, the cap of this embodiment may have a sidewall 72 that extends from the top of the cap 62 toward the screw shaft 24. Preferably the cap sidewall 72 terminates near a lip or base of the locking element 58, and both elements are configured to have approximately the same outer diameter. In order to place the cap over the elongated rod the sidewalls 72 may have cutouts or notches 74 that permit the rod to extend through the sidewall 72 when the cap is placed over the locking element 58 in either a locked or unlocked position. Thus, the length of the cutouts or notches generally correspond to the amount of rotation needed to move the cap into or out of a locked position. The cutouts 74 also may be slightly larger than needed to rotate the cap 62 in order to allow for possible tolerances in the design of the cap 62, the locking element 58, and the rod. For instance, the cutouts 74 may permit from about 1° to about 5° of additional rotation than needed to lock or unlock the cap 62.

Figure 8:
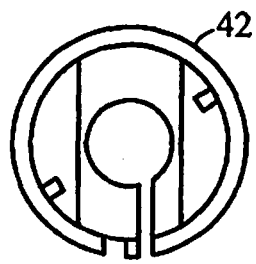
FIG. 8 is a top view of the 1-piece body of the embodiment of FIG. 5.
Figure 20:
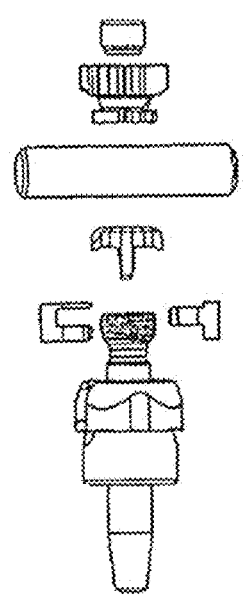
FIG. 20 is an exploded side view of one embodiment of the present invention.
Figure 21:
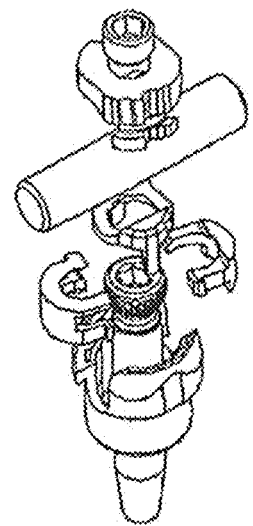
FIG. 21 is an exploded isometric view of the embodiment of the present invention of FIG. 20.
Figure 22:
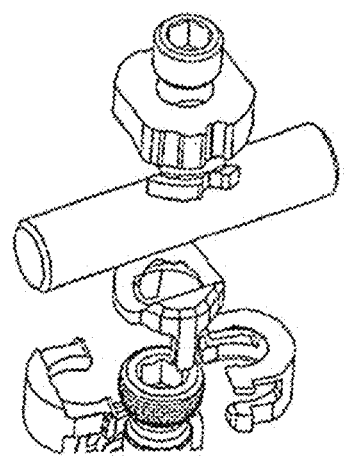
FIG. 22 is a closer exploded isometric view of a portion of the invention of FIG. 17.
Figure 23:
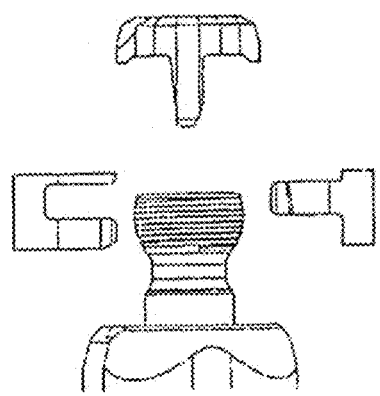
FIG. 23 is a closer exploded side view of a portion of the invention of FIG. 17.

Several of the features or elements of the various embodiments described herein may be modified and/or used with other embodiments without departing from the spirit and scope of the invention. FIGS. 20-25 illustrate yet another embodiment of the invention that uses several features or elements described above. FIGS. 20-24 show how the components of this embodiment may be configured, arranged, and assembled. As shown in FIG. 21, for instance, the coupling element 26 may be formed of a coupling body and coupling ring. The coupling body may have one, two, or more coupling body components with at lest one, preferably two, slits or openings extending substantially, if not completely, along the axial length of the coupling body. The slits or openings need not be straight, but rather may be defined by the terminating edges of material on the coupling body components 42. FIGS. 20, 23 and 24 illustrate that the terminating edges of the coupling body components may be configured with a tongue and groove configuration. Likewise, a single coupling body component such as shown in FIGS. 7 and 8 may be used in place of a plurality of coupling body components.

Likewise, one terminating edge may define a first substantially horizontal protrusion disposed above a second substantially horizontal protrusion defined by the opposing terminating edge so that the first and second protrusions are substantially layered or sandwiched together. Stops may be disposed on the coupling body components near each slit. At least one stop may be provided on opposite sides of the slit or opening. Thus, where the illustrated example uses two coupling body components, there are at least two stops on both components. The coupling body components may be disposed around the rounded fastener head. Subsequently, a ring may be pressed or lowered downward over the coupling body components. As the ring is lowered, one or more arms slidingly engage with the stops. Further downward movement of the ring and arms may then cause the coupling body components to securely grip the fastener head. FIG. 24 illustrates that the arm may define a wedge shape that pushes the stops on the coupling body components further apart from each other, which in turn causes the components to apply greater gripping force upon the fastener head.

Skilled artisans would appreciate, however, that other configurations of stops may also be used to securely grip the fastener head, including any of the other configurations previously described above. For instance, the configurations illustrated in FIGS. 1 and 6B-E may also be utilized to push the stops closer together in order to increase the gripping forces applied to the fastener head.

Turning to FIG. 24, the coupling body components may be configured to join together to grip the screw head. In this embodiment, a first coupling body component may have two prongs or arms on each side that extend outward to define a recess therebetween. The second coupling body component may then be configured with one arm on each side that corresponds generally to the recesses formed in the first component.

The interior surfaces of the coupling body components may be roughened or textured to more securely grip the screw head. As shown, the interior surfaces may be textured with a plurality of grooves or circular cuts. The interior surfaces of both components may have similar textured formed thereon, or alternatively may have different textures or texture orientations. For instance, the grooves or circular cuts on one interior surface may be oriented in one direction, such as being directed generally horizontally, while grooves or cuts on a second interior surface may be oriented in a different direction, such as vertically, so that the angle formed between the direction of the grooves or cuts of the first surface and the direction of the grooves or cuts of the second surface is from about 60° to about 90°. In one embodiment, the gripping pressure applied to the fastener head causes the raised portions of the surfaces having grooves to deform or cut into an opposing grooved surface, thereby further resisting unintended movement or repositioning of the components. Additionally, helical grooves may be provided on either a portion of the fastener head, on a gripping surface of one or more coupling elements, or both.

Once the coupling body component are place around the screw head, ring arm 36 may be place over the coupling element so that downward extending arms of the ring arm begin to engage with the stops to hold the coupling body components onto the screw head. In addition, the coupling body components and screw head may be lowered into the skirt. Turning to FIG. 25, the lower portion of the skirt may have a lip or retaining ring that is capable of supporting the fastener and assembled components disposed around its head. The lip may be a unitary surface extending inward around the entirety of the perimeter of the lower portion of the skirt, or alternatively may be formed of a plurality of tabs or protrusions that cooperate to prevent the assembled components from passing through the lower end of the skirt. The portion of the fastener head and assembly that rests against the lip may be shaped or configured to distribute the axial loading placed on the lip in substantially equal portions. In one embodiment, the surface of the lip that contacts the assembly is substantially flat and resides in a plane that is perpendicular to the longitudinal axis of the skirt. The shape of the contacting surface of the lip may have other shapes as well, such as a frustoconical shape, a partially spherical shape, a sawtooth or ridged shape such as illustrated in FIG. 9, or the like.

Above the lip, the skirt has a recess formed therein where the assembly may be placed. The ring arm may then be disposed over the assembly in the manner described above. The ring arm is configured with a curved seating surface on its upper side that is shaped to receive an elongate rod. The skirt also has two openings or slots on its upper side for receiving the elongate rod.

As the rod is fitted through the opening or slots on the skirt and pressed on the ring arm seating surface, the ring arm may be urged further down, thereby causing the coupling element to close further upon the screw head. The forces applied on the screw head, however, may not yet fully prevent the skirt and assembly from being rotated, moved, or adjusted. A cap may then be lowered onto the skirt over the rod. As shown in FIG. 25, the cap may have two enlarged openings or slots that are wider than the opening of the skirt and wider than the diameter of an elongated rod that may be placed in the skirt. This embodiment permits the cap to be turned or rotated without the sidewalls of the openings or slots from being obstructed by the rod. Preferably, the openings or slots are configured to permit from about 5° to about 90° of rotation of the cap, or alternatively permit from about 15° to about 60° of rotation of the cap. In yet another embodiment, the openings or slots in the cap are configured to permit from about 20° to about 40° of rotation of the cap without being obstructed by the rod.

When the cap is turned to a first position, it engages with the skirt to prevent its inadvertent removal. In this position, the rod may remain free to be moved or slide through the openings of the skirt and cap, and the skirt may still be adjusted or moved relative to the screw or fastener. As the cap is turned further to a second position, however, a cam or inclined surface on the upper portion of the enlarged openings or slots may urge the rod further downward onto the ring arm, thereby causing the ring arm and coupling body components to securely grip the fastener head so that the skirt can no longer move relative to the screw or fastener. As mentioned above, the locking of the coupling body components in this manner may not also cause the cap to fully lock the elongated rod to the skirt. In fact, once the coupling body is locked onto the fastener head, the cap may be loosened and the elongated rod repositioned without inadvertently causing the coupling body to become unlocked from the fastener head.

Alternatively, the cap may be urged further down into the skirt as it is turned toward the second, locking position. As the cap is lowered, the upper portion of the enlarged opening or slot, which may or may not have a cam or incline, will press the rod against the seat of the ring arm. For instance, the cap and skirt may be configured with threads that draw the cap into the skirt when it is turned in one direction and releases the cap from the skirt when turned in the opposite direction.

Preferably, the skirt and/or cap are configured to provide a tactile feel or audible click when the cap reaches either the first or second position, or both positions. One advantage of this is that the physician will receive confirmation that the assembly is in a desired position. In addition, the cap and skirt may be configured with one or more detents or similar mechanisms to help prevent the cap from inadvertently backing out of either the first or second positions.

While the skirt and fastener may be fixed in position relative to each other once the cap is in the second position, the rod may still be capable of sliding through the openings of the skirt and cap. The cap may be configured with an aperture disposed on its upper surface where a set screw may be utilized to securely hold the rod in place once it is in its desired position.

FIGS. 26-29 illustrate yet another embodiment of the invention that uses several features or elements described above. FIGS. 26-29 show how the components of this embodiment may be configured, arranged, and assembled. In this particular embodiment, a coupling element comprised of coupling body components 110 and a coupling wedge 120 is used to grip the fastener 130.

Figure 26:
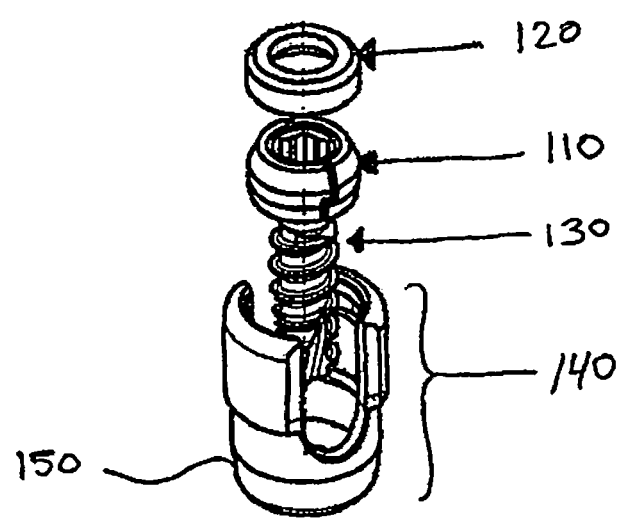
FIG. 26 illustrates an isometric view of another embodiment of the present invention.

As shown in FIG. 26, the coupling element may be formed of a coupling body 140, coupling body components 110, and coupling wedge 120. In this embodiment, the coupling body components 110 are capable of gripping or tightening around the fastener head as a result of any downward force imparted upon the coupling wedge 120. The coupling body 140 is comprised of a top and bottom portion, wherein the bottom portion comprises a skirt or inner surface portion 150 of the coupling body that is configured to receive both the coupling body components 110 and coupling wedge 120. One advantage of this present embodiment is that the coupling element is of a simple construction, is easy to install, and allows for the precise placement and adjustment of the elongated rod in relation to the inserted fastener.

As shown in FIG. 26, during assembly, the coupling body components 110 are placed around the head of a fastener 130. The coupling wedge 120 is placed above the coupling body components 110. The assembled parts may then be inserted into the coupling body 140. As a downward force is applied to the coupling wedge 120, the coupling wedge 120 interacts with the coupling body components 110 and the inner surface portion 150 of the coupling body 140 to cause the coupling body components 110 to tighten around the fastener head, locking the coupling element in place in relation to the fastener 130.

Figure 29:
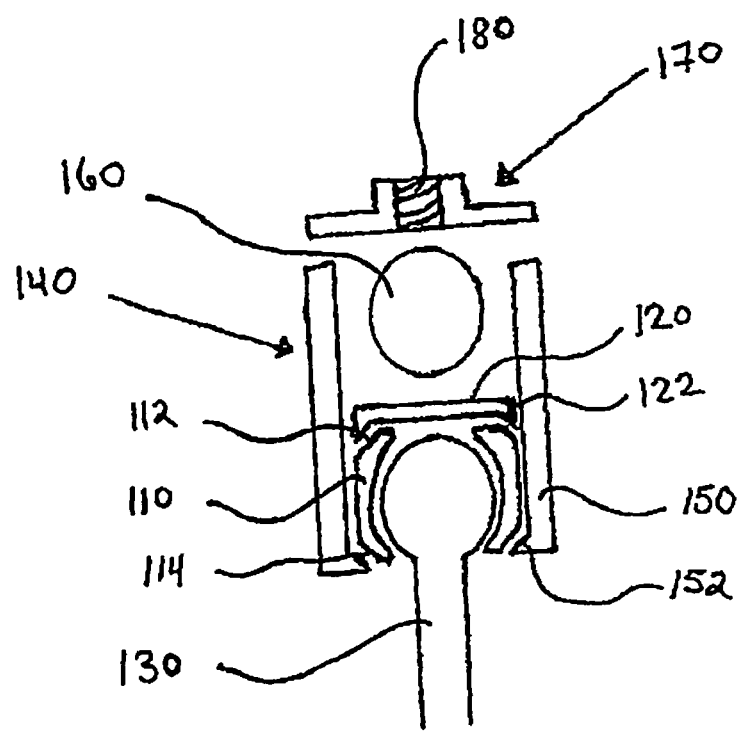
FIG. 29 is an exploded cross sectional view of the embodiment of FIG. 26.

As shown in FIG. 26, the coupling element may have one, two, or more coupling body components 110 with at least one, preferably two, slits or openings extending substantially, if not completely, along the axial length of the coupling body. As described previously, the slits or openings need not be straight, but rather may be defined by the terminating edges of material on the coupling body components 110. As opposed to previous embodiments however, the coupling body components 110 of the present embodiment do not contain protrusions, stops, or other engagable material as described above. Rather, in this particular embodiment and as shown in FIG. 26 and FIG. 29, the coupling body components 110 are substantially cylindrical in shape and may be designed with a an upper surface 112 and lower surface 114 that is tapered or of a truncated conical shape. The upper and lower surface 112, 114 of the coupling body components 110 are designed to interact with the coupling wedge 120 and inner surface portion 150 such that any downward force applied to the coupling wedge 120, causes the coupling body components 110 to tighten around the fastener head.

In one embodiment, the interior surfaces of the coupling body components 110 may be roughened or textured to more securely grip the screw heads. As described previously, the interior surfaces may be textured with a plurality of grooves or circular cuts. The interior surfaces of the components may have similar textured surfaces or alternatively may have different textures or orientations of the textured surfaces. For example, in one embodiment the gripping pressure applied to the fastener head causes the raised portions of the surfaces having grooves to deform or cut into an opposing grooved surface, thereby further resisting unintended movement or repositioning of the components.

The coupling wedge 120 is substantially cylindrical and may contain an aperture providing access through the coupling wedge 120 to the top of the fastener head. As shown in FIG. 26 and FIG. 29, the coupling wedge 120 is ring-like and is designed to engage the upper surface 112 of the coupling body components 110. The bottom surface 122 of the coupling wedge 120 may cooperatively engage with the upper surface 112 of the coupling body components 110. For example, the coupling wedge 120 of one embodiment may be formed with a tapered bottom surface 122 or truncated conical surface. As described previously, the upper surface 112 of the coupling body components 110 has a tapered surface as well. When assembled, the bottom surface 122 of the coupling wedge 120 and the upper surface 112 of the coupling body components 110 interact such that any downward force applied to the coupling wedge 120 causes the coupling body components 110 to tighten around the fastener head. This gripping force imparted to the fastener head results from the interaction of the coupling wedge 120 and coupling body components 110. While in this particular embodiment the bottom surface 122 of the coupling wedge 120 and upper surface 112 of the coupling body components 110 are described as tapered or truncated conical surfaces, it will be apparent to one of ordinary skill in the art that surfaces of the interacting components may be altered, modified, or changed so long as any downward force on the coupling wedge 120 imparts a force to the coupling body components 110 causing or urging the coupling body components 110 to tighten around or grip the fastener head.

Prior to imparting any downward force onto the coupling wedge 120, the coupling body components 110 and coupling wedge 120 are placed around the fastener head. This assembly is then lowered into the coupling body 140. Turning to FIG. 29, the lower portion of the coupling body 140 is comprised of a inner surface portion 150 that may have a lip 152 or retaining ring that is capable of supporting the fastener and assembled components disposed around its head. As described previously, the lip 152 may be a unitary surface extending inward around the entirety of the perimeter of the lower portion of the inner surface portion 150, or alternatively may be formed of a plurality of tabs or protrusions that cooperate to prevent the assembled components from passing through the lower end of the inner surface portion 150. Additionally, the lower surfaces 114 of the coupling body components may also be formed with a tapered edge or truncated conical surface. The degree to which the edge is tapered can vary but should be of a degree sufficient to prevent the coupling body components and head of the fastener from slipping through the bottom of the inner surface portion when assembled. In this embodiment, the lip 152 of the lower portion of the inner surface portion cooperatively engages the lower surface 114 of the coupling body components 110 such that when a downward force is applied to the assembled components, the interaction between the lower portion of the inner surface portion 150 and lower surfaces 114 of the coupling body components 110 causes the coupling body components 110 to tighten or grip the fastener head. Even where the lip 152 of the inner surface portion 150 does not contain a surface designed to specifically match the lower surface 114 of the coupling body components 110, any downward force applied to the assembled components may still provide for the translation of force perpendicular to the applied downward force, which in turn tightens or urges the coupling body components 110 to tighten around a fastener head. In one embodiment, the lip of the inner surface portion may be an inwardly inclined surface from anywhere greater than 1°. For example, in FIG. 28, the lower portion of the inner surface portion is in inwardly inclined surface. The incline is configured or designed so that the fastener head will not slip through the inner surface portion and coupling body component assembly.

When assembled, the interaction between the coupling wedge 120, inner surface portion lip 152, and coupling body components 110 results in the tightening of the coupling body components 110 around the fastener head. The coupling element when assembled and installed, creates a substantially rigid structure in a fixed position, i.e., the coupling element is locked to the fastener 130.

Figure 27:
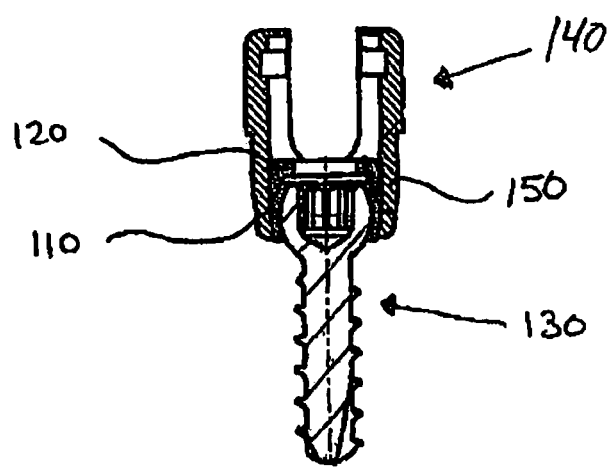
FIG. 27 is an cross section view of the assembled embodiment of FIG. 26.
Figure 28:
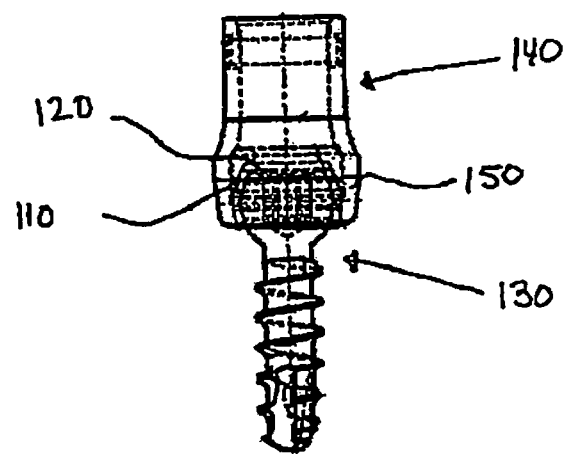
FIG. 28 is a side view of the assembled embodiment of FIG. 26.

As described in previous embodiments and with reference to FIGS. 26, 27, and 29, the coupling body 140 is configured and adapted to receive an elongated rod 160 on an upper end opposite the end of the coupling body configured with the coupling body skirt 150. Preferably, this portion of the coupling body 140 is configured with a U-shaped or wedge shaped seat against which the elongate rod will be locked. Substantially rigid tines or wedges extend upward from the seat for the rod, which are configured with slots or detents that receive a cap 170. The upper portion of the coupling body 140 is also configured to permit the elongated rod 160 to exert force upon the coupling wedge 120. The coupling wedge 120 may be configured to receive the elongated rod 160 or may not. But in either case, the design of the upper portion of the coupling body 140 must allow for the elongate rod 160 to exert a downward force upon the coupling wedge 120 in order for the coupling wedge 120 to transmit that force to the coupling body components 110.

The cap 170, such as illustrated in FIG. 29, may have corresponding protrusions or slots that permit the cap 170 to engage with and rotate with respect to the coupling body 140. In one embodiment, rotation of the cap 170 causes it to move downward and toward the elongate rod 160, thereby applying a downward force against the elongate rod 160 to hold it securely in place. The downward force is transmitted through the elongate rod 160 to the coupling wedge 120, which in turn transmits the force to the coupling body components 110. As a result of this design, the coupling element and elongate rod may be locked in place.

In an alternative embodiment as described previously, the tines or wedges of the coupling body that extend upward from the seat for the rod may be flexible so that they bend or flex around the rod as the cap is turned toward a locking position. For instance, either the cap, the tines or wedges, or both may be configured to have a tapered or ramped surface that causes gradually increasing radial interference with the cap and coupling element as the cap is rotated. As the radial forces resulting from this interference increases, the tines or wedges may bend or flex radially inward and press against the elongate rod. One or more detents and depressions may be placed on either the cap or the coupling body to hold the cap in a locked position by engaging with each other at a desired cap position. Rotation of the cap in the opposite direction likewise causes the elongated rod to become unlocked.

In an alternative embodiment, the cap 170 may contain a set screw 180 disposed in the cap 170. As described previously and as shown in FIG. 29, the set screw 180 disposed in the cap 170 may then apply additional downward pressure on the elongate rod 160 to hold it firmly in position. In addition, the downward pressure applied by the set screw 180 may be transferred through the elongate rod 160 onto the coupling wedge 120 and coupling body components 110 thus locking the coupling element to the fastener head.

In yet another embodiment, a cap 200 is provided that allows the user to easily insert the cap into the coupling body. For example, with reference to FIGS. 30-32s, cap 200 is provided that may be placed within the coupling body 210. In this embodiment, cap 200 is cylindrical in shape and generally matches the shape of coupling body 210. The cap 200 is configured to fit substantially within the interior side walls of the coupling body 210. While in the present invention, both the cap 200 and coupling body 210 are of substantially cylindrical shape, alternative designs and shapes may be used.

Figure 30:
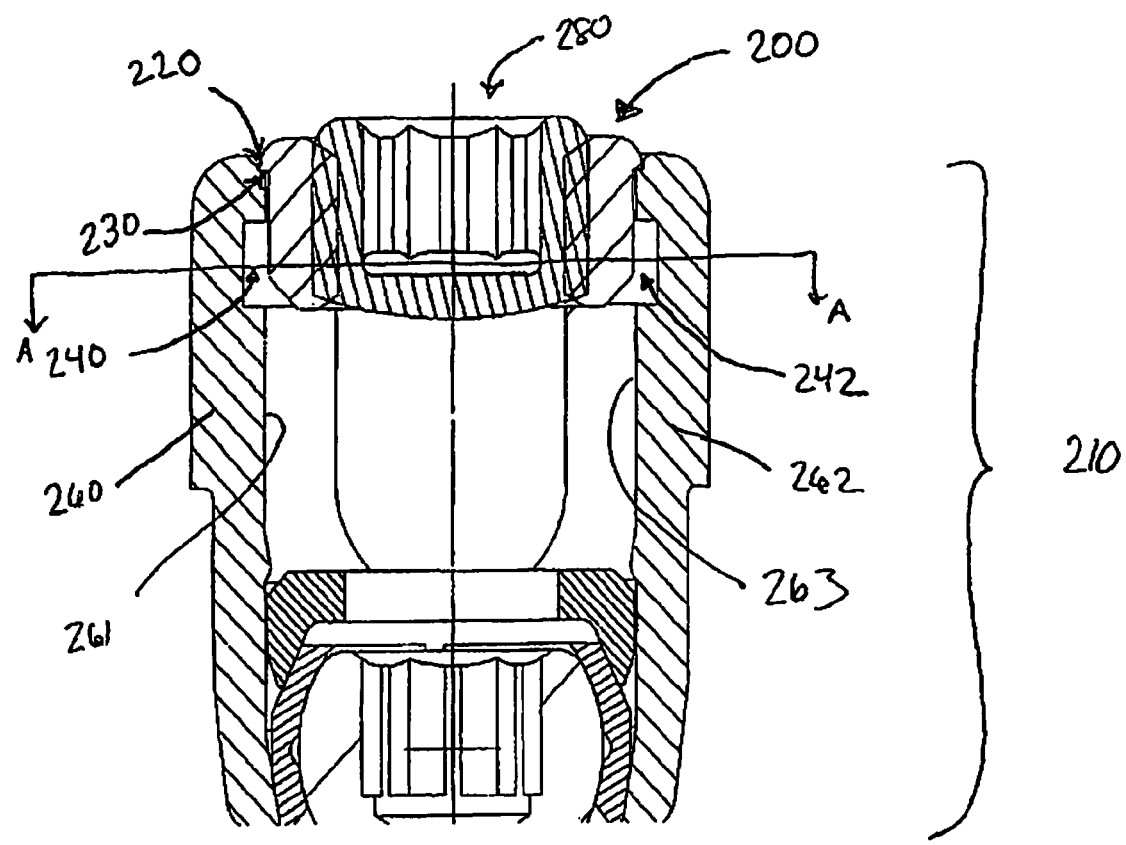
FIG. 30 is a partial cross sectional view of an embodiment of the present invention; \
Figure 31:
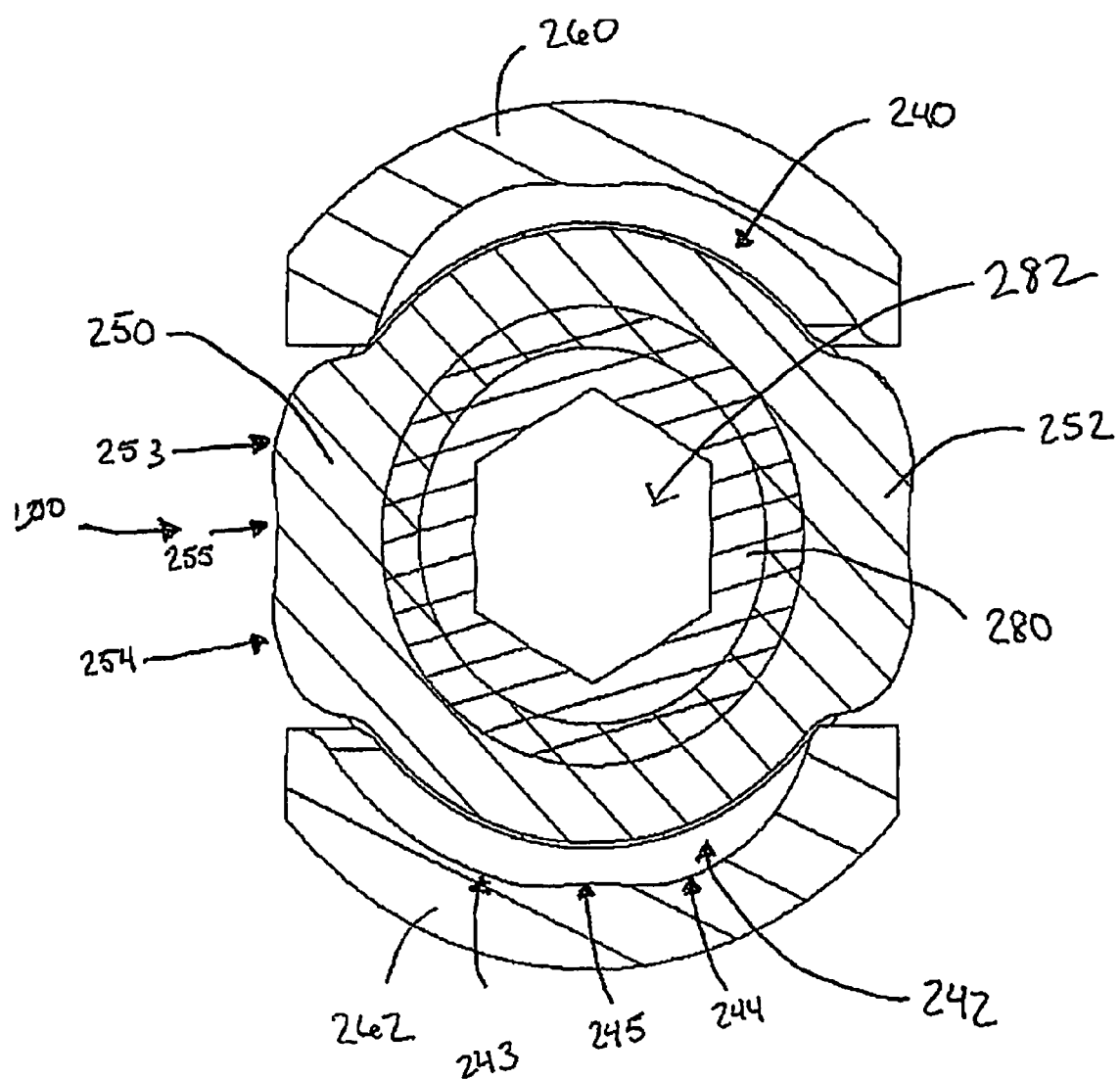
FIG. 31 is a cross sectional top view of an embodiment of the present invention.
Figure 32:
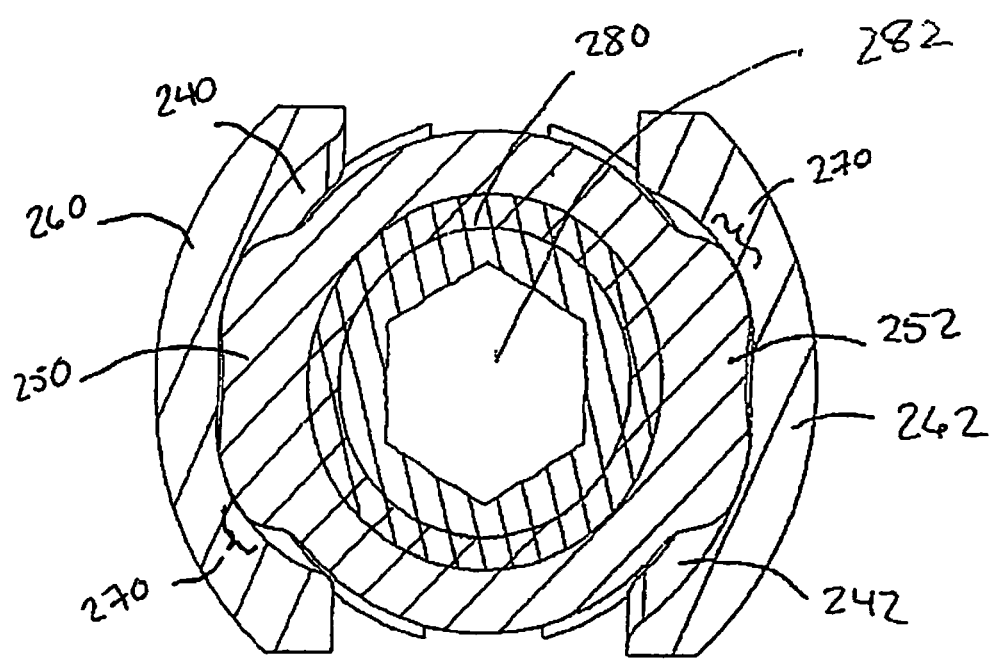
FIG. 32 is a cross sectional top view of an embodiment of the present invention.

In the embodiment of the FIGS. 30-32, cap 200 contains a lip or rim 220 around the exterior circumference of the top or upper portion of cap 200. Lip 220 is configured to engage the coupling body 210. The coupling body may similarly contain a groove 230 disposed about the interior surface of the coupling body to interact with the lip 220. The lip and groove cap design of the present embodiment prevents cap 200 from traveling in the longitudinal direction beyond a predetermined position of the coupling body 210. In this regard, the cap cannot fall into the coupling body. Without the rim or lip design of the present embodiment, a cap that can fit within the interior of the coupling body may impart downward force on the elongate rod during insertion of the cap at an undesirable moment. In addition, in instances where the elongate rod is slipped into the coupling body along a latitudinal plane, the present design allows the user to insert the cap prior to positioning or insertion of the elongate rod because the lip or rim of the cap will prevent the cap from falling into the coupling body and obstructing the space that is to be occupied by the elongate rod. Another advantage associated with the lip and groove design is that the cap is self-centering. Another advantage of the present embodiment is that the cap will not interfere with the elongate rod in a locked position. Because the cap resides within the coupling body and remains above the elongate rod, the cap does not require cutouts to allow the cap to rotate into a locked position as described previously.

In an alternate embodiment, the coupling body 210 may be designed with one or more channels 240, 242 that are configured to receive protrusions 250, 252 on the cap 200. Referring to FIGS. 30-32, the coupling body 210 is configured with channels 240, 242 along the interior side walls of the coupling body 210. For example, in one embodiment the coupling body 210 is comprised of substantially rigid tines 260, 262 that extend upward from the seat for the elongate rod and each tine includes an interior side wall 261, 263, respectively. Channels 240, 242 are formed on the interior side walls 261, 263 of the upwardly extending tines 260, 262. The channels 240, 242 are configured to receive protrusions 250, 252 of cap 200.

In the present embodiment, the cap 200 contains tabs or protrusions 250, 252 that extend radially outward from the outer circumference of the main cap body. The protrusions 250, 252 may be integrally formed with the cap 200 or may not be. The protrusions 250, 252 of the cap 200 are designed so that upon insertion of the cap 200 into the coupling body 210, the protrusions 250, 252 will not interfere with the tines or wedges 260, 262 of the coupling body 210. As seen in FIGS. 31 and 32, the size of the protrusions are of a dimension that allows the cap to be inserted into the coupling body. As seen in FIG. 31, cap 200 is shown in a first position wherein the protrusions 250, 252 are configured to initially fall within the portion of the coupling body 210 that receives the elongate rod, i.e., the openings between the two upwardly extending arms or tines 260, 262. As described previously, in some embodiments the lip or rim 220 will position the cap 200 at a predetermined location within the coupling body 210. In the embodiment containing a lip or rim 220, after placement of cap 200 into coupling body 210 the protrusions 250, 252 will lie in the same latitudinal plane as the interior channels 240, 242 of the coupling body. To lock the cap into position, the cap is rotated to a second position, as shown in FIG. 32. Upon rotation of the cap, the protrusions 250, 252 of the cap 200 will ride within or fit inside the interior channels 240, 242 of the coupling body. Alternatively, where no lip or rim is present on the cap, the user may position the cap by hand until the protrusions align with the channel present on the interior side walls of the coupling body. Once aligned, the cap is rotated and the protrusions of the cap ride within the interior channels of the coupling body.

The channels 240, 242 may be configured to selectively receive the protrusions 250, 252 when the cap is rotated from a particular direction. For example, as seen in FIG. 31, channel 240 is configured so that the cap may only be rotated in on direction. The channel configuration of FIG. 31 shows how the channel 240 may be formed so that the protrusion 250 may only enter the channels from one direction. Of course, if one channel is configured to receive the protrusion of the cap from one direction, the second channel must be similarly configured. In FIG. 31, the channels 240, 242 are configured to receive the protrusions 250, 252 when the cap 200 is rotated in the counter clockwise direction. Whether rotation is clockwise or counterclockwise (shown) is not important.

While a number of different design variations may be employed, it may be desirable to prevent the cap from rotating more than a discrete distance. In this regard, the protrusions may interact with the coupling body. Alternatively, one or more stops may be provided. In this alternative embodiment, the stops may be designed so that the protrusions 250, 252 of the cap 200 will contact or interfere with a portion of coupling body 210 to prevent further rotation of the cap. In one embodiment, channels 240, 242 may contain a stop configured to prevent the cap from any further rotation after insertion. Accordingly, upon insertion of the cap into the coupling body, the protrusions 250, 252 of the cap may ride within channels 240, 242 until the protrusions interact with one or more stops. The stop may be formed within the channel residing on the interior side walls of the coupling body or it may be positioned elsewhere on the coupling body. Alternative constructions may position the stop on the interior side walls of the upwardly extending tines, or alternatively, the stops may be part of the lip and groove portion of the cap and coupling body. In alternative embodiments, the configuration or design of the channel itself may act as the stop. As seen in FIGS. 31 and 32, the channels 240, 242 do not run along the entire circumferential length of the inner side walls 261, 263 of the upwardly extending tines 260, 262. Accordingly, at area 270, the protrusions 250, 252 will interfere with the interior side walls 261, 263 of the tines 260, 262 and further rotation of the cap 200 is prevented. As shown in FIGS. 31 and 32, cap 200 is capable of about 90 degrees of rotation. Alternatively, the cap may be rotatable anywhere from 180 degrees to about 5 degrees.

Figure 33:
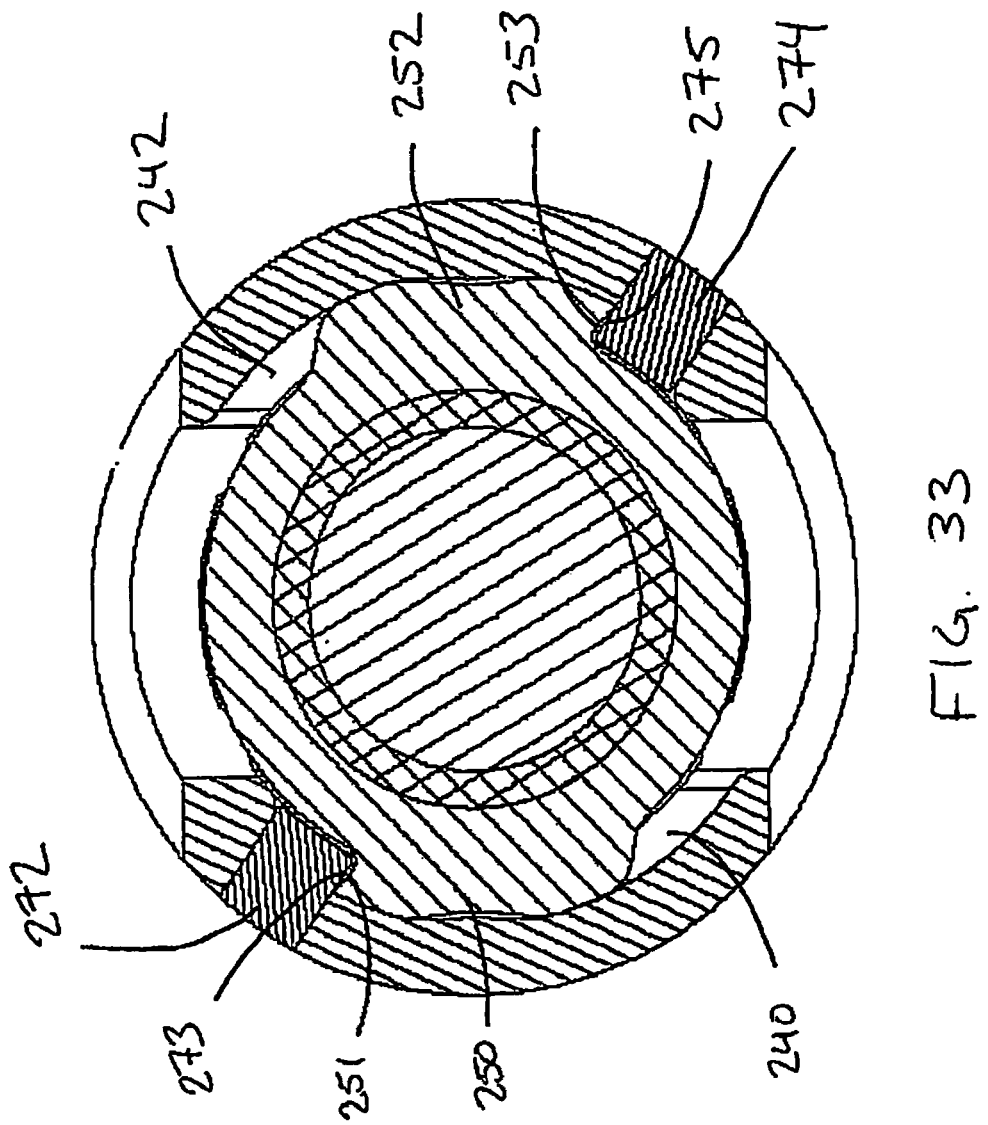
FIG. 33 is a cross sectional top view of an embodiment of the present invention.

In an alternative embodiment, for example as shown FIG. 33, the coupling body may be formed with stops 272, 274. Whether the stops are integrally formed or not with the coupling body is not important. FIG. 33 shows stops 272, 274 that are not integrally formed with the coupling body. In FIG. 33, the stops 272, 274 are press fit into the coupling body and laser welded to the coupling body or otherwise fixed in place. As seen in FIG. 33, the stops prevent the cap from rotating in a angular direction past a desired point. Depending on design considerations, it may be desirable to rotate the cap from between about 5 degrees to about 180 degrees.

As seen in FIG. 33, the stops 272, 274 are designed to protrude radially inward from the wall of the coupling body into the channels 240, 242 to create a physical barrier against which the cap protrusions 250, 252 abut. The stops 272, 274 comprise contact surfaces configured and dimensioned 273, 275 to mate or fit with the protrusions 250, 252. The protrusions 250, 252 comprise contact surfaces 251, 253 similarly configured and dimensioned to mate or fit the contact surfaces 273, 275 of the stops. In some embodiments, for example as seen in FIG. 33, the contact surfaces 273, 275 of the stops and the contact surfaces 251, 253 of the protrusions are configured to fit, cooperate, mate, or otherwise engage to prevent angular movement of the cap beyond a predetermined point.

One of the advantages of the aforementioned design of the stops and protrusions is that after rotation of the cap to its second or locked position, the contact surfaces of the stops increase the strength and effectiveness of the stop by providing a contact surface having a shape conforming to its respective contacting surface and may further help prevent the arms of the coupling body from splaying or spreading. For example, as seen in FIG. 33, the contact surfaces of the stops are flat surfaces that are perpendicular to the inner and outer circumference of the coupling body. Similarly, the contact surfaces of the protrusions may be designed or configured as flat surfaces perpendicular to the inner circumference of the coupling body to mate with or abut the flat contact surfaces of the stops. In designs where the contact surfaces of the stops and protrusions are rounded, force during rotation of the cap may cause the cap to splay or spread the arms of the coupling body. By configuring the contact surfaces of the stops and protrusions as flat surfaces, the potential for the splaying or spreading of the arms of the coupling body is significantly reduced. In alternative embodiments the contact surfaces do not necessarily have to be flat. For example, the contacting surfaces may be convex and concave or any other design so that the contact surfaces of the mating pair substantially fit, cooperate, or engage with each other. In general any configuration of the contact surfaces may be used such that there is no substantial torsional force or outward radial force imparted on the stop or coupling body as a result of the rotation of the cap and its corresponding protrusions.

Figure 34:
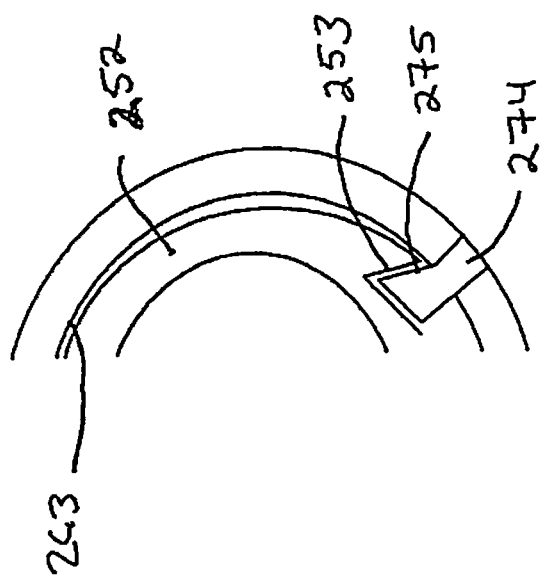
FIG. 34 is a partial cross sectional view of an embodiment of the present invention.

In an alternative embodiment, for example as shown in FIG. 34, the stops may be designed with contact surfaces at an angle less than 90 degrees with respect to the interior sidewalls of the coupling body. While only one half of the alternative embodiment is shown in FIG. 34, it should be understood that the other half of the cap design may be similarly configured. As shown in FIG. 34, the contact surface 253 of the protrusion 252 is angled with respect to the interior surface of the coupling body. Similarly, as shown in FIG. 34, the contact surface 275 of the stop 274 is angled with respect to the interior surface of the coupling body. Contact surfaces 253 and 275 are configured and adapted to mate or engage with each other. Accordingly, when the cap is rotated to a second or locked position, the mated contact surfaces 253 and 275 prevent splaying or the outward radial expansion of the arms of the coupling body. Additionally, the present configuration increases the overall structural integrity of the coupling body as well as the strength of the stop.

Figure 35:
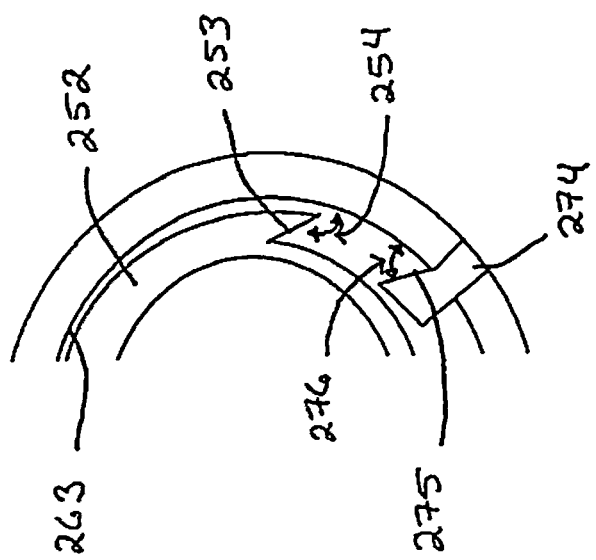
FIG. 35 is a partial cross sectional top view of an embodiment of the present invention.

As seen in FIG. 35, the contact surfaces 253 and 275 may be angled with respect to an interior surface 263 of the coupling body. In this alternative embodiment, the contact surface 253 of the stop is at an acute angle 254 with respect to the interior surface of the coupling body. In addition, the contact surface 275 of the protrusion is at an obtuse angle 276 with respect to the interior surface 263 of the coupling body. One of skill in the ordinary art would recognize that the respective angles of the contact surfaces could vary from between about 0° and 90° for the stop contact surface and from between about 90° and 180° for the protrusion contact surface. Any angle between these values would function to substantially eliminate any outward radial force that may be imparted upon the coupling body, and stops from the rotation of the cap.

Generally, protrusions 250, 252 extend radially outward from the outer circumference of the main cap body and may further be configured or adapted to create an interference or friction fit with the coupling body. As seen in FIGS. 31 and 32, the protrusions 250, 252 may be designed to create a friction or interference fit with the coupling body 210. This design allows the cap to be rotated into a locked position. As shown in FIGS. 31 and 32, each of the protrusions 250, 252 is configured with two high points 253, 254 and one low point 255 when viewed in an axial plane. Each of the channel 240, 242 of the coupling body 210 may be similarly configured with two high points 243, 244 and one low point 245 to match the low and high points of the protrusions. Accordingly, upon rotation of the cap the first high point 254 may interfere with the low point 245 of the channel. This interference may be overcome with sufficient force. Upon further rotation, the first high point 254 of the protrusion 250 will fit within the corresponding high point 244 of the channel. After rotation, the low point 255 of the protrusion 250 is aligned with and/or fits or matches the low point 245 of channel 240. In this manner, a friction fit is provided that locks cap 200 into position. Additionally, in the embodiment shown in FIGS. 31 and 32 the second high point 253 of the protrusion 250 (in conjunction with the design of the channel) generally prevents cap 200 from being rotated in the clockwise direction. Also as shown in FIGS. 31 and 32 the channel 240, 242 are configured to prevent further rotation of the cap in the counterclockwise direction once the cap has been rotated by about 90 degrees. Additionally, the cap and/or coupling body may be configured to provide a tactile feel or audible click when being rotated to a second or locked position, such as for example the position shown in FIG. 32. In alternative designs, only one of the protrusions may create an interference fit. Also, in alternative designs, the protrusions may be integral to the sidewalls of the upwardly extending tines and the channels may be formed in the body of the cap.

As described previously, cap 200 may also comprise a locking element capable of securely holding the elongate rod in a fixed position relative to the coupling body. In one embodiment, the cap 200 may have a threaded opening and the locking element may be a threaded set screw disposed within the threaded opening. As shown in FIGS. 30-32, a set screw 280 is disposed within cap 200 and may contain a hexagonal cut out 282 disposed on the upper portion of the set screw to receive a tool to rotate the set screw. In alternative embodiments, other tool interface configurations may be used. Set screw 280 is capable of applying downward force or pressure on the elongate rod to lock the elongate rod in position relative to the coupling body. In this embodiment, generally any upward force exerted on the cap as a result of the downward force imparted on the elongate rod by the set screw is counteracted by the protrusions 250, 252 of cap 200 that lie within channels 240, 242. The interaction of the protrusions with the channel counteract the upward force and a net resulting downward force is applied to the elongate rod, locking or fixing the elongate rod with respect to the coupling body.

In alternative embodiments, a polyaxial screw design is provided with improved cap designs. The cap designs are directed at providing easier installation of the cap and improved retention of the elongate rod. In some embodiments, the improved polyaxial cap designs prevent the cap from rotating out of position after it has been rotated into place. In other embodiments, the improved cap design provides for greater stability of the polyaxial screw, including preventing splaying of the arms of the coupling body of the polyaxial screw.

Figure 36:
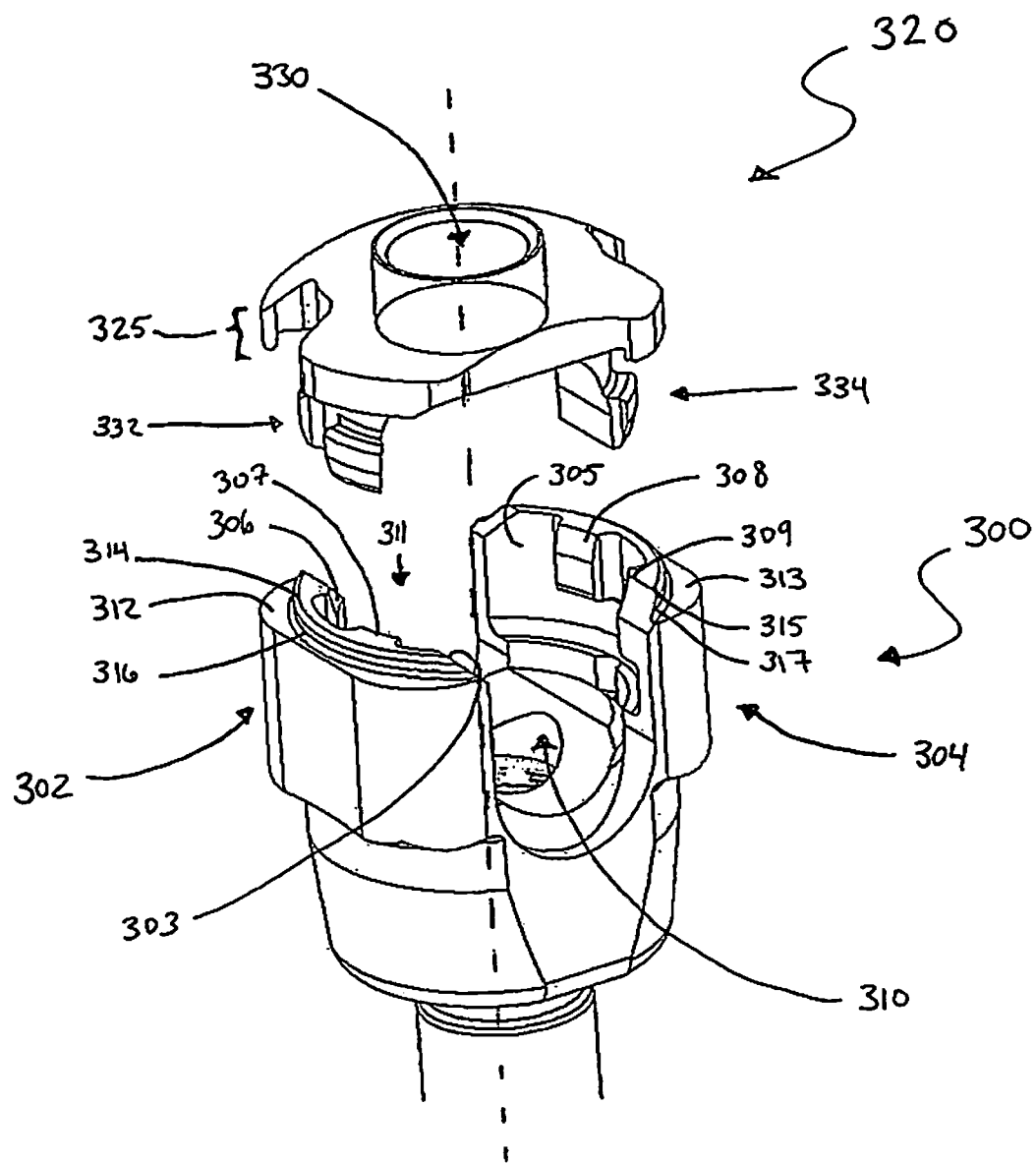
FIG. 36 is a partially exploded view of another embodiment of the present invention.
Figure 37:
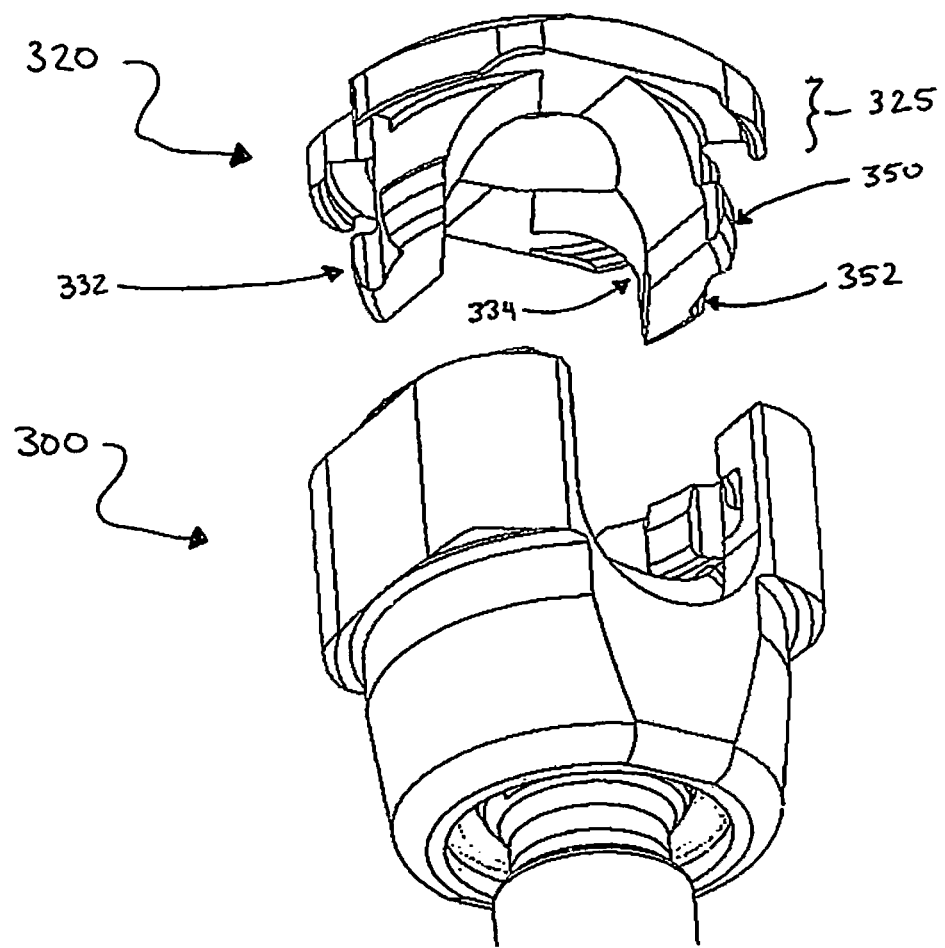
FIG. 37 is an alternate partially exploded view of FIG. 36.

For example, and with reference to FIGS. 36 and 37, an alternate polyaxial screw design is provided with a coupling body 300 and cap 320. As shown in FIGS. 36 and 37, coupling body 300 contains two upwardly extending arms 302, 304 that extend longitudinally in the proximal direction. The coupling body has two slots 310, 311 configured to receive an elongate rod. Arms 302, 304 of coupling body 300 have interior and exterior surfaces. Interior surfaces 303, 305 of arms 302, 304 respectively are configured with inwardly projecting radial protrusions 306, 307, 308, and 309. Coupling body 300 is also designed with a lip or rim that resides on the upper surface of the coupling body. As seen in FIGS. 36 and 37, each arm 302, 304 of coupling body 300 has disposed about its superior surfaces 312, 313 a partially circumferential rim 314, 315, respectively. The rims 314, 315 have exterior surfaces 316, 317 that interact with the cap as described in more detail below.

As further seen in FIGS. 36 and 37, cap 320 of the present embodiment comprises an upper portion 325 that is generally circular in shape. The upper portion 325 has a central hole 330 that is adapted to receive a set screw (not shown). Two arms 332, 334 extend downward from the cap's upper portion 325. Each arm 332, 334 of cap 320 is configured with radially outwardly extending protrusions that are designed to interact with the inwardly extending protrusions 306, 307, 308 and 309 of coupling body 300.

Figure 38:
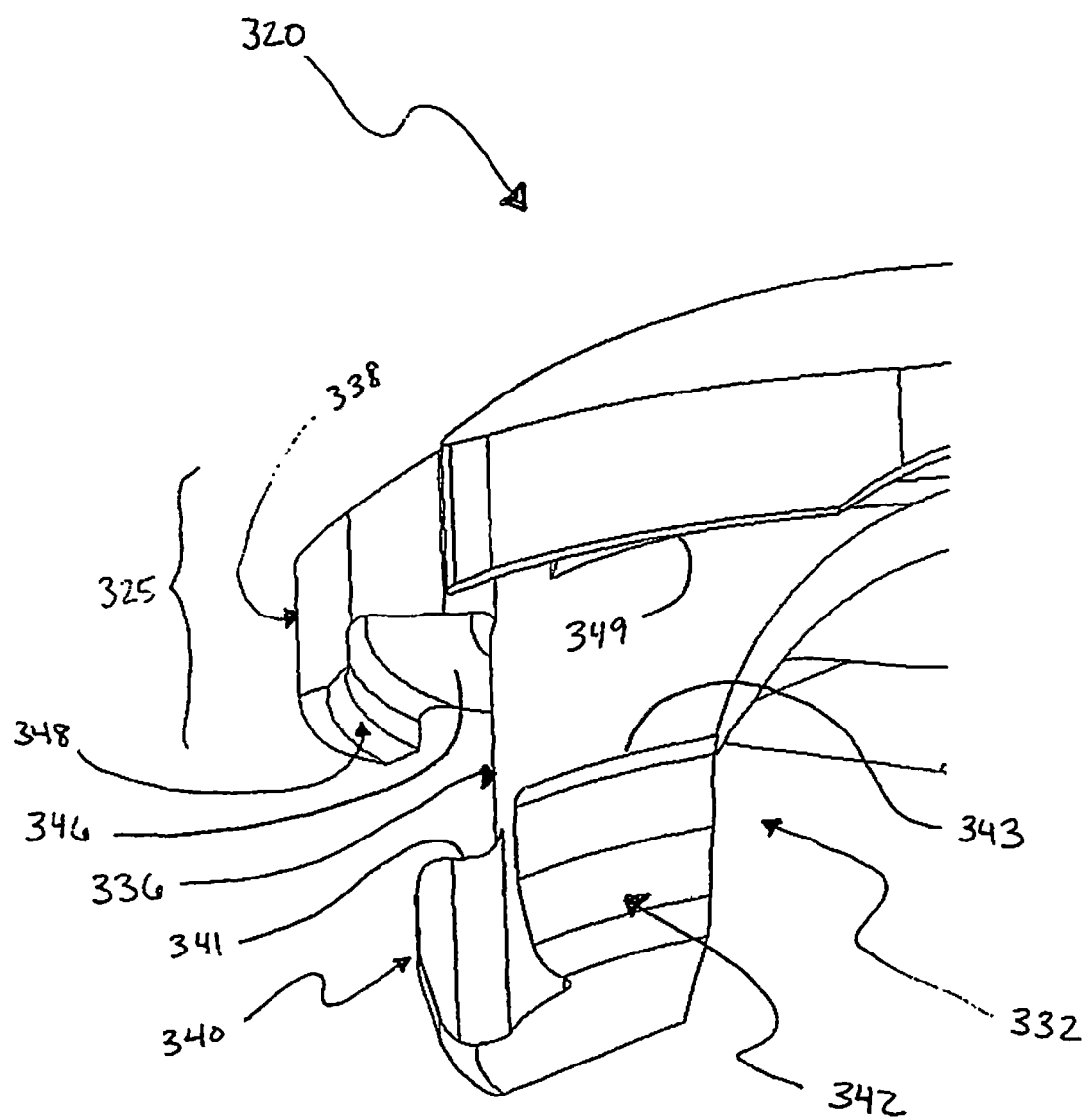
FIG. 38 is a partial perspective (global) view of a cap of the embodiment of FIG. 36.

With continuing reference to the embodiments shown in FIGS. 36 and 37, FIG. 38 illustrates a partial view of a cap design of the present invention. As seen in FIG. 38, the exterior perimeter 336 of arm 332 is offset radially inward with respect to perimeter 338 of upper portion 325. Disposed along the exterior perimeter 336 of arm 332 are two outwardly extending radial protrusions 340, 342. Outwardly extending radial protrusions 340, 342 are configured to fit within spaces created by inward facing protrusion 306, 307 of coupling body 300 upon insertion of cap 320 onto coupling body 300, e.g., when cap 320 is moved along the longitudinal axis. As seen in FIGS. 36-38, protrusions 340, 342 of cap 320 are designed with superior surfaces 341, 343 that interact with the inferior surfaces of the corresponding inwardly projecting protrusions of coupling body 300, in this case, inwardly projecting protrusions 306, 307 of coupling body 300. As one of skill in the art would understand, arm 334 similarly has outwardly extending radial protrusions 350, 352 (best seen in FIG. 37) that similarly interact with their corresponding inwardly extending radial protrusions, i.e. 308, 309 of coupling body 300. In some embodiments, the contact surfaces of the protrusions may be designed to provide an interference fit, a friction fit, a tongue and groove fit, or other known interaction fits that lock or prevent the cap from rotating out of the closed position. As seen in FIG. 36, the inferior and superior surfaces of the protrusions may also be designed with sloped surfaces that upon rotation of the cap into the closed position, prevent arms 302, 304 of the coupling body 300 from splaying.

With continuing reference to FIGS. 36-38, upper portion 325 of cap 320 is configured with a retaining edge about the inferior perimeter of the upper portion 325. With reference to FIG. 38, the inferior surface 346 of upper portion 325 is configured with a retaining edge 348. Retaining edge 348 is configured to interact with rim 314 of coupling body 300. Upon insertion of the cap onto the coupling body 300, retaining edge 348 engages rim 314 of coupling body 300. This design feature of the present embodiment provides stability to coupling body 300, and more particularly, may radially capture arm 302 or prevent splaying of arm 302.

Figure 39:
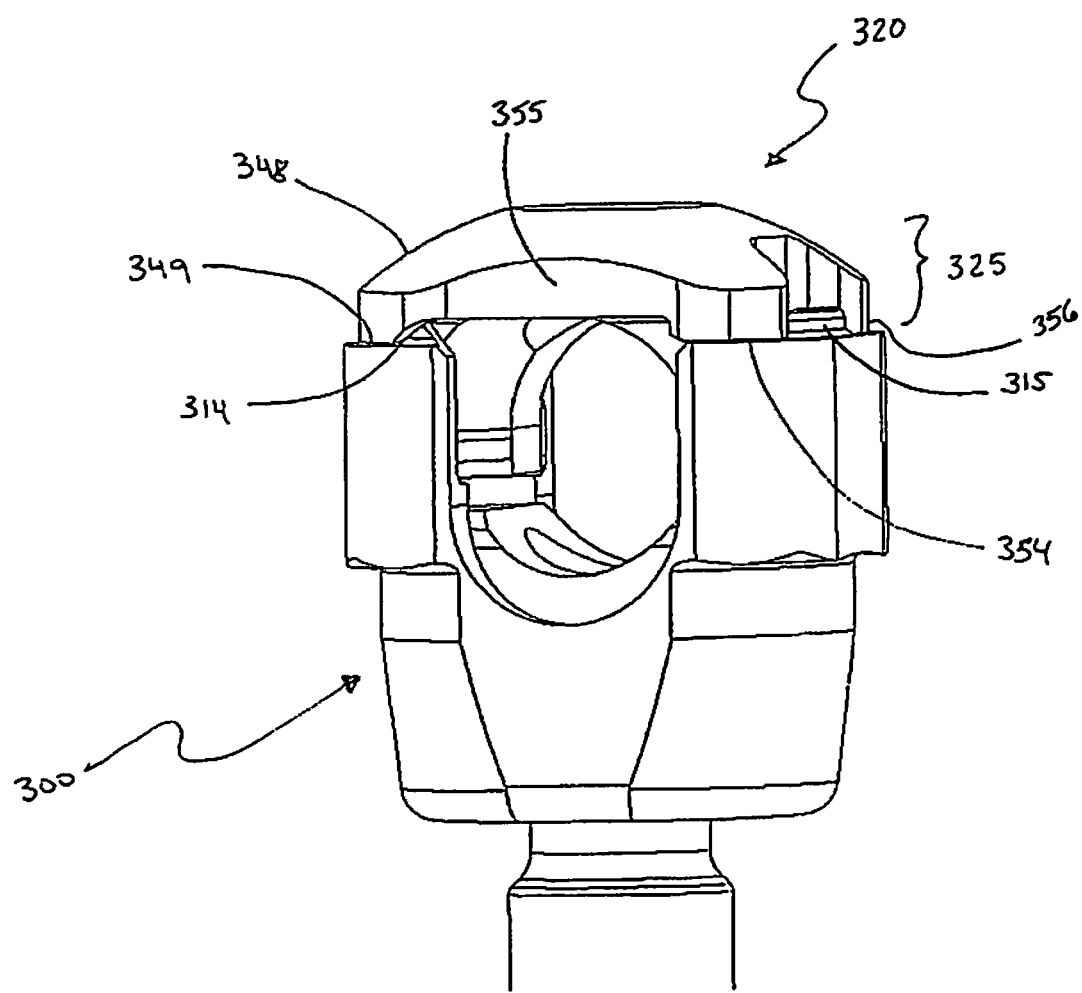
FIG. 39 is a side view of the embodiment of FIG. 36.
Figure 40:
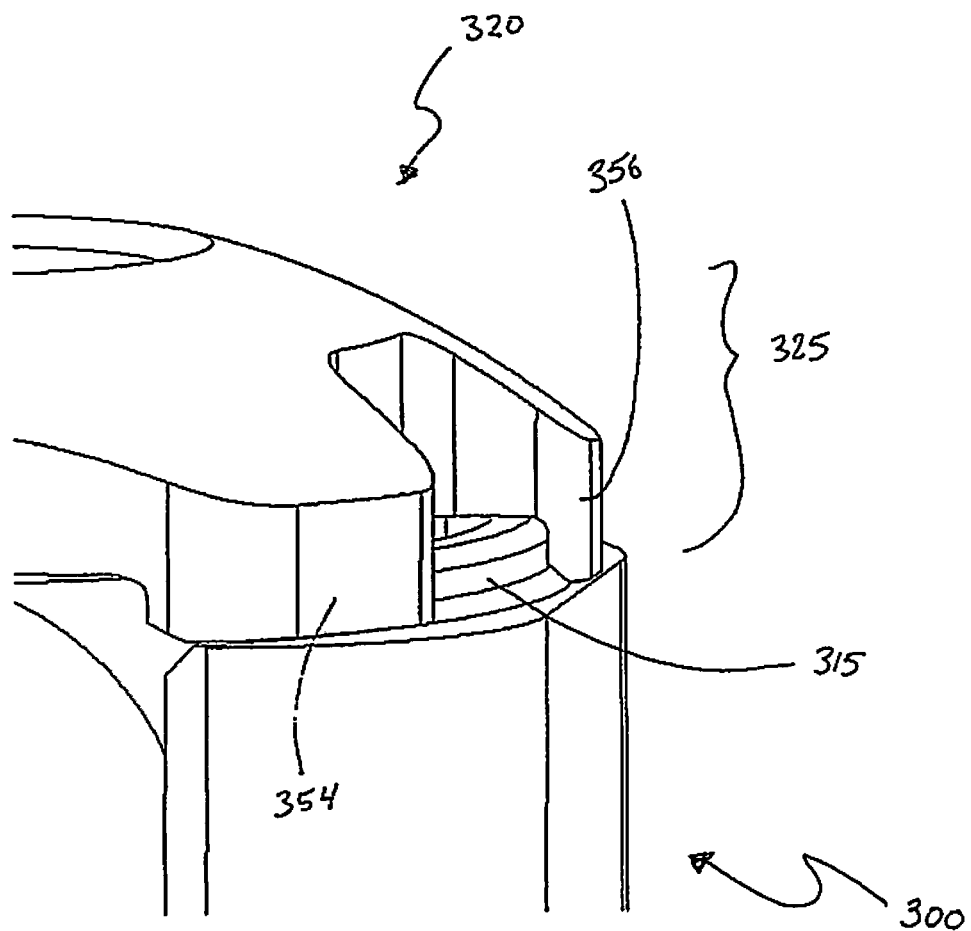
FIG. 40 is a partial perspective view of the embodiment of the FIG. 36.

As further seen in FIG. 39, cap 320 may be rotated into a second or closed position. In the closed position, the retaining edges 348 (hidden) and 349 of upper portion 325 contact rims 314, 315 of coupling body 300. As further illustrated by FIG. 39, in its closed position inwardly extending radial protrusions 306-309 of coupling body 300 are similarly engaged with the outwardly extending radial protrusions 340, 342, 350, and 352 of arms 332, 334 of cap 320 respectively and as previously described. With reference to FIG. 40, a partial close-up view of cap 320 and coupling body 300 is shown. FIG. 40 illustrates the interaction between rim 315 of coupling body 300 and retaining edges 354, 356 of upper portion 325 of cap 320 when cap 320 is in the second position.

FIG. 39 further illustrates another feature of an embodiment of the present invention. With reference to FIG. 39, upper portion 325 of cap 320 resides substantially above coupling body 300. Upper portion 325 may be designed with flat surface 355. Accordingly, these opposing flat surfaces may be used as engagement surfaces for a tool to grasp cap 320. Furthermore, as one of skill in the art would understand, tools designed to engage the flat surfaces of upper portion 325 of cap 320 may be used not only to insert cap 320 into coupling body 300 but also to rotate cap 320 into a second or closed position. Additional embodiments contemplate the use of alternative engagement surfaces and mechanisms to allow tools to insert and rotate the cap.

As described previously, when the cap is in the second or closed position, the cap may be locked or otherwise prevented from being rotated into the first or open position. As one of skill in the art would understand, any variety of mechanical means may be employed to prevent the cap from rotating from the second or closed position to the first or open position. For example, interference or friction fits may be designed into any number of components of the cap and coupling body. Alternatively, separate components such as pins, screws, wedges, etc. may be used to lock, secure, or otherwise prevent rotation from the second position to the first position. One such non-limiting example is the use of a set screw to lock the cap into position. Upon insertion of the cap and rotation into its closed position, a set screw may be used to lock all components of the polyaxial screw. As previously described, the set screw may lock the coupling body and fastener into a fixed position. In addition, the force of the set screw can lock the cap into its closed position via the counteracting force of the inward and outward protrusions of the cap and coupling body.

Figure 41:
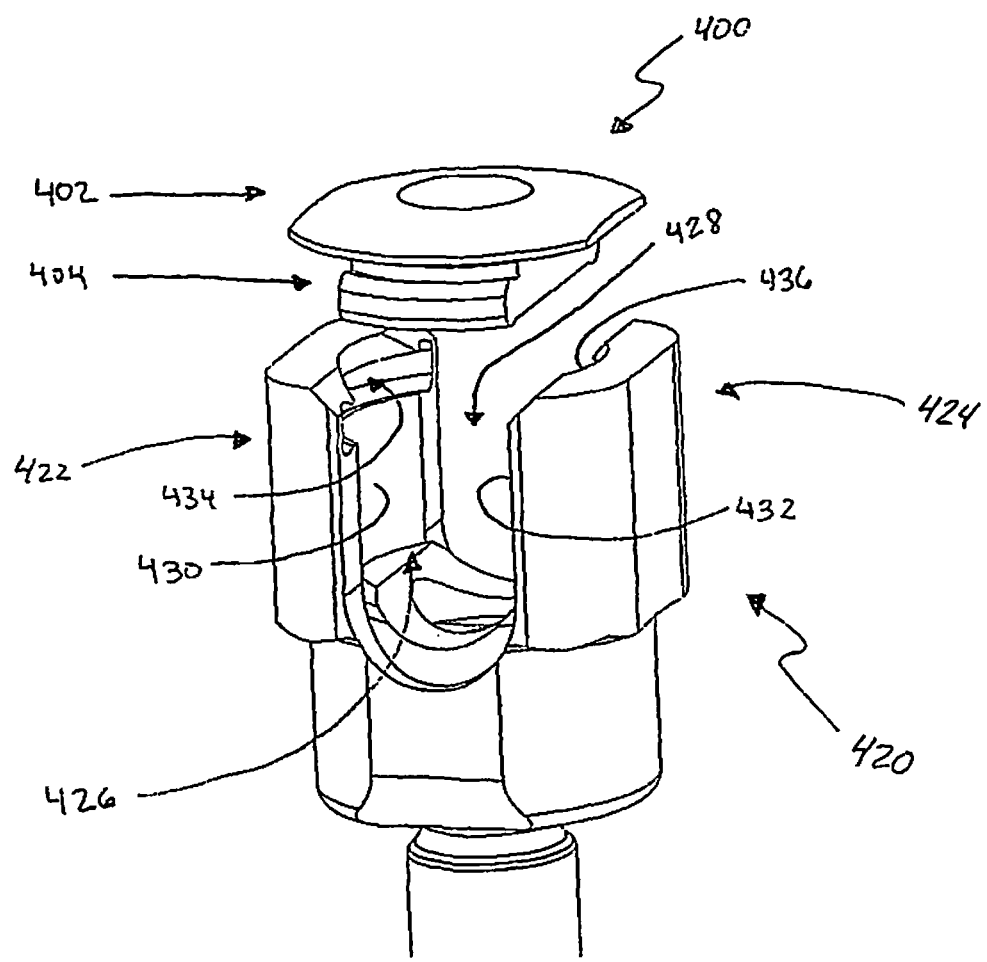
FIG. 41 is a partially exploded perspective view of another embodiment of the present invention.

Referring to FIGS. 41-46, another embodiment of the present invention is provided. With reference to FIG. 41, cap 400 and coupling body 420 are shown. In this embodiment of the present invention, cap 400 comprises an upper portion 402 and lower portion 402. As can be seen from FIG. 41, cap 400 is generally cylindrical in shape. With continuing reference to FIG. 41, coupling body 420 is illustrated. In an embodiment of the present invention, coupling body 420 contains two upwardly extending arms 422, 424 that extend longitudinally in the proximal direction. The coupling body has two slots 426, 428 configured to receive an elongate rod (not shown). Arms 422, 424 of coupling body 420 have interior and exterior surfaces. The interior surface 430, 432 of arms 422, 424 respectively are configured with a channel or groove. In FIG. 41, only channel or groove 434 is shown, whereas the corresponding channel or groove 436 on arm 424 is not visible.

Figure 42:
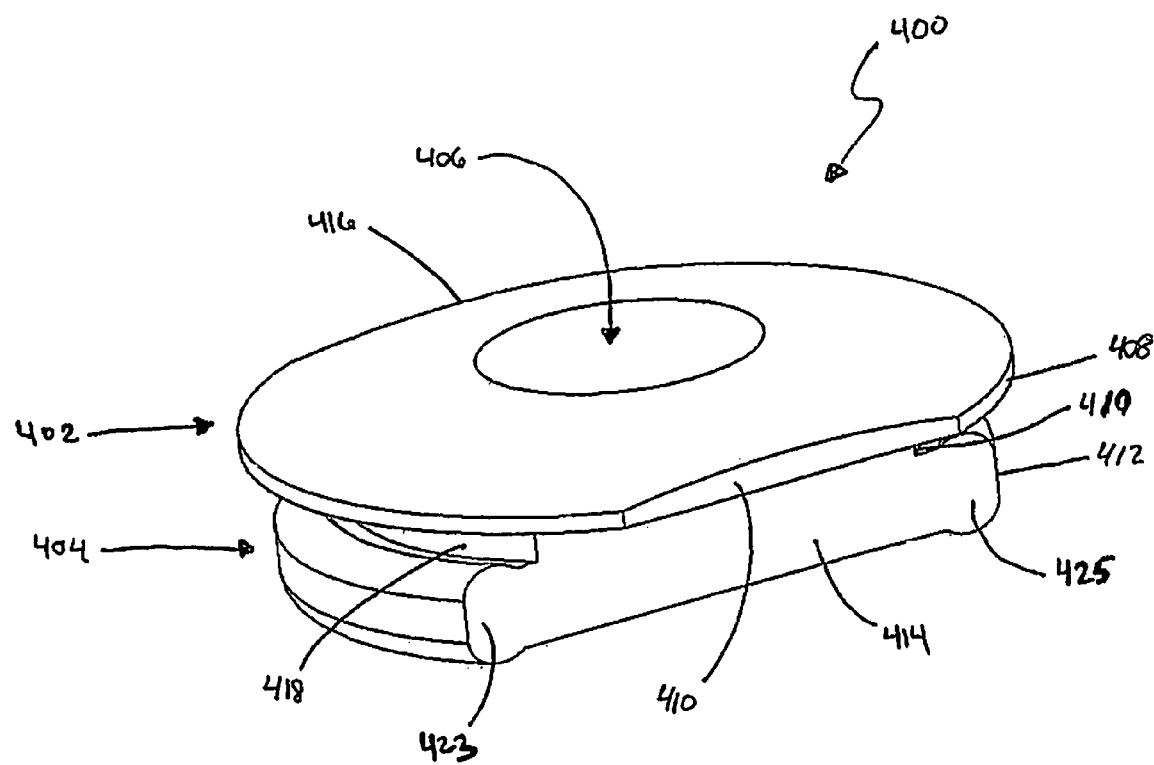
FIG. 42 is an perspective view of a cap of the embodiment of the FIG. 41.

With continuing reference to the embodiment of FIG. 41, FIG. 42 illustrates cap 400 of the present embodiment. As can be seen in FIG. 42, cap 400 has a centrally located bore hole 406 which is configured to receive a set screw. Cap 400 also has an upper portion 402 and lower portion 404. Upper portion 402 is generally cylindrical in shape and has a perimeter portion 408 that is generally circular in shape. As can be seen in FIG. 42, perimeter 408 of upper portion 402 of cap 400 may be formed with a flat or substantially linear portion 410 that is not generally circular in shape. Linear portion 410 of perimeter 408 may be used as an engagement point where a tool may engage cap 400. Tools may be used to grasp and insert cap 400 into coupling body 420.

As further seen in FIG. 42, lower portion 404 extends in the distal direction from upper portion 402. Lower portion 404 is generally cylindrical in shape and has a perimeter 412 offset radially inward with respect to perimeter 408 of upper portion 402. Lower portion 404 has two sidewalls 414, 416 that are generally linear or flat and are located on opposing sides of lower portion 404. Between opposing sidewalls 414, 416 are two generally circular sidewall portions 418, 419. Tongues 423, 425 extend radially from the generally circular sidewall portions 418, 419 of cap 400. Tongues 423, 425 run generally the entire length or perimeter of the sidewall portions 418, 419 of lower portion 404 of cap 400.

Figure 43:
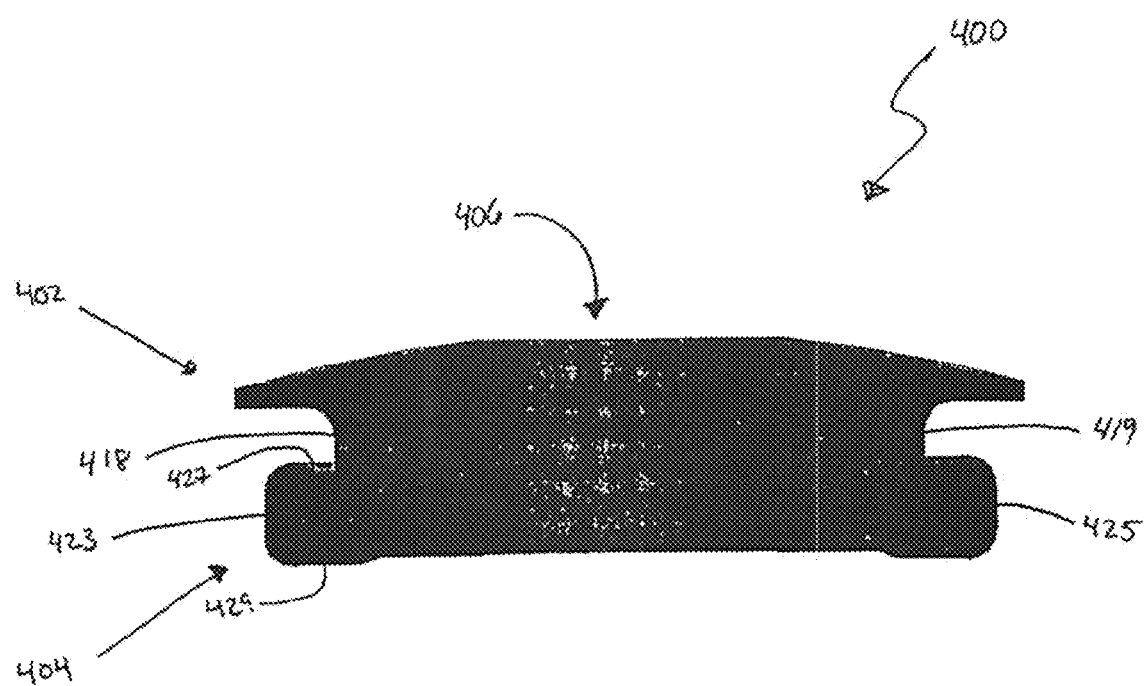
FIG. 43 is a cross-sectional view of the cap of FIG. 42.

Referring to FIG. 43, a cross-sectional view of cap 400 of the present embodiment is illustrated. As can be seen in FIG. 43, tongues 423, 425 extend radially from sidewall portions 418, 419 of lower portion 404 of cap 400. Tongues 423, 425 may be configured with a rounded or cylindrical profile. Thus, for example as one moves radially from the exterior perimeter 418 of lower portion 404 the profile of tongue 423 increases in both the proximal and distal direction. At its outermost portion, the profile of tongue 423 decreases until it becomes a flat edge, creating a partial cylindrical profile as seen in FIG. 43. This profile generally creates two interior engagement surfaces 427, 429 on tongue 423, which extend along tongue 423. While the discussion has focused only on tongue 423, one of skill in the art would understand that tongue 425 has a similar profile as seen in FIG. 43. In alternative embodiments, the profile of tongues 423, 425 may differ, including but not limited to, angular profiles with sloping surfaces, non-symmetrical surfaces, and straight, linear or generally perpendicular profiles.

FIG. 43 further illustrates opening or bore hole 406 that extends longitudinally through cap 400. While not shown in this particular embodiment, in some embodiments bore hole 406 may have threads along the interior surface of bore hole 406, which may be designed to engage a set screw. Alternative embodiments contemplate use of other fastening devices known in the art that may interact with bore hole 406 of cap 400.

Figure 44:
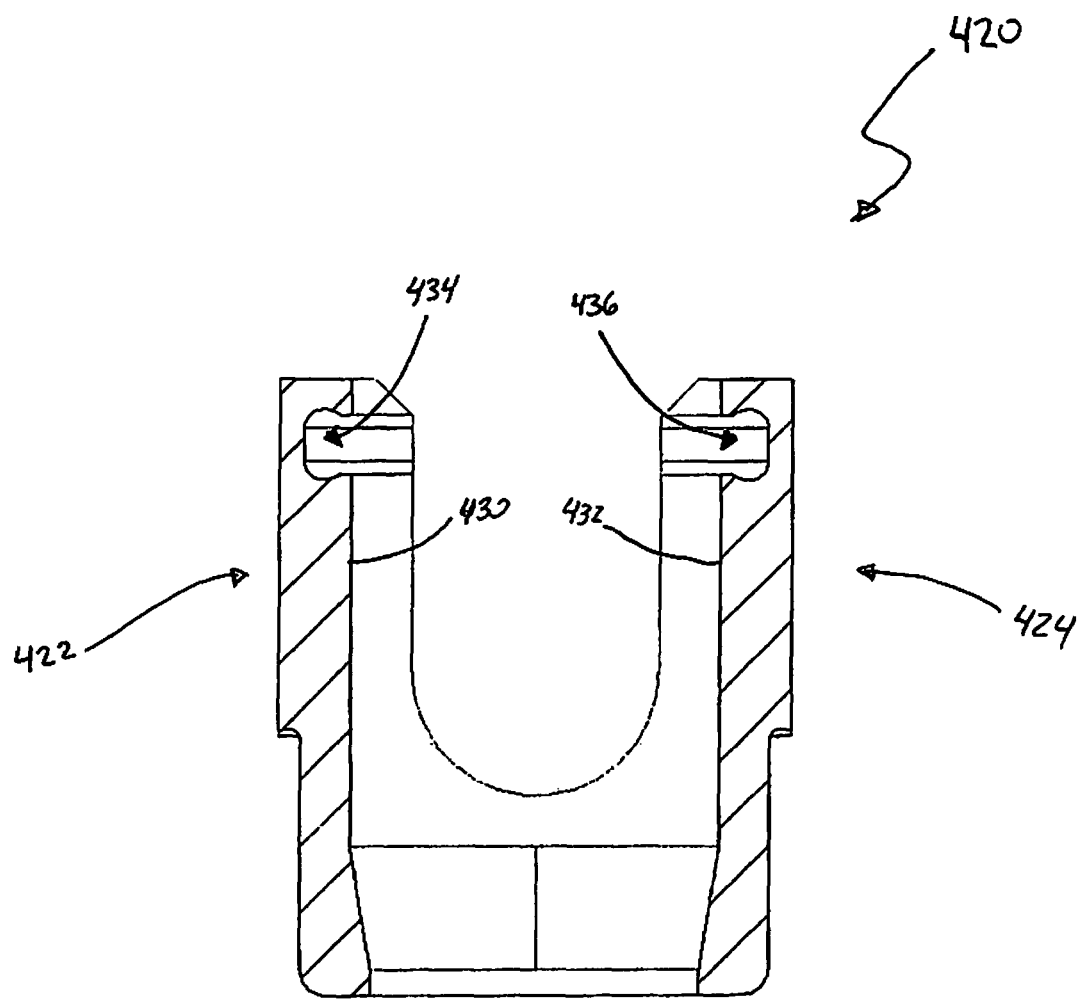
FIG. 44 is a cross-sectional view of a coupling body of the embodiment of FIG. 41.

Referring to FIG. 44 a cross sectional view of coupling body 420 of an embodiment of the present invention is shown. As seen in FIG. 44, coupling body 420 comprises two upwardly extending arms 422, 424 that extend longitudinally in the proximal direction. The coupling body has two slots configured to receive an elongate rod (not shown). Arms 422, 424 of coupling body 420 have interior and exterior surfaces. Interior surface 430, 432 of arms 422, 424 respectively are configured with channels or grooves 434, 436. As can be seen in FIG. 44, groove 434 contains a profile that is slightly larger than the profile of tongue 423. Groove 434 extends substantially along the entire interior surface 430 of arm 422 of coupling body 420. Similarly, groove 436 contains a profile that is slight larger than the profile of tongue 425. Groove 436 also extends substantially along the entire interior surface 432 of arm 424 of coupling body 420. As with the discussion pertaining to tongues 423, 425, the profiles of grooves 434, 436 create engagement surfaces. Accordingly, groove 434 contains engagement surfaces, which extend the entire length of groove 434. Similarly, groove 436 contains engagement surfaces, which extend the entire length of groove 436.

Figure 45:
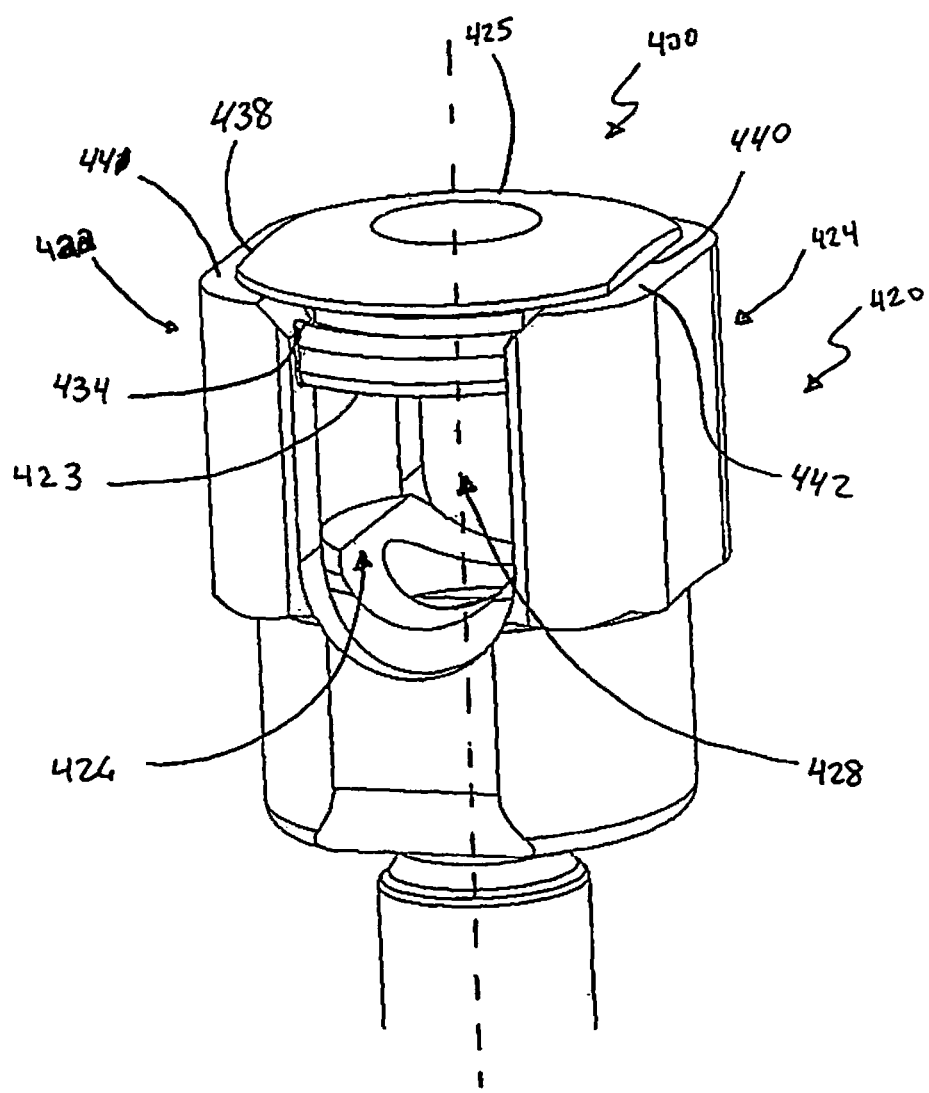
FIG. 45 is a partial perspective view of the embodiment of FIG. 41 with the cap shown in a first position.

Referring to FIG. 45, cap 400 is shown inserted into coupling body 420. As seen in FIG. 45, cap 400 is in a first position, wherein insertion is accomplished by moving cap 400 longitudinally downward into coupling body 420. Tongues 423, 425 are dimensioned to fit within slots 426, 428 respectively when cap 400 is inserted into coupling body 420. Inferior surfaces 438, 440 of upper portion 402 of cap 400 are designed to contact upper surfaces 441, 442 of arms 422, 424 respectively of coupling body 420. The interaction between these surfaces places cap 400 at a predetermined location along the longitudinal axis of coupling body 420. As seen in FIG. 45, tongues 423, 425 are positioned such that they are aligned with grooves 434, 436 of coupling body 420 when cap 400 is inserted into coupling body 420.

Figure 46:
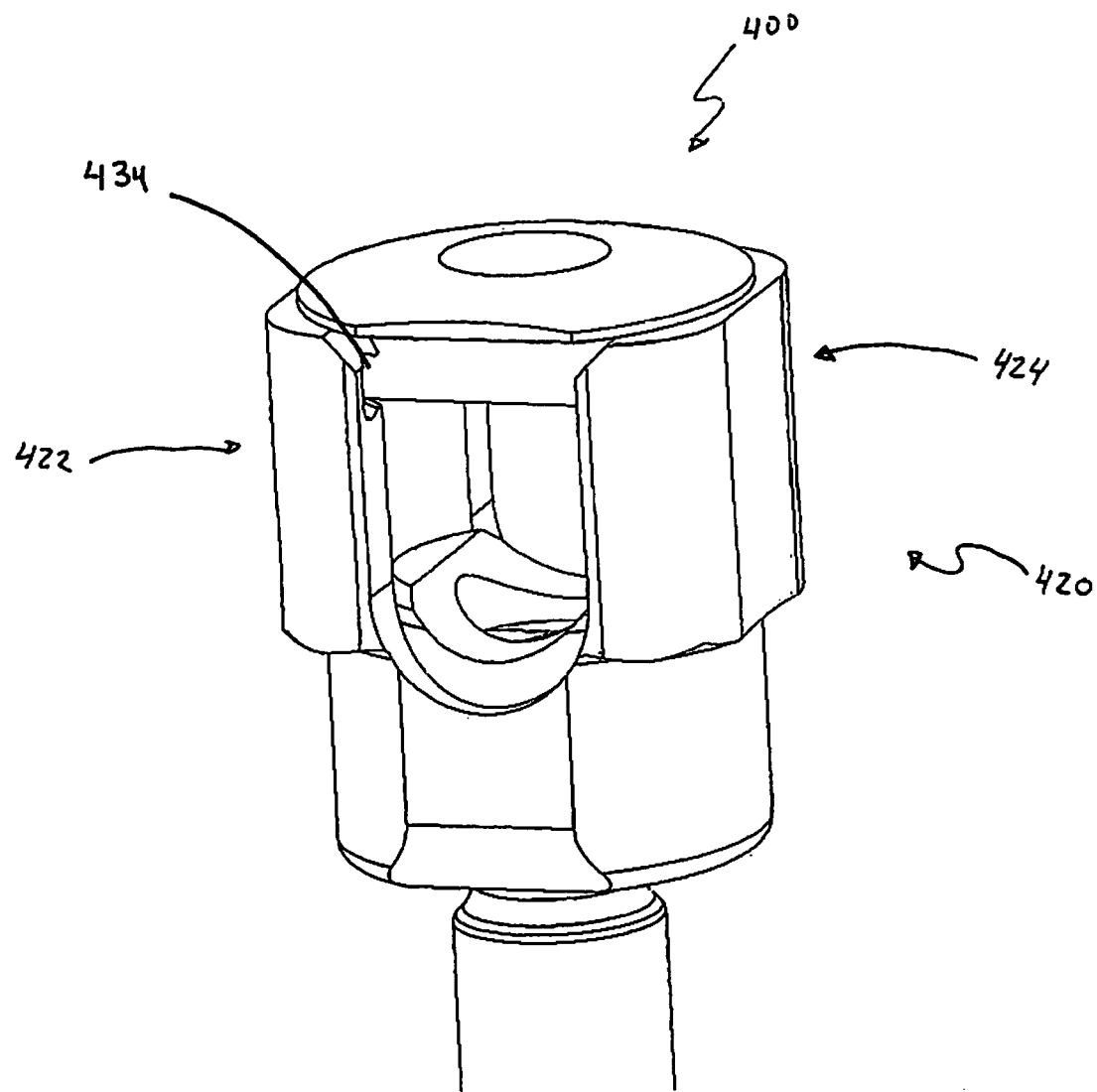
FIG. 46 is a partial perspective view of the embodiment of FIG. 41 with the cap shown in a second position.

Referring to FIG. 46, a cap 400 is illustrated in a second position wherein cap 400 has been rotated after insertion into coupling body 420. As seen in FIG. 46, tongue 423 fits within groove 434. As cap 400 is rotated from a first position to a second position, tongues 423, 425 ride within corresponding grooves 434, 436. As described previously any number of stop or limiting mechanisms may be used to prevent cap 400 from rotating past a certain point and/or from rotating back into the first position once the second position has been reached.

As one of skill in the art would understand, one feature associated with the present embodiment is the ability of the present design to prevent splaying of the arms. In the second position, engagement surfaces 427, 429 of tongue 423, contact or may potentially engage engagement surfaces of groove 434. Similarly, tongue 425 contains engagement surfaces that contact or may potentially engage engagement surfaces of groove 436. Accordingly, the interaction between the aforementioned engagement surfaces can prevent splaying of arms 422 and 424 by virtue of the engagement of said surfaces. This feature adds structural rigidity to the polyaxial screw design. In addition to the prevention of splaying of the arms, the tongue and groove design of the present embodiment may lock or fix the polyaxial screw when desirable. For example, and as discussed previously, a set screw may be used to exert a downward force on the elongate rod. The counteracting upward force on the set screw is transmitted to the tongues of cap 400. As tongues 423, 425 lie within grooves 434, 436, the counteracting force transmitted to tongues 423, 425 causes tongues 423, 425 to engage with grooves 434, 436, thus locking or fixing the cap, elongate rod, and coupling body in place with respect to the fastener as described previously.

While the embodiment shown in FIGS. 41-46 is one in which the profile of the tongues and grooves are generally spherical in shape, one of skill in the art would understand that a variety of alternate profiles could be used. Any number of shapes, including generally linear profiles, perpendicular profiles, non-symmetrical profiles, etc. can be used to either prevent splaying of the arms and/or serve as a locking mechanism for the elongate rod and polyaxial screw.

Figure 47:
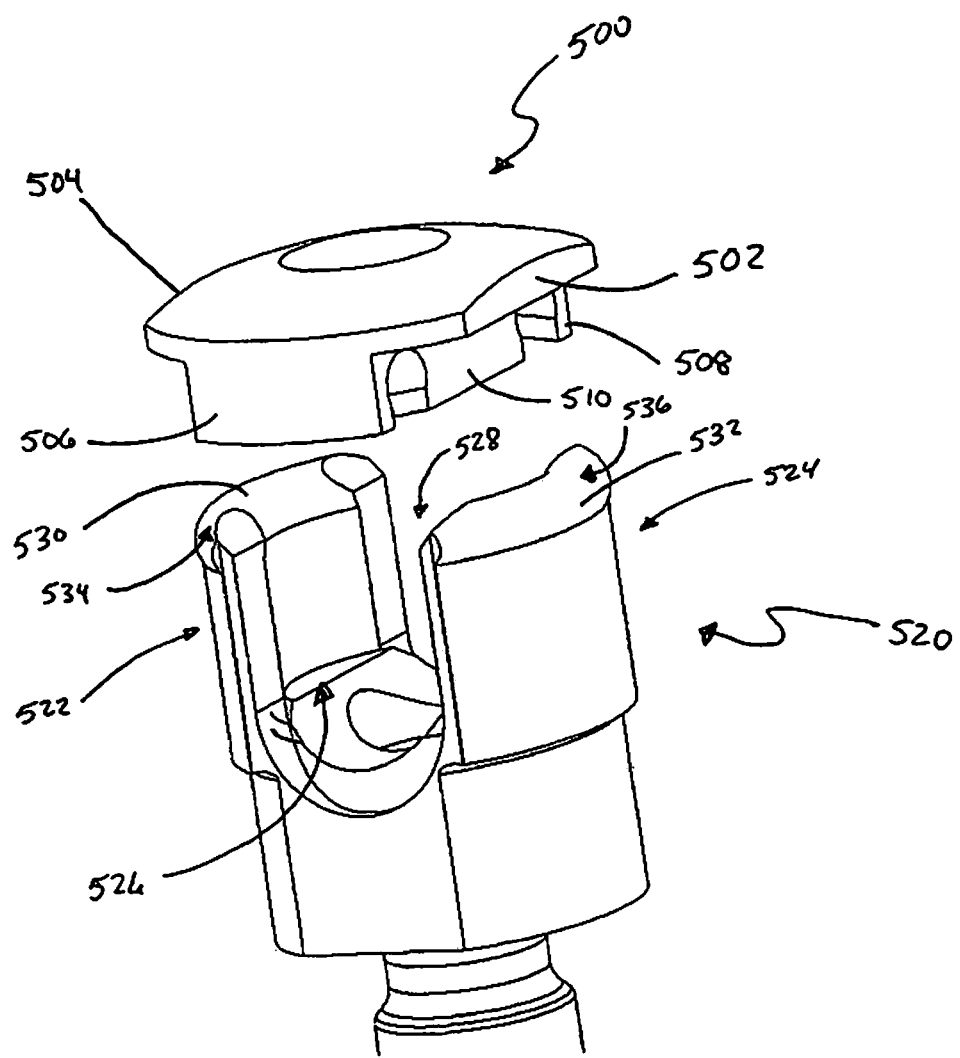
FIG. 47 is a partially exploded view of another embodiment of the present invention.

Referring to FIGS. 47-53, another embodiment of the present invention is provided. With reference to FIG. 47, cap 500 and coupling body 520 are shown. In this embodiment of the present invention, cap 500 has a generally cylindrical shape. As seen in FIG. 47, cap 500 has two opposing generally linear side portions 502, 504. Two flange portions 506, 508 extend longitudinally in a distal direction. Disposed centrally within cap 500 is a central portion 510 extending distally in a longitudinal direction. In an embodiment of the present invention, coupling body 520 contains two upwardly extending arms 522, 524 that extend longitudinally in the superior direction. The coupling body has two slots 526, 528 configured to receive an elongate rod (not shown). Arms 522, 524 of coupling body 520 have interior, exterior, and upper surfaces. The upper surfaces 530, 532 of arms 522, 524 respectively are configured with tongues 534, 536, which are made with a profile discussed in more detail below.

Figure 48:
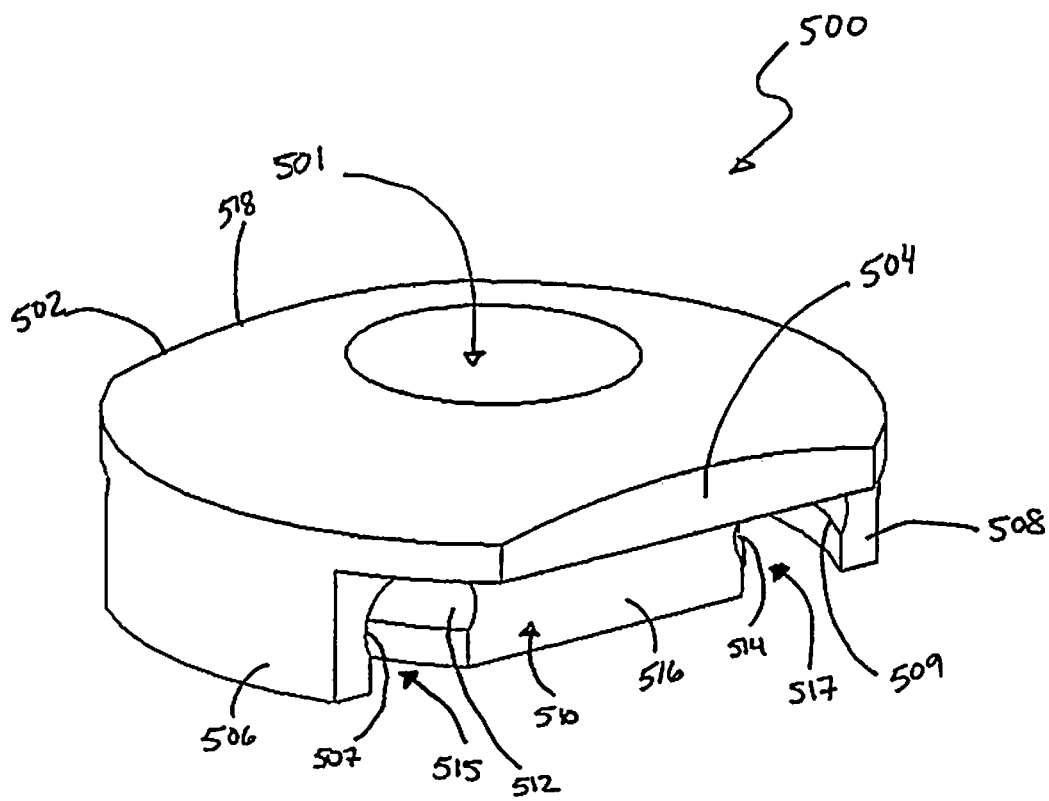
FIG. 48 perspective view of a cap of the embodiment of FIG. 47.

Referring to FIG. 48, cap 500 of the present embodiment is illustrated. As can be seen in FIG. 48, cap 500 has a centrally located bore hole 501, which is configured to receive a set screw. Cap 500 is generally cylindrical in shape. Cap 500 also may have two generally linear faces 502, 504 that oppose each other. Linear faces 502, 504 may be used as an engagement points for a tool to grip cap 500. Tools may be used to grasp, insert, and rotate cap 500 into coupling body 520.

As further seen in FIG. 48, two flanges extend longitudinally in an distal direction from cap 500. Flanges 506, 508 have interior and exterior surfaces that are curved and follow an arcuate path that corresponds generally to the generally cylindrical external perimeter of cap 500. Central portion 510 extends longitudinally in a distal direction and is generally cylindrical in shape. Surfaces 512, 514 of central portion 510 generally correspond to the cylindrical shape of flanges 506, 508 and similarly follow an arcuate path in a circumferential direction about the central axis of cap 500. Central portion 510 also has two opposing generally linear or flat faces 516, 518 that are offset radially inward with respect to linear or flat faces 502, 504 of cap 500. Flange 506, and more particularly interior surface 507, and cylindrical surface 512 of central portion 510 define a groove or channel 515. Accordingly, groove 515 is generally cylindrical in shape and extends in an arcuate path that generally corresponds to the cylindrical shape of cap 500. Similarly, flange 508, and more particularly interior surface 509, and cylindrical surface 514 of central portion 510 define a second groove or channel 517. Accordingly, groove 517 is generally cylindrical in shape and extends in an arcuate path that generally corresponds to the cylindrical shape of cap 500.

Figure 49:
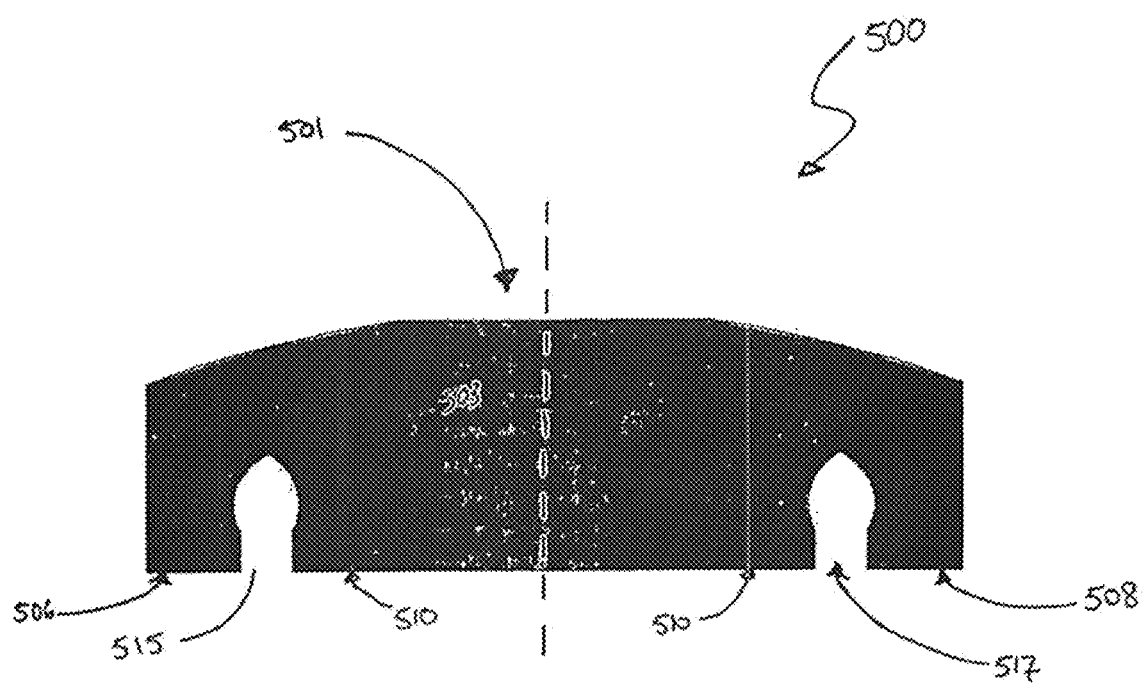
FIG. 49 is a cross-sectional view of the cap of the embodiment of FIG. 47.

Referring to FIG. 49, a cross sectional view of cap 500 of an embodiment of the present invention is shown. More particularly, FIG. 49 illustrates the profile of grooves 515, 517 of cap 500. Additionally, bore hole 501 is seen extending through cap 500. Bore hole 501 may be configured to receive a set screw by including threads (not shown) on the interior surface 503 of bore hole 501.

As seen in FIGS. 47-49; grooves 515 and 517 created by central portion 510 and flanges 506 and 508 respectively, may be made with various alternate profiles. In this embodiment of the present invention, grooves 515, 517 have a generally circular profile. Because grooves 515, 517 partially extend about a circumference spaced from central axis 505 of cap 500, the circular profiles create grooves that are generally curved cylindrical spaces.

Figure 50:
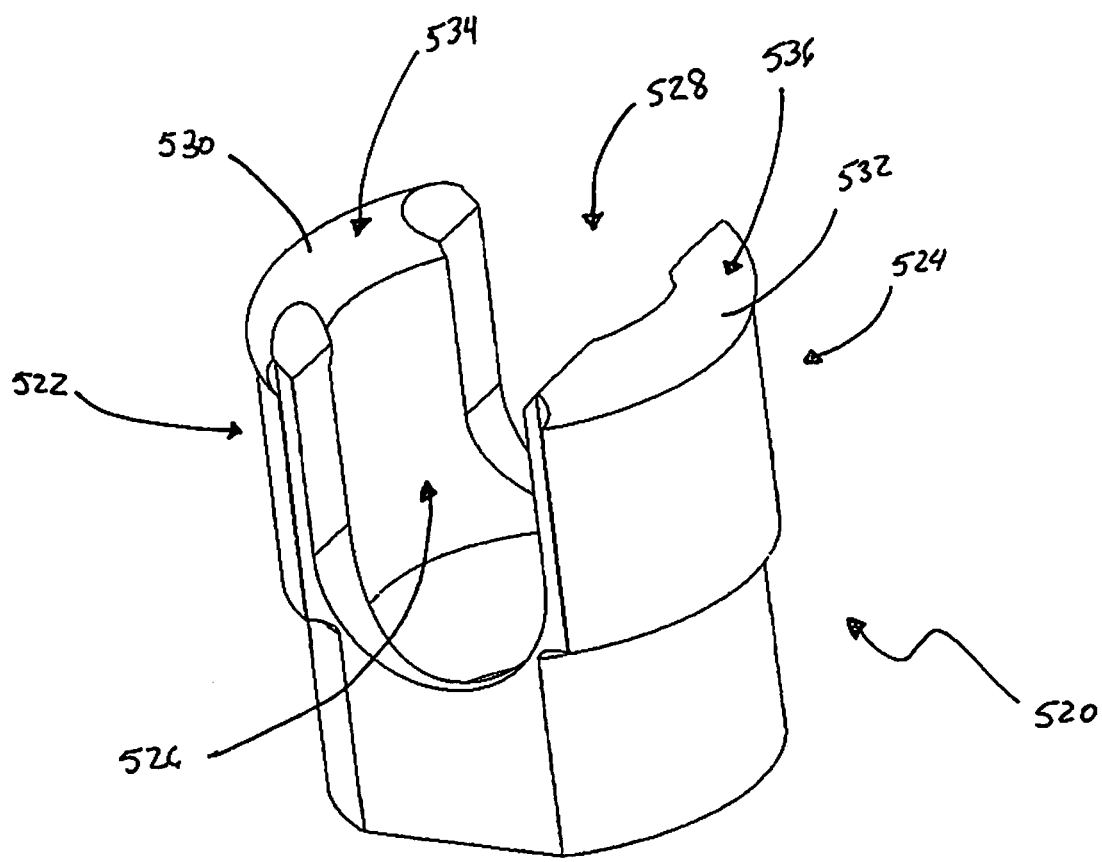
FIG. 50 is perspective view of the coupling body of the embodiment of FIG. 47.
Figure 51:
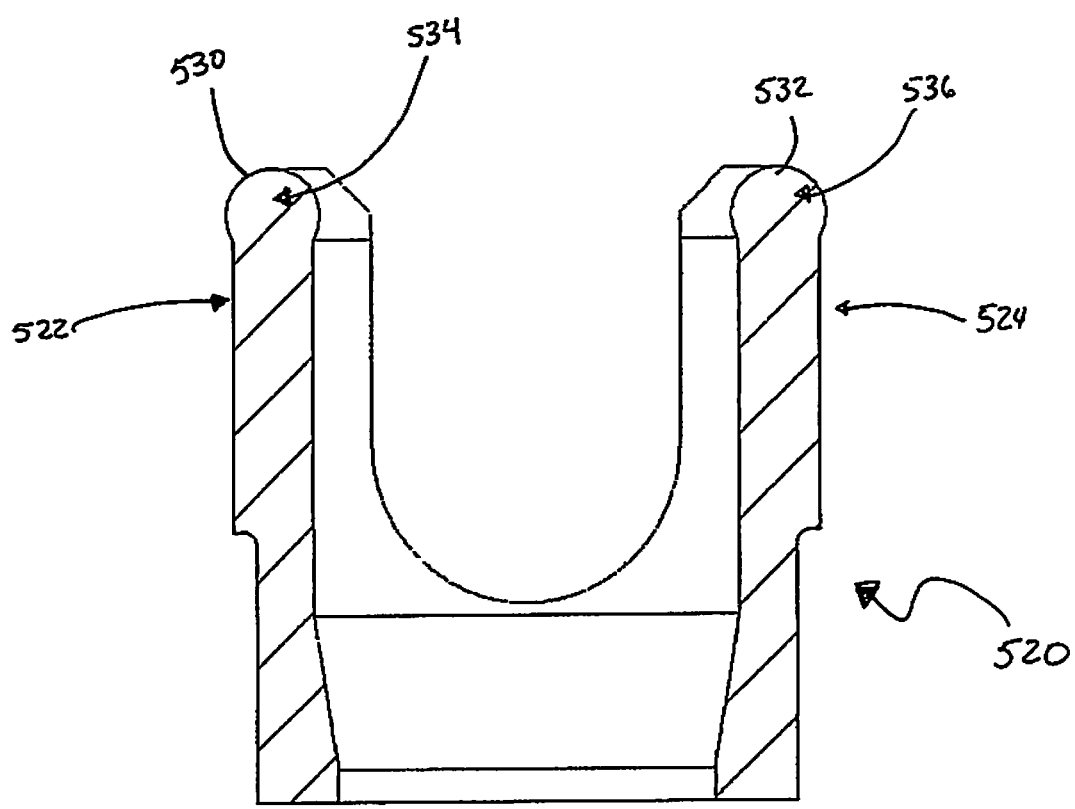
FIG. 51 is a cross sectional view of the embodiment of FIG. 47.

Referring to FIGS. 50 and 51, a coupling body of the present embodiment is shown. As seen in FIGS. 50-51, coupling body 520 contains two upwardly extending arms 522, 524 that extend longitudinally in the superior direction. The coupling body has two slots 526, 528 configured to receive an elongate rod (not shown). Arms 522, 524 of coupling body 520 have interior, exterior, and upper surfaces. As seen in FIGS. 50-51, arms 522, 524 are generally curved. The upper surfaces 530, 532 of arms 522, 524 are shaped with a profile to match the profile of grooves 515, 517, creating tongues 534, 536. Accordingly, as seen in FIG. 51 a cross sectional view of arms 522, 524 show the upper surfaces of the arms with a circular profile that matches or generally corresponds to the profile of grooves 515, 517 of cap 500.

Figure 52:
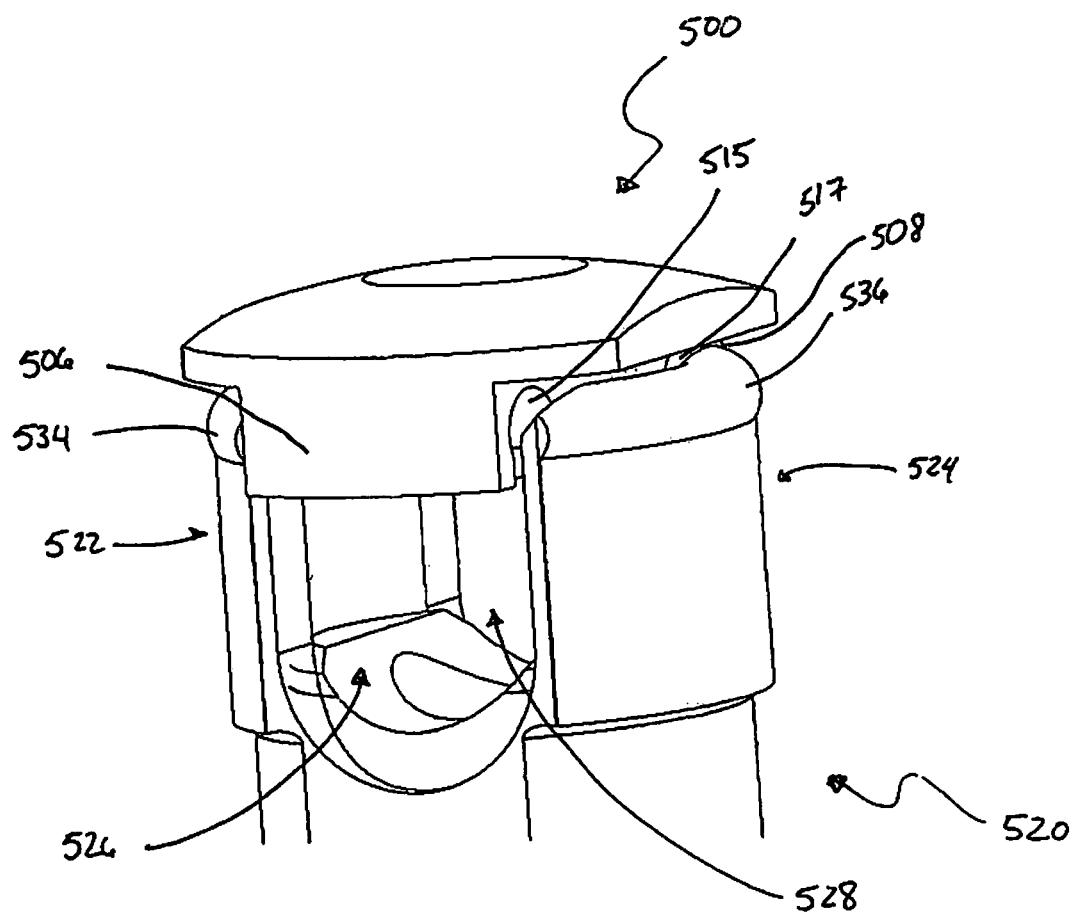
FIG. 52 is a partial perspective view of the embodiment of FIG. 47.

With continuing reference to FIGS. 47-51, FIG. 52 illustrates cap 500 inserted into coupling body 520. As seen in FIG. 52, cap 500 is in a first position, wherein insertion is accomplished by moving cap 500 longitudinally downward into coupling body 520. Central portion 510 and flanges 506, 508 are dimensioned to fit within slots 526, 528 when cap 500 is inserted. As seen in FIG. 52, grooves 515, 517 are positioned such that when cap is in the first position, grooves 515, 517 are aligned with tongues 534, 536 of coupling body 500.

Figure 53:
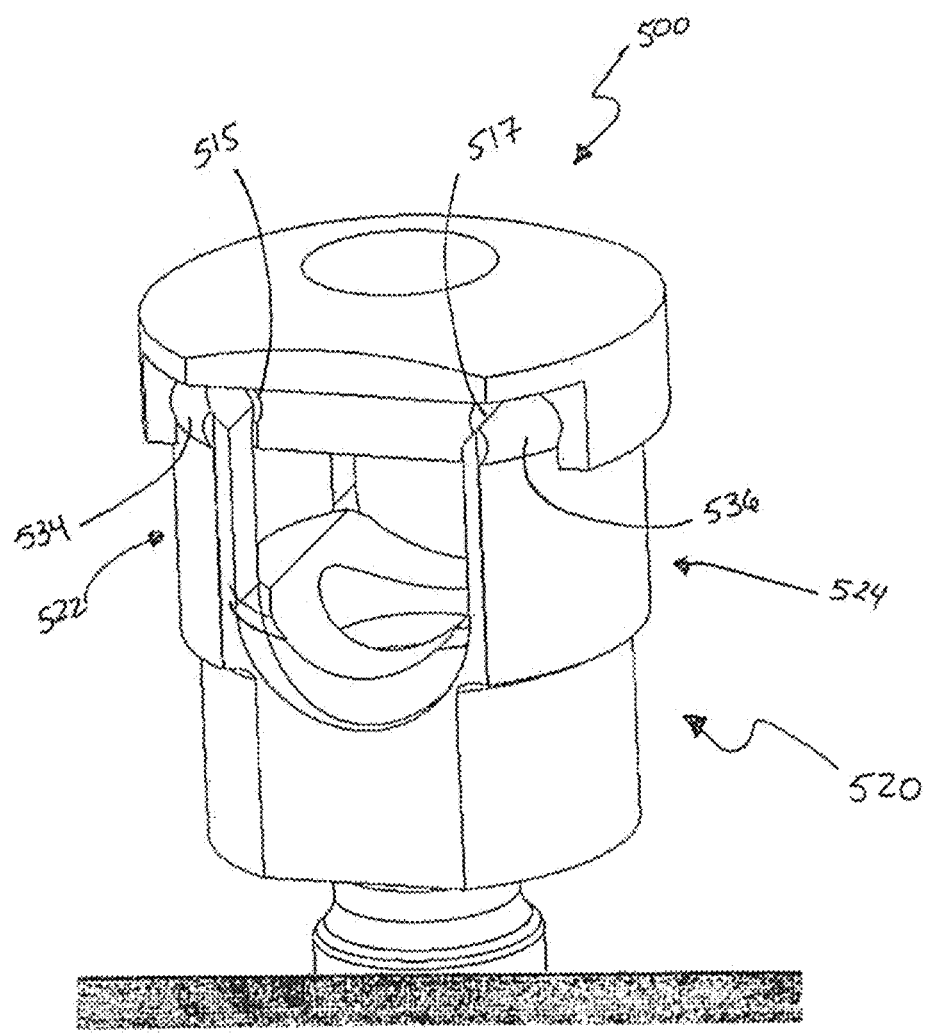
FIG. 53 is a partial perspective view of the embodiment of FIG. 47.

With continuing reference to FIGS. 47-52, FIG. 53 illustrates cap 500 in a second position wherein cap 500 has been rotated after insertion into coupling body 520. As seen in FIG. 53, tongues 534, 536 fit within grooves 515, 517 respectively. As cap 500 is rotated from a first position to a second position, tongues 534, 536 ride within corresponding grooves 515, 517. As described previously any number of stop or limiting mechanisms may be used to prevent cap 500 from rotating past a certain point and/or from rotating back into the first position once the second position has been reached.

As one of skill in the art would understand, one feature associated with the present embodiment is the ability of the present design to prevent splaying of the arms. In its second position, the tongue and groove fit prevents splaying of arms 522, 524 by virtue of the configuration of the tongue and groove design. In addition to the prevention of splaying of the arms, the tongue and groove design of the present embodiment locks or fixes the polyaxial screw when desirable. For example, and as discussed previously, a set screw may be used to exert a downward force on the elongate rod. The counteracting upward force on the set screw is transmitted to cap 500. The tongue and groove design of the present embodiment counteracts the downward force of the set screw causing the tongues to engage the grooves, thus locking or fixing the cap, elongate rod, and coupling body in place with respect to the fastener as described previously.

While the embodiment shown in FIGS. 47-53 is one in which the profile of the tongues and grooves are generally curved cylinders in shape, one of skill in the art would understand that a variety of profiles could be used. Any number of shapes, including substantially linear profiles, perpendicular profiles, non-symmetrical profiles, etc. can be used to either prevent splaying of the arms and/or serve as a locking mechanism for the elongate rod and polyaxial screw.

Figure 55:
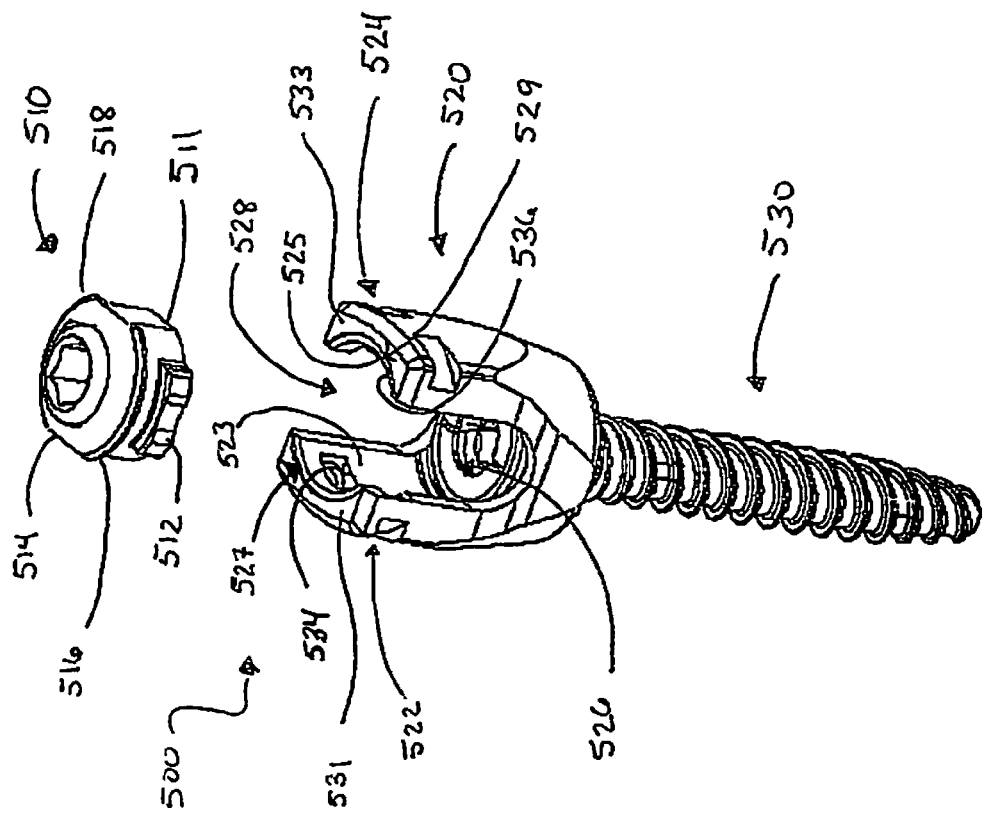
FIG. 55 is a partially exploded view of the embodiment of FIG. 54.
Figure 54:
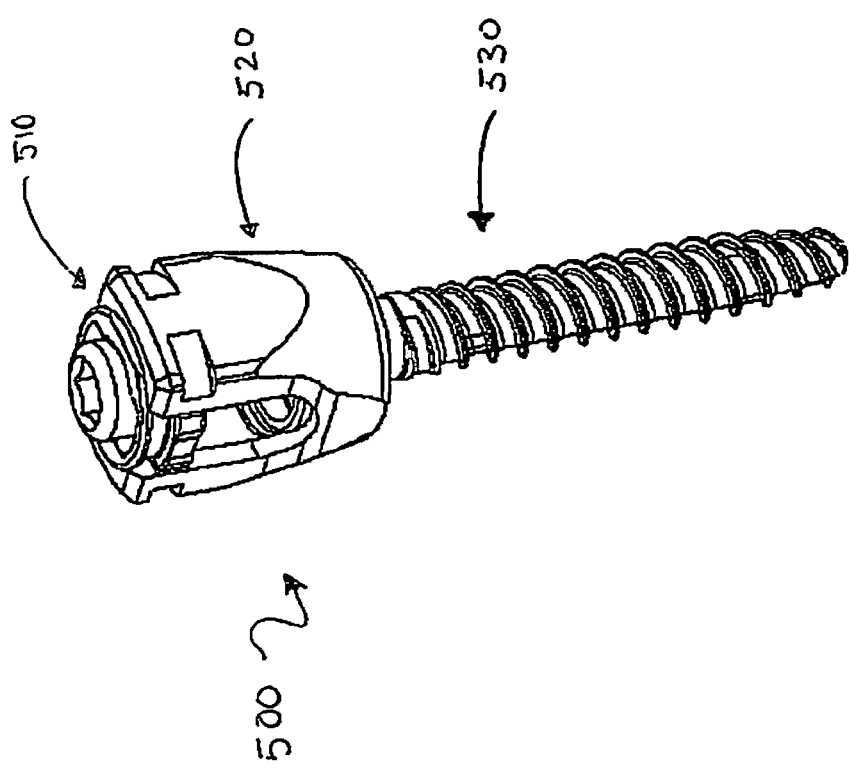
FIG. 54 is a perspective view of another embodiment of the present invention.

Referring to FIGS. 54-61, another embodiment of the present invention is provided. With reference to FIG. 54, a polyaxial screw assembly 500 is shown having a cap 510, a coupling body 520, and a fastener 530. As can be seen in FIG. 55, cap 510 is generally cylindrical in shape. Along a perimeter sidewall 511 of the generally cylindrical cap 510 are two protrusions 512, 514 (not visible). Each protrusion partially extends about the circumference of the cap sidewall 511. Protrusions 512, 514 are disposed along sidewall 511 in a position such that upon insertion, protrusions 512, 514 can be rotated into the coupling body channels 534, 536 as discussed below. As can be further seen in FIG. 55, the cap may be formed with a partial lip or rim. In this embodiment, cap 510 is formed with two rims 516, 518, which extend radially outward from the top end of the perimeter of cap 510.

Referring to FIG. 55, coupling body 520 is also illustrated. In an embodiment of the present invention, coupling body 520 contains two upwardly extending arms 522, 524, which extend longitudinally in the superior direction. The coupling body has two slots 526, 528 configured to receive an elongate rod (not shown). Arms 522, 524 of coupling body 520 have interior and exterior surfaces. The interior surfaces 523, 525 of arms 522, 524 respectively are configured with a channel or groove. In FIG. 55, only channel or groove 534 is shown, whereas the corresponding channel or groove 536 on arm 524 is hidden. Also seen in FIG. 55 are recesses 527, 529 formed in the upper surfaces 531, 533 of arms 522, 524. Recesses 527, 529 extend interior to the sidewalls 523, 525 of arms 522, 524. Recesses 527, 529 are designed to accept the lips or rims 516, 518 of the cap 510 when the cap is inserted into coupling body 520. In this manner, the design provides a mechanism or feature that positions the cap in a predetermined location in the longitudinal direction after insertion into the coupling body. The positioning feature of the present embodiment aligns the protrusions of the cap with the channels of the coupling body.

Figure 56:
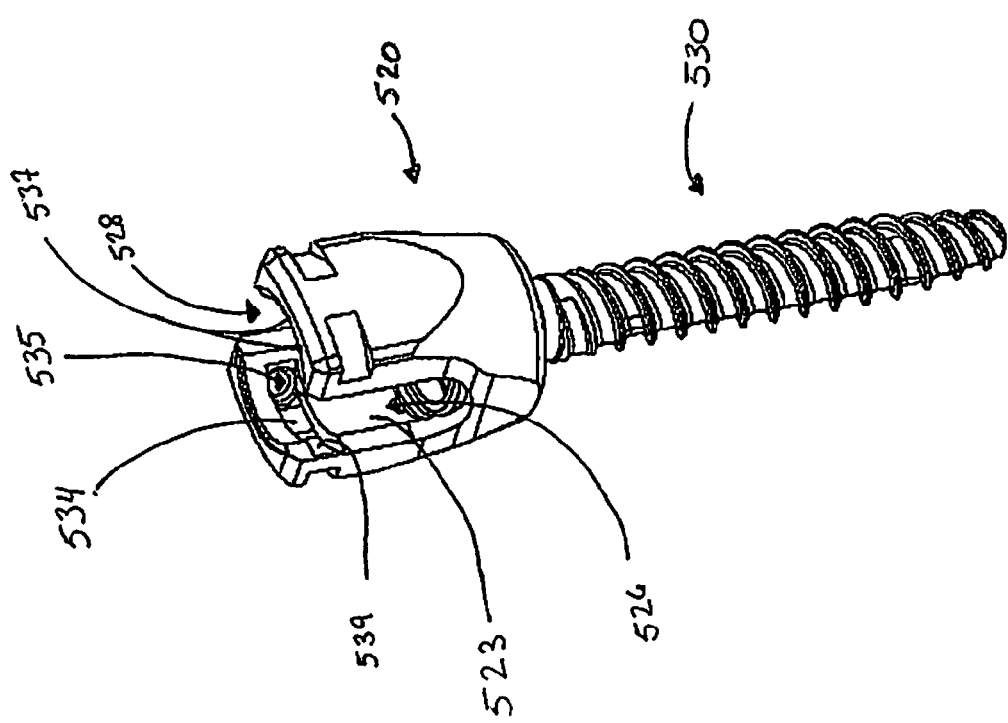
FIG. 56 is a perspective view of the embodiment of FIG. 54.

Referring to FIG. 56, interior sidewall 523 of coupling body 520 is seen. As seen in FIG. 56, channel 534 is formed within interior side wall 523 and partially extends along the interior perimeter of sidewall 523. At the proximal end, channel 534 is open and accessible from slot 526. At the distal end, channel 534 terminates prior to slot 528. As one of skill in the art would understand, corresponding channel 536 is similarly configured, except that channel 536 is open and accessible from slot 528 and terminates prior to reaching slot 526.

The height of channels 534, 536 are dimensioned to correspond to the thickness or height of protrusions 512, 514. Additionally, as seen in FIG. 56, channel 534 has a relief area at the termination end of channel 534. Relief area 535 is formed by a cavity that is radially larger than channel sidewall 539. As described in more detail below, relief area 535 interacts with protrusion 514 when cap 510 is rotated into a closed position. As one of skill in the art would understand, corresponding channel 536 is similarly configured except that relief area 537 (hidden) is located at the termination end of channel 536.

Figure 57:
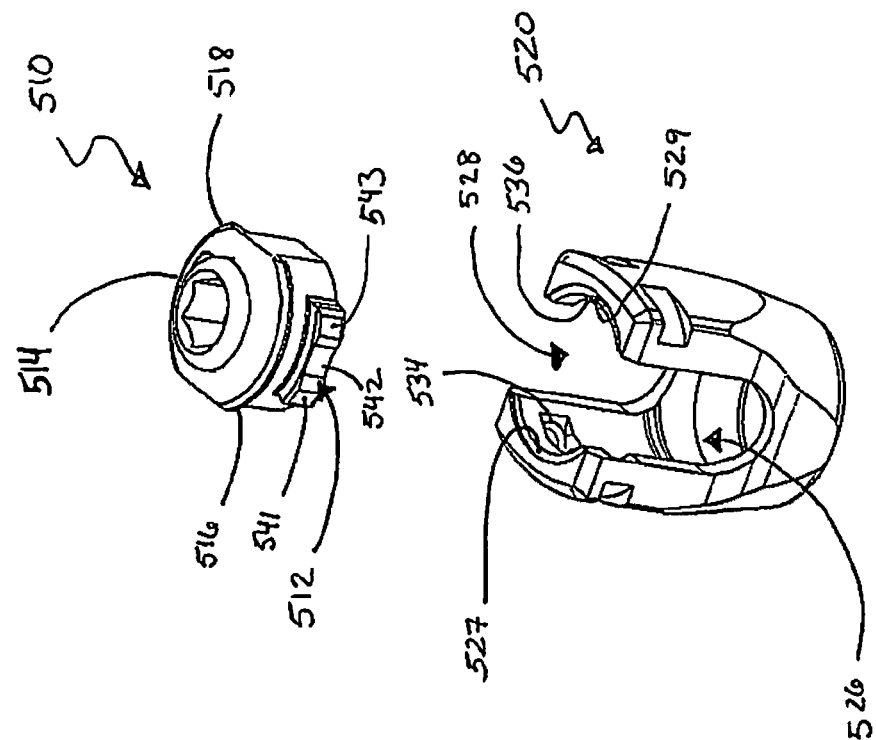
FIG. 57 is an partially exploded perspective view of the cap and coupling body of the embodiment of FIG. 54.

Referring to FIG. 57, an exploded view of cap 510 and coupling body 520 is shown. The cap 510 is configured to partially fit within coupling body 520. Protrusions 512, 514 (not visible) are sized such that protrusions 512, 514 fit within slots 526, 528 as cap 510 is inserted into coupling body 520. As described previously, as the cap is inserted, rims 516, 518 abut recesses 527, 529, thereby stopping cap 510 at a predetermined longitudinal position within coupling body 520. At the insertion position, the protrusions 512, 514 are aligned with channels 534, 536. Protrusions 512, 514 are sized such that upon rotation of the cap, the protrusions will ride within corresponding channels 534, 536. As also seen in FIG. 57, protrusion 534 is configured with two high points 541, 543 and one low point 542. High points 541, 543 provide interference points when cap 510 is rotated into channel 534; low point 542 provides a relief point when the cap is rotated past the interference point and is in its closed position. While not shown in FIG. 57, one of skill in the art would understand that the interior sidewall of channels 534, 536 are configured with a high point. Accordingly, as the cap is rotated into position, high point 541 interferes with the high point of channel 534. These interference points, however, may be designed such that a user may overcome the interference with sufficient force, allowing the cap to rotate into a final position, wherein the high point of the interior sidewall 539 of the channel 534 fits within the low point 542 on protrusion 512. This interference fit prevents the cap from rotating back into the open position. While the present embodiment utilizes high and low points along the contacting surfaces of the protrusions and channels, one of skill in the art would understand that any variety of interference fits or friction fits may be used to prevent the cap from rotating back into the open position.

Referring to FIGS. 58 and 59, a partial top view of the cap and coupling body is shown. With the cap inserted and in the open position (FIG. 58), protrusions 512, 514 lie within the space created by slots 526, 528. As can be seen in FIG. 58, channel 534 is open to slot 526 and channel 534 is open to slot 528. Accordingly, as the cap is rotated clockwise, protrusions 512, 514 will enter channels 534, 536, respectively. As seen in FIG. 59, cap 510 has been rotated to the closed or second position. In FIG. 59, protrusions 512, 514 are within channels 534, 536.

With continuing reference to FIGS. 58 and 59, relief areas 545, 547 are shown. Relief areas 545, 547 are cavities formed within the interior channels 534, 536. Relief areas 545 and 547 provide an area in which leading edges 546, 548 of protrusions 512, 514 respectively may reside when cap 510 is rotated into the second position. As can be seen in FIG. 59, leading edges 546,548 reside within relief areas 545,547, respectively. The relief areas allow the cap to be rotated a full 90°. Without relief areas 545, 547, the leading edges 546, 548 would come into contact with interior channel walls and impart a radially outward force on arms 522, 524 of coupling body 520. This net radial outward force would impart unwanted forces on the coupling body and may lead to increased splaying of arms 522, 524 when cap 510 is rotated into its second or closed position.

In addition to the anti-splay features, relief areas 545, 547 and leading edges 546, 548 may be designed to provide a mechanical stop. As seen in FIG. 59, when cap 510 is rotated to its closed position, leading edges 546, 548 abut or contact walls 549, 550 of relief areas 545, 547. This contact limits rotation of the cap and prevents the cap from rotating past about 90°. As one of skill in the art would understand, the relief area may be configured in any number of fashions to accommodate the corresponding leading edges of the protrusions. Similarly, the size or length of the channels and protrusions may vary, however, one advantage of the present embodiment is the large surface area of the protrusions and channels. This surface area provides for greater contact between the coupling body and the protrusions of the cap, imparting greater strength and stability to the overall polyaxial screw assembly.

Figure 60:
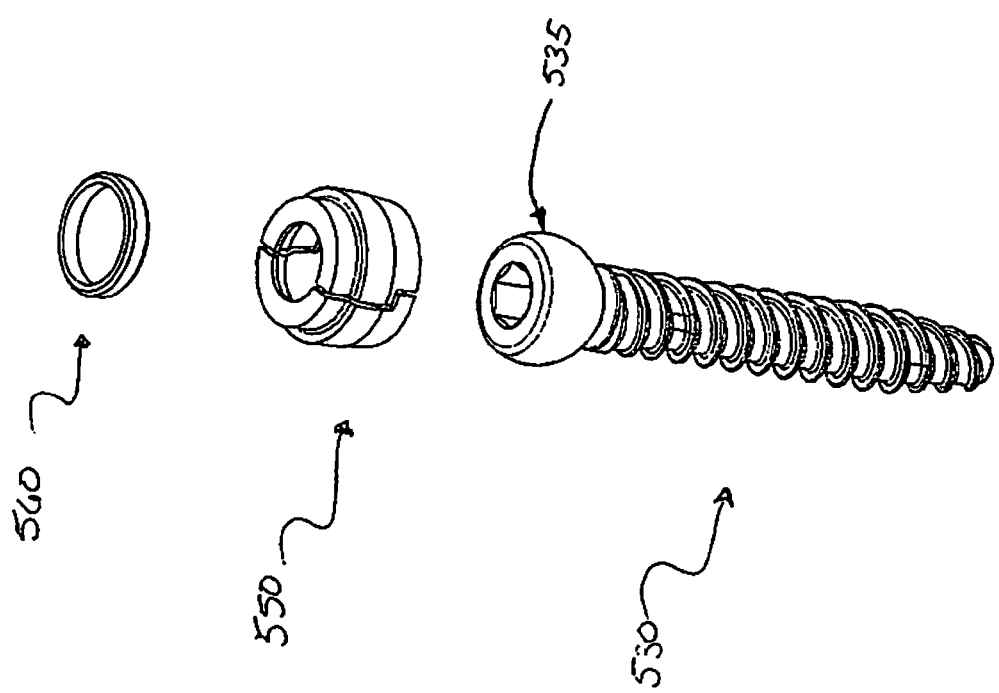
FIG. 60 is a partially exploded view of the embodiment of FIG. 54.

FIG. 60 provides an illustration of the fastener 530, coupling body components 550 and wedge 560. As previously described, the force of an elongate rod (not shown) exerting downward pressure on wedge 560 drives the coupling body components 550 to tighten around head 535 of fastener 530. This assembly, as previously described, locks the various components of the polyaxial screw in a fixed position. Thus, while the coupling body remains free to move about head 353 of fastener 530 prior to the final implantation of the elongate rod, once the components are tightened, the polyaxial screw components become generally fixed in orientation with respect to each other.

Figure 61:
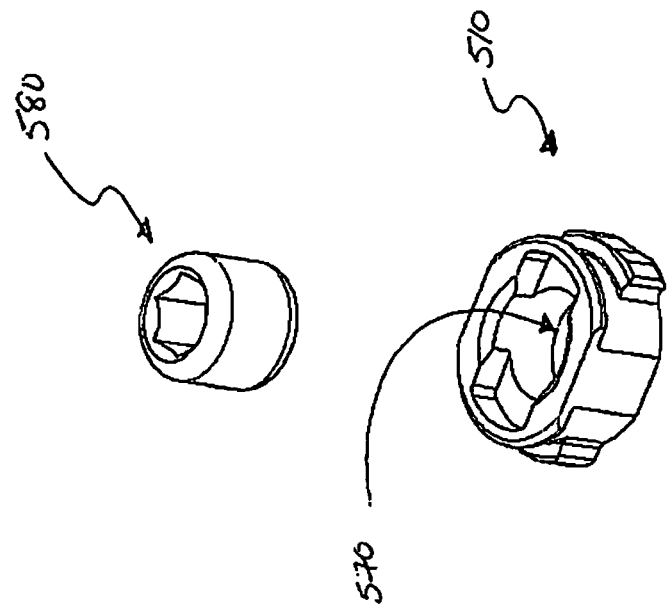
FIG. 61 is a partially exploded view of the cap and set screw of the embodiment of FIG. 54.

As seen in FIG. 61, the cap 510 has a central bore hole 570. A set screw 580 may be provided. In FIG. 61, the set screw 580 is externally threaded (not shown) and the corresponding bore hole 570 is internally threaded (not shown). Upon insertion of the elongate rod and then the cap, the set screw may be used to tighten the various components of the assembly. In this manner, the set screw exerts downward pressure on the rod, which in turn exerts downward pressure on the wedge, coupling body components, and wedge. The cap (and the tongue and groove fits of the protrusions and channels) counteract the counteracting upward force that is experienced by the assembly as a result of the pressure exerted by the set screw. This allows the set screw to create a net downward force to lock the elongate rod, coupling body, and fastener together in a generally fixed orientation.

While the previous embodiment has been shown and described with certain sizing and shape parameters, one of skill in the art would understand that any variety of modifications could be made to achieve similar results. For example, while in the previously described embodiments, the cap is rotated in the clockwise direction, the direction of rotation could easily be changed with modifications to the channels and/or protrusions. Similarly, while the protrusions are shown extending along the perimeter of the cap sidewalls, the length of the protrusions in alternative embodiments could vary. By way of yet another example, the relief areas and leading edges of the channels and protrusions are configured to allow the cap to rotate 90°. Yet, one of skill in the art would readily appreciate that simple design changes could be made to vary the amount of rotation required to place the cap in the second or closed position.

Additional features may be associated with any number of the aforementioned designs. For example, one feature that may be integrated into the previously described embodiments include engagement areas for tools or other apparatus.

Figure 62:
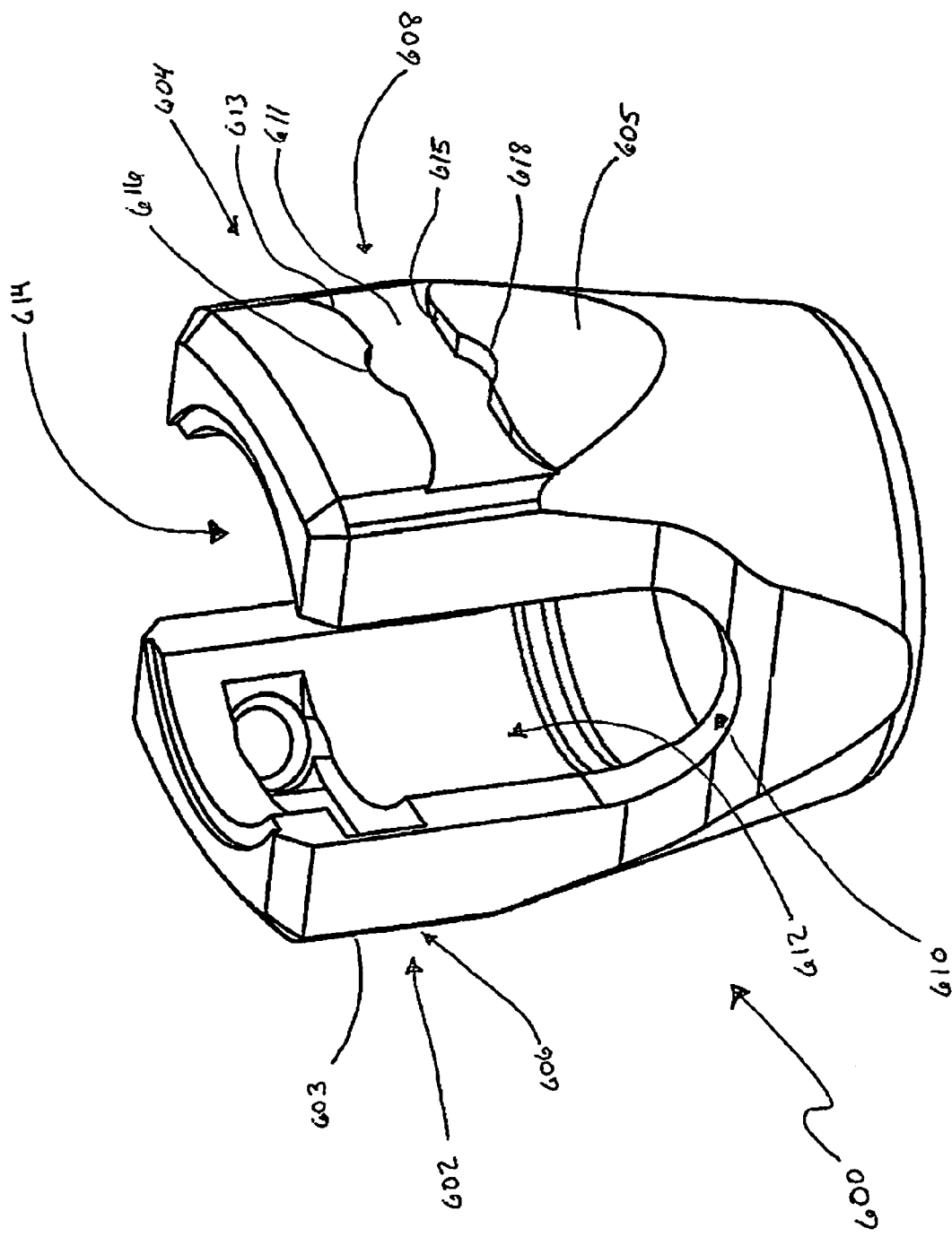
FIG. 62 is a perspective view of a coupling body of another embodiment of the present invention.

Referring to FIG. 62, one such feature is displayed. In FIG. 62, coupling body 600 is shown with two upwardly extending arms 602, 604. Disposed about exterior surfaces 603, 605 of coupling body 600 are engagement areas 606, 608. In this embodiment, engagement areas 606, 608 may be configured or designed to engage with tools or other apparatus. One such example of a tool or apparatus is a reduction device, which may be used by a surgeon during implantation of the elongate rod to reduce the space between seat 610 of coupling body 600 and the elongate rod (not shown). Other examples of tools or apparatus that may engage with engagement areas 606, 608 include positioning devices, minimally invasive system tools, insertion tools, holding apparatus, aligning devices, etc.

As seen in FIG. 62, engagement areas are formed within the exterior sidewalls 603, 605 of coupling body 600. Engagement area 608 has the shape of a generally rectangular channel 611, which runs along a horizontal axis from slot 612 to slot 614. Channel 611 may be designed with additional engagement areas. For example, disposed at sidewalls 613, 615 of channel 611 are semicircular areas 616, 618. Semicircular areas 616, 618 are formed in the exterior surface 605 of arm 604 of coupling body 600, and may be approximately of the same depth as channel 611. Semicircular areas 616, 618 may provide an additional engagement area for a tool or apparatus. For example, a reduction device, may be configured with a round pin or head that engages with the engagement area 608. Furthermore, sidewalls 613, 615 may be formed with back cuts such that they create an angled surface against which tools or other devices may engage. As one of skill in the art would understand, exterior surface 603 of arm 602 of coupling body 600 may similarly be configured with an engagement area 606. Accordingly, a tool may engage with both arms 602, 604 for rod reduction, positioning, alignment, etc.

Figure 63:
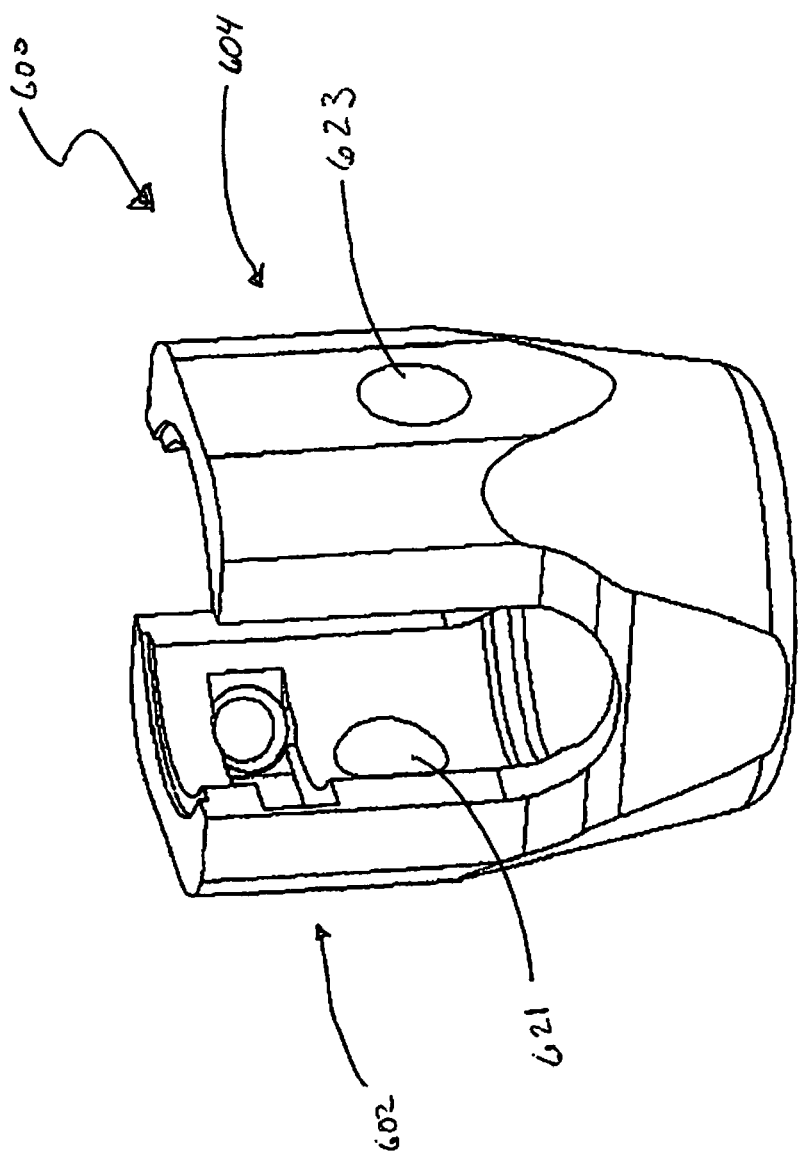
FIG. 63 is a perspective view of a coupling body of another embodiment of the present invention.
Figure 64:
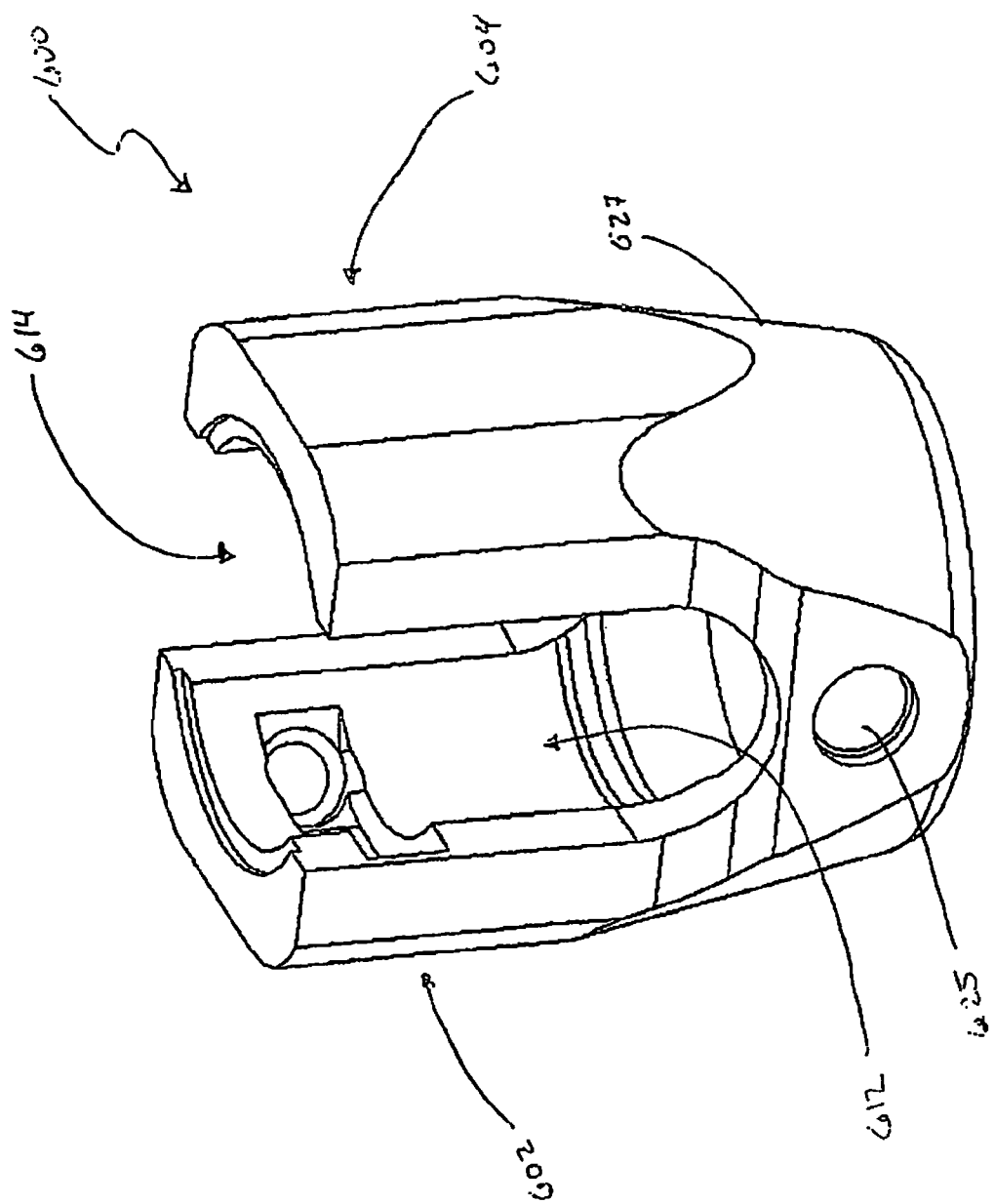
FIG. 64 is a perspective view of a coupling body of another embodiment of the present invention.

Embodiments of the present invention do not contemplate any one particular engagement design. Engagement areas may be placed in any number of positions and may take the form of any number of shapes or configurations. For example and as seen in FIG. 63, one alternative embodiment contemplates the use of bore holes 621, 623 disposed on each of the arms 602, 604 of coupling body 600. Alternatively, holes 621, 623 may be blind holes or holes that do not open to the interior surfaces of coupling body 600. In an alternate embodiment and with reference to FIG. 64, holes 625, 627 may be located on the coupling body 600 below slots 612, 614. As seen in FIG. 64, holes 625, 627 are shown disposed below slots 612, 614 and do not extend to the interior surface of coupling body 600. In alternate embodiments, holes 625, 627 are bore holes and extend through coupling body 600.

Figure 65:
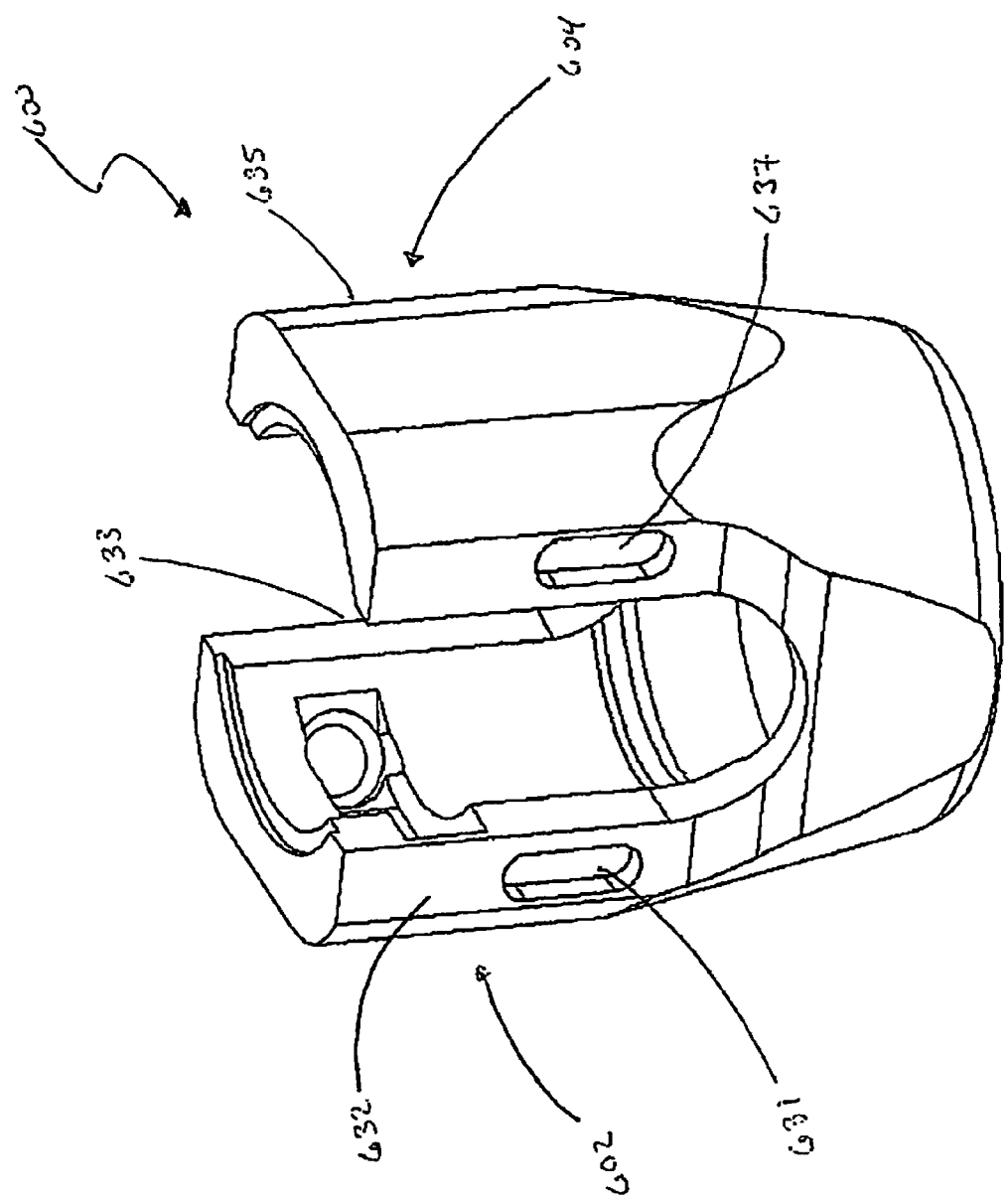
FIG. 65 is a perspective view of a coupling body of another embodiment of the present invention.

In an alternate embodiment and as seen in FIG. 65, engagement areas 631, 633, 635, and 637, may be formed on arms 602, 604 of coupling body 600. Referring to FIG. 65, each arm 302, 304 is configured with two engagement areas, 631, 633 and 635, 637, respectively. Engagement areas may take any number of shapes and may extend into the coupling body by varying amounts, however, the purpose of said engagement areas is to provide an interfacing area at which a tool or other device may engage with said areas and transfer forces to the coupling body, elongate rod, cap, etc. Engagement area 631, in this particular embodiment, is shaped as an extruded cylinder within the sidewall 632 of arm 602. Engagement area 631 is formed into arm 602 of coupling body 600 to a particular depth. While only one engagement area is described, it should be understood that in this embodiment, each engagement area 631, 633, 635, 637 is similarly configured.

Figure 66:
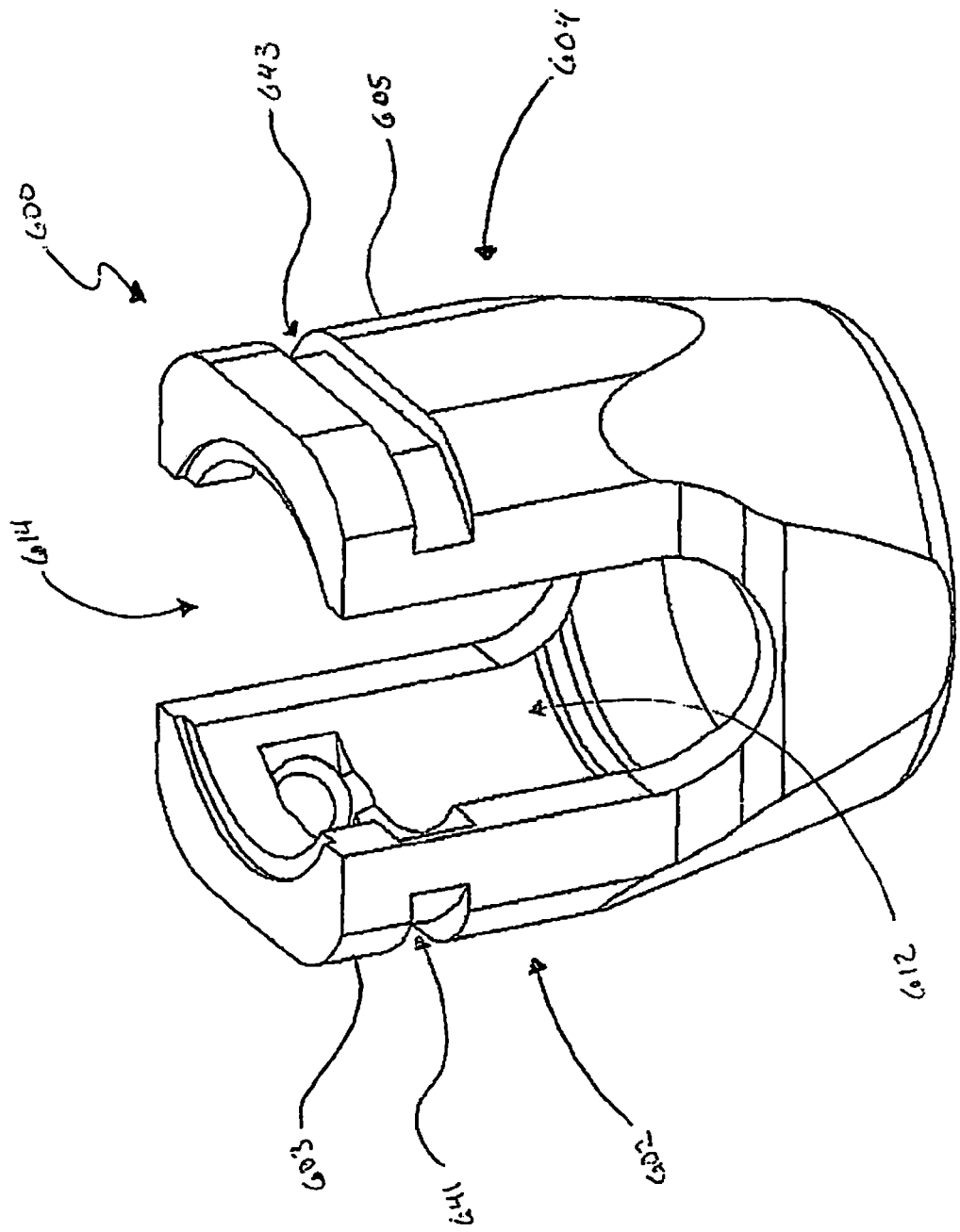
FIG. 66 is a perspective view of a coupling body of another embodiment of the present invention.
Figure 67:
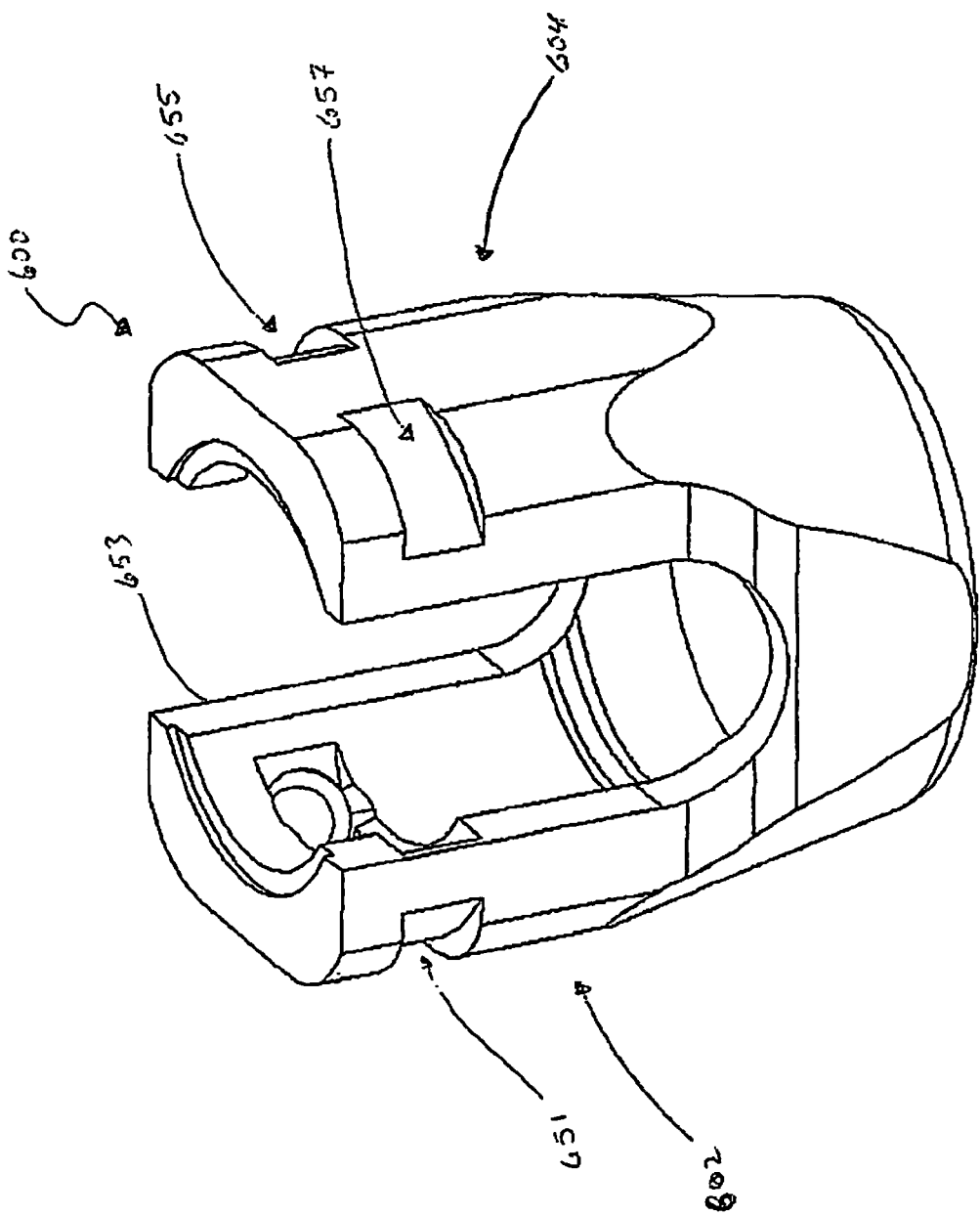
FIG. 67 is a perspective view of a coupling body of another embodiment of the present invention.

In an alternate embodiment and as seen in FIG. 66, coupling body 300 may be formed with engagement areas 641, 643 which take the form of channels disposed about the exterior surfaces 603, 605 of arms 602, 604 of coupling body 600. These channels may differ from those previously described in that as the channels approach slots 612, 614, the channels may be formed at an angle that is tangential to the generally circular shape of the coupling body. Similarly, but of an alternate design, coupling body 600 may have four engagement areas disposed on each arm 602, 604. As seen in FIG. 67, in this alternate embodiment, engagement areas 651, 653, 655, 657 are tangential slots that run along a horizontal axis and are disposed at the proximal and distal ends of arms 602, 604.

Figure 68:
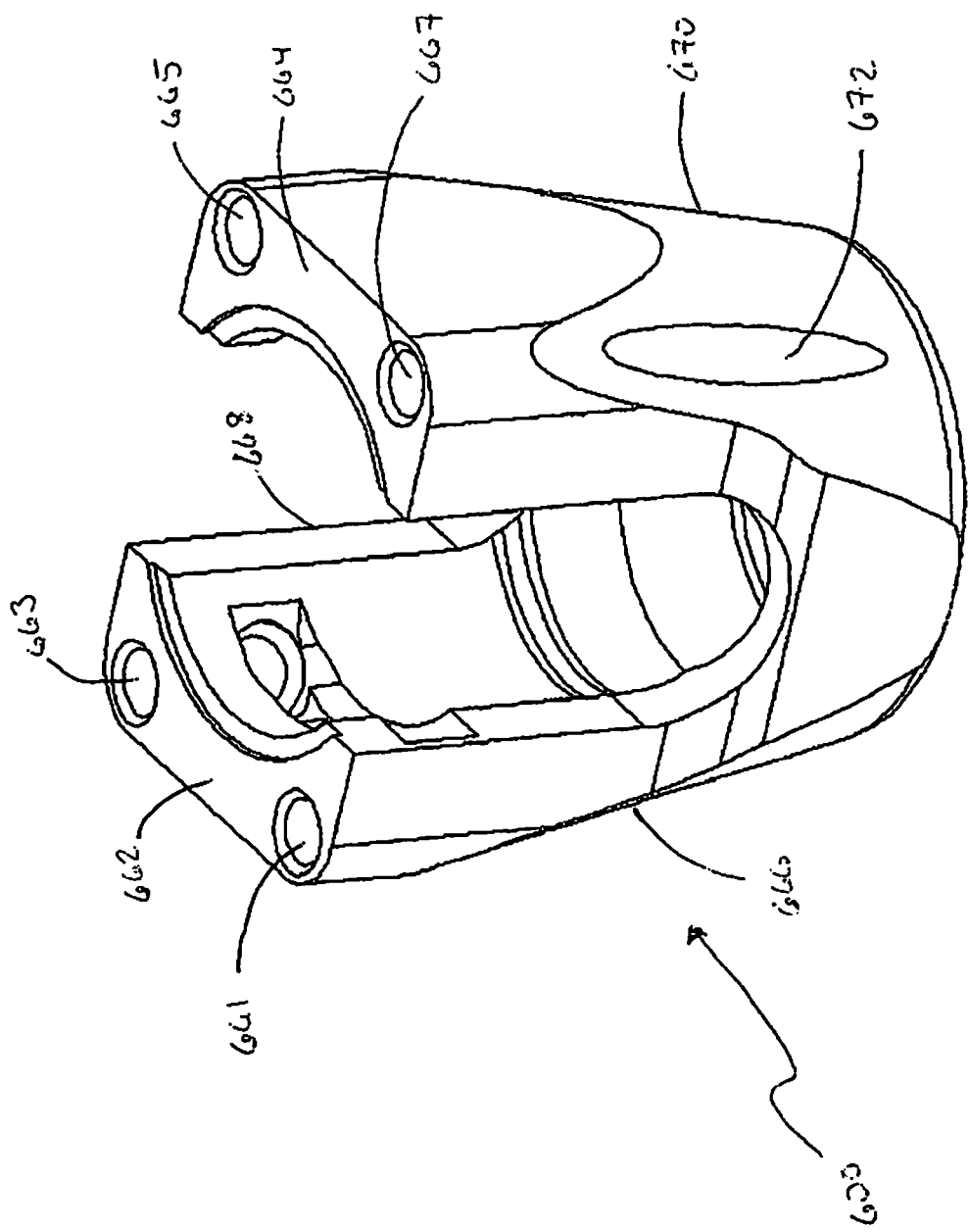
FIG. 68 is a perspective view of a coupling body of another embodiment of the present invention.

Referring to FIG. 68, coupling body 600 may be formed with bore holes 661, 663, 665, and 667. As seen in FIG. 68, bore holes 661, 663, 665, 667 are disposed about the superior surfaces 662, 664 of arms 602, 604. Holes 661, 663, 665, and 667 extend longitudinally in the inferior direction. Because the coupling body is tapered, the holes extend through the coupling body forming openings 666, 668, 670, and 672 at the lower end of the coupling body. Openings 666, 668, 670, and 672 provide engagement areas for tools or other apparatus. Similarly, openings 661, 663, 665, and 667 at superior surfaces 662, 664 may be provide engagement areas for devices, apparatus, or tools.

Figure 69:
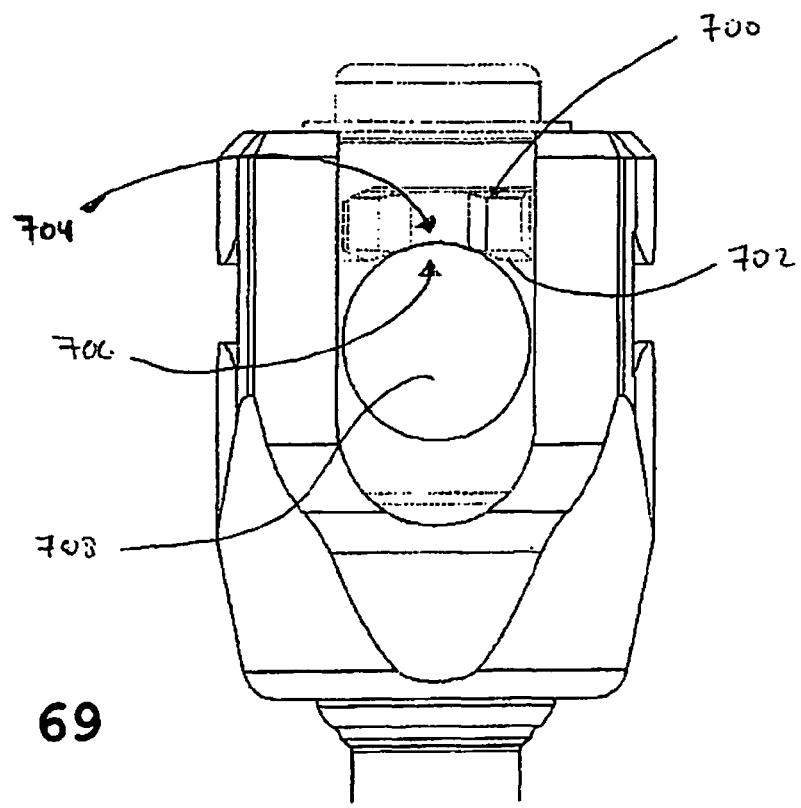
FIG. 69 is a perspective view of another embodiment of the present invention with the cap in a first position.

Additional features may be associated with any number of the aforementioned designs. For example, the cap of the polyaxial screw assembly may be designed to aid the surgeon during implantation of the assembly. One such feature may include a cap with a unique lower surface that interacts with the elongate rod during insertion. Referring to FIG. 69, a polyaxial screw assembly of the present invention is shown. As seen in FIG. 69, cap 700 has an inferior surface 702 which contains a depression area 704 that generally corresponds to the curvature of upper surface 706 of elongate rod 708. Accordingly, when cap 700 is inserted into coupling body 710 in a first position, cap 700 exerts some downward pressure on elongate rod 708. As further seen in FIG. 69, upper surface 706 of elongate rod contacts lower surface 702 of cap 700 and elongate rod 708 partially fits within depression area 704 of cap 700.

Figure 70:
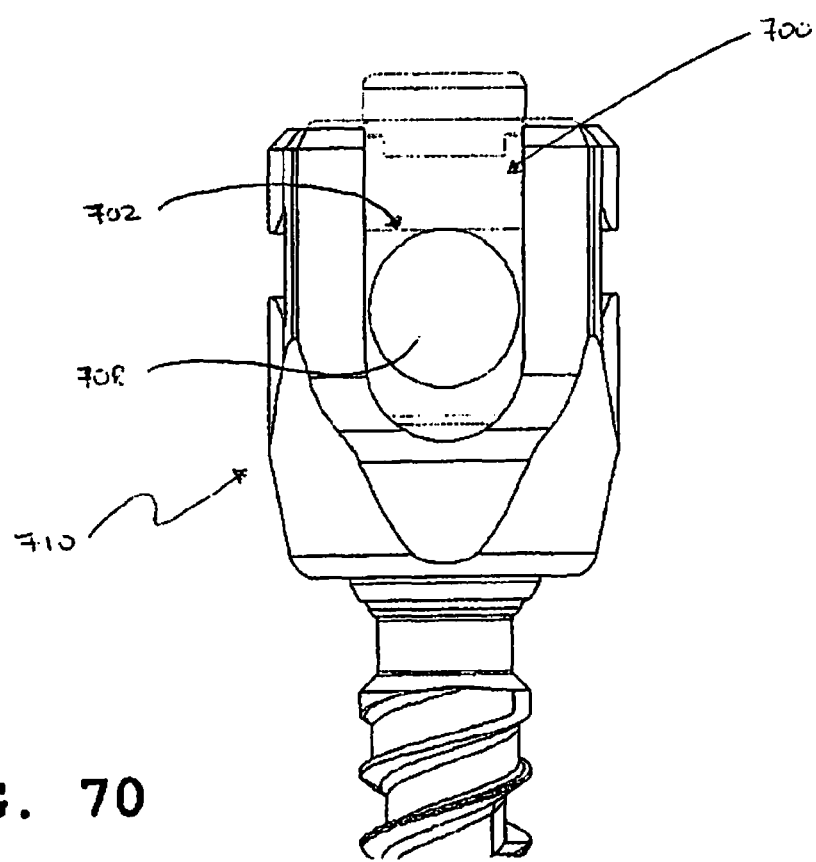
FIG. 70 is a perspective view of another embodiment of the present invention with the cap in a second position.

Turning to FIG. 70, cap 700 has been rotated to its second or closed position. As one of skill in the art would understand, upon rotation of cap 700 from its first position to its second position, the unique shape of the lower surface 702 of cap 700 drives the elongate rod down into coupling body 710. This clamping action of cap 700 aids the surgeon in reducing elongate rod 708. The downward force applied to elongate rod 708 by cap 700 positions elongate rod 708 further into coupling body 710 and increases the ease with which the entire polyaxial screw assembly is implanted into a patient.

As illustrated by the many embodiments described above, the present invention is capable of providing greater flexibility for the physician for installing and adjusting a spinal fixation system. In practice, the physician installs a plurality of fasteners to the treated area of the spine. The fasteners 20 are configured with coupling elements 26 that can be moved and rotated into several positions. The physician may lock in a desired position for the coupling element 26 without requiring the elongated rod to also be locked in position. Likewise, the physician may unlock coupling element 26 from the fastener 20 even after the rod has been locked to the coupling element. Thus, the physician is free to readjust the rotation and angle of the coupling element 26 with respect to the fastener 20 at any time.

In sum, the embodiments described above show that the present invention provides several advantages not previously achieved by the prior art. For instance, one advantage realized by allowing independent locking and unlocking of the rod locking device and the coupling locking device is that the polyaxial screw permits significantly greater adjustability than could be accomplished in the past. Adjustment of the connection between the rod and the coupling device need not risk losing a desired positioning of the coupling element with respect to the screw. Thus, the present invention allows for fine tuning whereas prior systems required were designed to loosen all of the components in order to reposition any component.

In addition to providing greater adjustability, the present invention also reduces the complexity and number of the surgical steps involved for installing a spine stabilization system. The present invention also provides for a more compact design than could be achieved in the past, and reduces the number of separate pieces associated with the implant. Altogether, these advantages will help reduce intra operative time, simplify the surgical procedure, and work well in a wider variety of patient anatomy.

While it is apparent that the invention disclosed herein is well calculated to fulfill the objects stated above, it will be appreciated that numerous modifications and embodiments may be devised by those skilled in the art. Therefore, it is intended that the appended claims cover all such modifications and embodiments that fall within the true spirit and scope of the present invention.

What is claimed is:
1. A spinal implant comprising:
an elongated rod;
a bone fastener having a rounded head;
a coupling element comprising a coupling body and cap;
wherein the coupling body comprises sidewalls that define two upwardly extending arms which define two slots capable of receiving the elongated rod;
wherein the coupling body and cap interact to capture the elongated rod in the coupling body,
wherein first and second protrusion configured on opposing sides of the cap and extend in a radial direction and first and second recesses configured in the two upwardly extending arms extending in a radial direction and wherein the first and second protrusions are configured and dimensioned to engage the first and second recess to limit movement of the cap with respect to the coupling body, when the cap is rotated from a first position to a second position,
wherein the cap having a threaded opening for receiving a threaded locking element, the locking element capable of securely holding the elongated rod in a fixed position relative to the coupling element,
wherein the cap further comprises a rim which extend radially outward from the top end of the perimeter of the cap,
wherein a first of the upwardly extending arms includes a third recess positioned between the first recess and the upper surface of the first of the upwardly extending arms for receiving a first portion of the rim of the cap and a second of the upwardly extending arms includes a fourth recess for receiving a second portion of the rim of the cap, the fourth recess positioned between the second recess and the upper surface of the second of the upwardly extending arms, and
wherein the third recess extends along the length of an inner surface of the first of the upwardly extending arms and the fourth recess extends along the length of an inner surface of the second of the upwardly extending arms.

2. The spine stabilization system of claim 1, wherein the rim engages the upwardly extending arms to align the first and second protrusion s of the cap and the first and second recesses of the coupling body when the cap is inserted into the coupling body.

3. The spine stabilization system of claim 1, wherein the height of the first and second recesses are dimensioned to correspond to the thickness of the first and second protrusion.

4. The spine stabilization system of claim 3, wherein the first and second recesses are configured with first and second relief areas.

5. The spine stabilization system of claim 4, wherein the first and second relief areas interact with the first and second protrusions when the cap is rotated into a final position.

6. The spine stabilization system of claim 1, wherein the cap comprises a lower surface configured to exert downward force upon the elongate rod as the cap is rotated from a first position to a second position.

7. A spine stabilization system comprising:
an elongated rod;
a bone fastener having a rounded head;

wherein the coupling body comprises sidewalls that define first and second upwardly extending arms, said arms defining two slots capable of receiving the elongated rod;

wherein the cap comprises an upper portion and a lower portion, the lower portion of the cap having radially extending first and second protrusions;

wherein the first upwardly extending arm comprises a first recess and a first channel, the first recess configured to engage with the first protrusion of the cap, the second upwardly extending arm comprises a second recess and a second channel, the second recess configured to engage with the second protrusion of the cap, wherein the first and second protrusions of the engage with the first and second recesses of the first and second upwardly extending arms as the cap is rotated from a first position to a second position wherein the cap is configured with a threaded opening for receiving a locking element, the locking element capable of securely holding the elongated rod in a fixed position relative to the coupling element, wherein the cap further comprises a rim which extends radially outward from the upper portion the cap, and wherein the first channel engages with a first portion of the rim of the cap and the second channel engages with a second portion of the rim of the cap, wherein the first channel extends along a majority of the length of an inner surface of the first upwardly extending arms and the second channel extends along a majority of the length of an inner surface of the second upwardly extending arms.

8. The spine stabilization system of claim 7, wherein the coupling body is configured with a first relief area in the first recess.

9. the spine stabilization system of claim 8, wherein the first relief area comprises a first contact surface.

10. The spine stabilization system of claim 9, wherein the first protrusion of the cap comprises a second contact surface.

11. The spine stabilization system of claim 10, wherein the first contact surface and second contact surface abut in a second position to limit rotation of the cap.

12. The spine stabilization system of claim 11, wherein the first and second contact surfaces are configured such that there is no net outward radial force applied to the coupling body when the cap is in the second position.

13. The spine stabilization system of claim 7, wherein the cap is inserted into the coupling body in a first position and may be rotated by about 90° to a second positon.

14. The spine stabilization system of claim 7, wherein the first and second rim of the cap is configured to frictionally cooperate with the first and second channel of the first and second upwardly extending arms.

15. The spine stabilization system of claim 7, wherein the cap comprises a lower surface configured to exert downward force upon the elongate rod as the cap is rotated from a first position to a second position.

* * * * *